US008017832B2

(12) United States Patent
Hoehne et al.

(10) Patent No.: US 8,017,832 B2
(45) Date of Patent: Sep. 13, 2011

(54) PLANT CELLS AND PLANTS WHICH SYNTHESIZE A STARCH WITH AN INCREASED FINAL VISCOSITY

(75) Inventors: Michaela Hoehne, Vevey (CH); Claus Frohberg, Kleinmachnow (DE); Volker Landschuetze, Berlin (DE)

(73) Assignee: Bayer Cropscience AG, Monheim am Rhein (DE)

( * ) Notice: Subject to any disclaimer, the term of this patent is extended or adjusted under 35 U.S.C. 154(b) by 0 days.

(21) Appl. No.: 12/714,167

(22) Filed: Feb. 26, 2010

(65) Prior Publication Data

US 2010/0292461 A1 Nov. 18, 2010

Related U.S. Application Data

(62) Division of application No. 10/539,723, filed as application No. PCT/EP03/14840 on Dec. 19, 2003, now Pat. No. 7,714,186.

(30) Foreign Application Priority Data

Dec. 19, 2002 (EP) .................................... 02028530
Aug. 29, 2003 (EP) .................................... 03090275

(51) Int. Cl.
*C12N 15/82* (2006.01)
*C12N 15/87* (2006.01)
*C12N 15/11* (2006.01)
*C12N 15/29* (2006.01)

(52) U.S. Cl. ..... 800/285; 800/284; 800/286; 435/320.1; 435/468; 536/23.6; 536/24.5

(58) Field of Classification Search .......................... None
See application file for complete search history.

(56) References Cited

U.S. PATENT DOCUMENTS

| | | | |
|---|---|---|---|
| 4,962,028 A | 10/1990 | Bedbrook et al. |
| 5,034,322 A | 7/1991 | Rogers et al. |
| 5,639,952 A | 6/1997 | Quail et al. |
| 5,656,496 A | 8/1997 | Quail et al. |
| 6,376,749 B1 | 4/2002 | Broglie et al. |
| 6,468,799 B1 | 10/2002 | Burrell |
| 6,596,928 B1 | 7/2003 | Landschutze |
| 7,247,769 B2 | 7/2007 | Landschutze |
| 7,385,104 B2 | 6/2008 | Landschutze |
| 2002/0032919 A1 | 3/2002 | Chang et al. |

FOREIGN PATENT DOCUMENTS

| | | |
|---|---|---|
| EP | 0120516 | 10/1984 |
| EP | 0292435 | 11/1988 |
| EP | 0321201 | 6/1989 |
| EP | 0465875 | 1/1992 |
| EP | 0513849 | 11/1992 |
| WO | WO 91/01373 | 2/1991 |
| WO | WO 93/11376 | 7/1992 |
| WO | WO 93/07279 | 4/1993 |
| WO | WO 95/06128 | 3/1995 |
| WO | WO 95/15972 | 6/1995 |
| WO | WO 96/34968 | 11/1996 |
| WO | WO 97/04112 | 2/1997 |
| WO | WO 97/04113 | 2/1997 |
| WO | WO 97/20040 | 6/1997 |
| WO | WO 98/37213 | 8/1998 |
| WO | WO 98/37214 | 8/1998 |
| WO | WO 99/53050 | 10/1999 |
| WO | WO 99/66050 | 12/1999 |
| WO | WO 00/08184 | 2/2000 |
| WO | WO 00/66745 | 11/2000 |

OTHER PUBLICATIONS

A. Blennow, et al. (2002) "Starch phosphorylation, a new front line in starch research", Trends in Plant Science, vol. 7(10), pp. 445-450.
Aarts et al. (1993) Nature 363, pp. 715-717.
Abel et al. (1996) The Plant Journal 10(6), pp. 981-991.
Ali and Siddiq (1999) Indian Journal of Genetics 59(1), pp. 23-28.
Altman et al. (1992) Theoretical and Applied Genetics 84, pp. 371-383.
Ames "Assay of Inorganic Phosphate, Total Phosphate and Phosphatases" Complex Carbohydrates vol. VIII (1966), pp. 115-118.
An et al. (1985) EMBO J. 4, pp. 277-287.
Atipiroz-Leehan and Feldmann (1997) Trends in genetics 13 (4), pp. 152-156.
Baba et al. (1991) "Sequence Conservation of the Catalytic Regions of Amylolytic 1 Enzymes in Maize Branching Enzyme-I," Biochemical and Biophysical Research Communications, vol. 181(1), pp. 98-94.
Bachem et al. (1996) The Plant Journal 9(5), pp. 745-753.
Bansal et al. (1992) PNAS USA 89, pp. 3654-3658.
Baumlein et al. (1991) Mol. Gen. Genet. 225, pp. 459-467.
Beetham et al., (1999) PNAS 96, pp. 8774-8778.
Belzile and Yoder (1992) The Plant Journal 2(2), pp. 173-179.
Bevan (1984) Nucleic Acid Research 12, pp. 8711-8721.
Bolivar et al. (1977) Construction and Characterization of new cloning vehicles II. Gene 2, pp. 95-113.
Castiglioni et al. (1998) Genetics 149, pp. 2039-2056.
Chan et al. (1993) Plant Mol. Biol. 22, pp. 491-506.
Cho et al. (1999) Nature Genetics 23, pp. 203-207.
Cole-Strauss et al. (1996) Science 273, pp. 1386-1389.
Conner and Domisse (1992) Int. J. Plant Sci. 153, pp. 550-555.
Cornelissen and Vanderwiele (1989) Nucleic Acid Research 17, pp. 19-25.
de Borne et al. (1994) Mol. Gen. Genet. 243, pp. 613-621.
de Feyter et al. (1996) Mol. Gen. Genet. 250, pp. 329-338.

(Continued)

*Primary Examiner* — Brent T Page
(74) *Attorney, Agent, or Firm* — Hunton & Williams LLP

(57) ABSTRACT

The present invention relates to a plant cell which is genetically modified, the genetic modification leading to the reduction of the activity of one or more SSIII proteins which occur endogenously in the plant cell and to the reduction of the activity of one or more BEI proteins which occur endogenously in the plant cell and to the reduction of the activity of one or more BEII proteins which occur endogenously in the plant cell in comparison with corresponding plant cells, of wild-type plants, which have not been genetically modified. Further aspects of the invention relate to plants containing such plant cells, to a method for generating the plant cells and plants, and to the starch obtainable from them.

20 Claims, 12 Drawing Sheets

OTHER PUBLICATIONS

Deng et al. "Agrobacterium tumefaciens can transform Tiricum aestivum and Hordeum vulgare of Gramineae." Science In China (Series B) 33(1), pp. 27-33, Jan. 1990.
Dixon and Antzen "Transgenic plant technology is entering the era of metabolic engineering." Tibtech (Nov. 1997) 15, pp. 441-444.
Drenkard et al. (2000) Plant Physiology 124, pp. 1483-1492.
Edwards et al. (Feb. 1999) Plant Journal 17(3), pp. 251-261.
Edwards et al., (2002), The Plant Cell, 14, pp. 1767-1785.
Enoki et al. (1999) The Plant Journal 19 (5), pp. 605-613.
Fiedler et al. (1993) Plant Mol. Biol. 22, pp. 669-679.
Franken et al. "Recombinant proteins form transgenic plants." Current Opinion in Biotechnology (1997), pp. 411-416.
Frey et al. (1989) Molecular and General Genetics 217, pp. 172-177.
Fromm et al. (1990) Biotechnology 8, pp. 833-844.
Gao et al. (1998) Plant Cell 10(3), pp. 399-412.
Gérard et al. (2001) Carbohydrate Polymers 44, pp. 19-27.
Gielen et al. (1984) EMBO J. 3, pp. 835-846.
Gordon-Kamm et al. (1990) Plant Cell 2, pp. 603-618.
Greco et al. (2001) Plant Physiology 125, pp. 1175-1177.
Gupta and Sharma (1990) Oryza 27, pp. 217-219.
Hanley et al. (2000) "Identification of transposon-tagged genes by the random sequencing of Mutator-tagged DNA fragments from *Zea mays*." The Plant Journal 23(4), pp. 557-566.
Hiei et al. (1994) Plant J. pp. 271-282.
Hirochika (2001) Current Opinion in Plant Biology 4, pp. 118-122.
Hizukuri and Takagi (1984) Carbohydrate Res. 134, pp. 1-10.
Höfgen and Willmitzer (1990) Plant Sci. 66, pp. 221-230.
Hoogkamp et al. "Development of amylose-free (amf) monoploid potatoes as new basic material for mutation breeding in vitro." Potato Research 43 (2000), pp. 179-189.
Hovenkamp-Hermelink et al (1987) Theoretical and Applied Genetics 75, pp. 217-221.
Itoh et al. (1984) Genetic and molecular characterization of the Pseudomonas plasmid pVS1. Plasmid 11, pp. 206-220.
Jarvis et al. (1994) Plant Molecular Biology 24, pp. 685-687.
Jeon et al. (2000) The Plant Journal 22(6), pp. 561-570.
Jeon et al. (2001) "Gene tagging in rice, a high throughput system for functional genomics." Plant Science 161, pp. 211-219.
Jobling et al. (1999) The Plant Journal 18(2), pp. 163-171.
Jorgensen (1990) "Altered gene expression in plants due to trans interactions between homologous genes." Trends Biotechnol. 8, pp. 340-344.
Khoshnoodi, et al. (1996) "The multiple forms of starch-branching enzyme I in *Solanum tuberosum*," Eur. J. Biochem. 242, pp. 148-155.
Kim, et al. (1998) "Genomic Organization and Promoter Activity of the Maize Starch Branching Enzyme I Gene," Gene 216, pp. 233-243.
Knapp et al. (1988) Molecular and General Genetics 213, pp. 285-290.
Konieczny and Ausubel (1993) The Plant Journal 4, pp. 403-410.
Koprek et al. (2000) The Plant Journal 24(2), pp. 253-263.
Kossman and Lloyd (2000) Critical Reviews in Plant Sciences 19(3), pp. 171-126.
Kobmann, et al. (1991) "Cloning and expression analysis of a potato cDNA that encodes branching enzyme, evidence of co-expression of starch biosynthetic genes," Mol. Gen. Genet (1991) 230, pp. 39-44.
Koziel et al. (1993) Biotechnology 11, pp. 194-200.
Kren et al. (1997) Hepatology 25, pp. 1462-1468.
Krens et al. (1982) Nature 296, pp. 72-74.
Krysan et al. (1999) The Plant Cell 11, pp. 2283-2290.
Kugimiya et al. (1999) The Journal of Food Science 46, pp. 765-770.
Kumar and Hirochika (2001) Trends in Plant Science 6 (3), pp. 127-134.
Larsson, et al. (1998) "Molecular cloning and characterization of starch-branching enzyme II from potato", Plant Molecular Biology 37, pp. 505-511.
Leister and Dean (1993) The Plant Journal 4(4), pp. 745-750.
Leisy et al. (1990) Plant Mol. Biol. 14, pp. 41-50.
Li et al. (2000) Plant Physiology 123, pp. 613-624.
Liu et al. (1999) Molecular and General Genetics 262, pp. 413-420.
Liu et al. (2000) Biochemical Society Transactions 28(6), pp. 927-929.
Lloyd et al. (Mar. 1, 1999) Biochemical Journal 338(2), pp. 515-521.
Maes et al. (1999) Trends in Plant Science 4(3) pp. 90-96.
Marshall et al. (1996) The Plant Cell 8, pp. 1121-1135.
May et al. Bio/Technology (1995) 13, pp. 486-492.
McCallum et al. (2000) Plant Physiology 123, pp. 439-442.
McKinney et al. (1995) The Plant Journal 8(4), pp. 613-622.
Meksem et al. (2001) Molecular Genetics and Genomics 265, pp. 207-214.
Mette et al. (2000) EMBO J. 19, pp. 5194-5201.
Meyer at al. (1998) Molecular and General Genetics 259, pp. 150-160.
Mórocz et al. (2000) Theor. Appl. Genet. 80, pp. 721-726.
Morrison and Laignelet (1983) J Cereal Sc. 1, pp. 9-20.
Müller (1972) Biologisches Zentralblatt 91(1), pp. 31-48.
Nam et al. (1989) The Plant Cell 1, pp. 699-705.
NCBI Information AJ011889 *Solanum tuberosum* mRNA for starch branching enzymes II, sequence SBE A-5 (submitted Oct. 7, 1998).
Nehra et al. (1994) Plant J. 5, pp. 285-297.
Nielsen et al. (1994) Plant Physiol. 105, pp. 111-117.
Odell et al. (1985) Nature 313, pp. 810-812.
Owen (1992) Bio/Technology 10, pp. 790-794.
Palaqui and Vaucheret (1995) Plant. Mol. Biol. 29, pp. 149-159.
Parinov and Sundaresan (2000) Current Opinion in Biotechnology 11, pp. 157-161.
Parinov et al. (1999) The Plant Cell 11, pp. 2263-2270.
Patron et al., (2002) Plant Physiology, vol. 130, pp. 190-198.
Pedersen et al. (1982) Cell 29, pp. 1015-1026.
Qi et al. (2001) Nucleic Acids Research 29(22), p. e116.
Quatroccio et al. (1990) Plant Mol. Biol. 15, pp. 81-93.
Ramachandran and Sundaresan (2001) Plant Physiology and Biochemistry 39, pp. 243-252.
Rao (1977) Cytologia 42, pp. 443-450.
Ritala et al. (1994) Plant Mol. Biol. 24, pp. 317-325.
Ritchie et al. "*Agrobacterium tumefaciens*-mediated expression of gusA in maize tissues." Transgenic Research (1993) 2, pp. 252-265.
Rocha-Sosa et al. (1989) EMBO J. 8, pp. 23-29.
Safford et al. (1998) Carbohydrate Polymers 35, pp. 155-168.
Satoh and Omura "New Endosperm Mutations Induced by Chemical Mutagens in Rice, *Oryza sativa* L." Japan J. Breed (1981) 31(3), pp. 316-326.
Scarascia-Mugnozza et al. (1993) Mutation Breeding Review 10, pp. 1-28.
Schmidt and Willmitzer (1989) Molecular and General Genetics 220, pp. 17-24.
Schwall et al. (2000) Nature Biotechnology 18, pp. 551-554.
Sievert and Holm (1993) Starch/Starke 45(4), pp. 136-139.
Singh et al. (2000) Biochemical Society Transactions 28(6), pp. 925-927.
Slattery et al. (Jul. 2000) Trends in Plant Science 5(7), pp. 291-298.
Smith et al. (2000) Nature 407, pp. 319-320.
Smith-White et al. (1994) "Suggested Mnemonics for Cloned DNA Corresponding to Enzymes Involved in Starch Metabolism", Plant Molecular Biology Reporter 12, pp. S67-S71.
Spencer et al. (1990) Theor. Appl. Genet. 79, pp. 625-631.
Stockhaus et al. (1987) PNAS USA 84, pp. 7943-7947.
Stockhaus et al. (1989) EMBO J. 8, pp. 2445-2451.
Tetlow et al., (2004) Journal of Experimental Botany, 55, No. 406, pp. 2131-2145.
Thompson et al. (1987) The EMBO Journal 6, pp. 2519-2523.
Thompson et al. (1994) Nucleic Acids Research 22, pp. 4673-4680.
Thorneycroft et al. (2001) Journal of Experimental Botany 52, pp. 1593-1601.
Tissier et al. (1999) The Plant Cell 11, pp. 1841-1852.
Tolmasky (1990) Sequencing and Expression of aadA, bla, and tnpR from the multiresistance transposon Tn1331 Plasmid 24(3), pp. 218-226.
Tolmasky and Crosa (1993) Plasmid, 29, No. 1, pp. 31-40.
Vasil et al. Bio/Technology (1993) 11, pp. 1553-1558.
Vaucheret et al. (1995) Mol. Gen. Genet. 248, pp. 311-317.
Vaucheret et al. (2001) Trends in Genetics 17, pp. 29-35.
Wan and Lemaux (1994) Plant Physiol. 104, pp. 37-48.
Wang and Waterhouse (2000) Plant Mol. Biol. 43, pp. 67-82.
Waterhouse et al. (1998) PNAS 95, pp. 13959-13964.
Werr et al. (1993) EMBO J. 4, pp. 1373-1380.
Whitelam (1996) Trends Plant Sci. 1, pp. 268-272.
Wilmink et al. (1992) Plant Cell Reports 11, pp. 76-80.
Yoshihara et al. (1996) FEBS Lett. 383, pp. 213-218.
Young et al. (2001) Plant Physiology 125, pp. 513-518.
Zheng et al. (1993) Plant J. 4, pp. 357-366.

SEQUENCE LISTING

```
<160> NUMBER OF SEQ ID NOS: 10

<210> SEQ ID NO 1
<211> LENGTH: 4167
<212> TYPE: DNA
<213> ORGANISM: Solanum tuberosum
<220> FEATURE:
<221> NAME/KEY: CDS
<222> LOCATION: (207)..(3899)
<300> PUBLICATION INFORMATION:
<301> AUTHORS: Abel,G.J., Springer,F., Willmitzer,L. and Kossmann,J.
<302> TITLE: Cloning and functional analysis of a cDNA encoding a novel
       139 kDa
<303> JOURNAL: Plant J.
```

<304> VOLUME: 10
<305> ISSUE: 6
<306> PAGES: 981-991
<307> DATE: 1996
<308> DATABASE ACCESSION NUMBER: X94400
<309> DATABASE ENTRY DATE: 1995-12-22
<313> RELEVANT RESIDUES IN SEQ ID NO: (1)..(4167)
<300> PUBLICATION INFORMATION:
<308> DATABASE ACCESSION NUMBER: EMBL / X94400
<309> DATABASE ENTRY DATE: 1997-04-16
<313> RELEVANT RESIDUES IN SEQ ID NO: (1)..(4167)

<400> SEQUENCE: 1

```
tttttaata gattttaaa accccattaa agcaaatacg tatataattg cagcacagat    60
acagagaggg agagagaaag atagtgtgtt gatgaaggag aagagagata tttcacatgg   120
gatgttctat tgattctgt ggtgaacaag agttttacaa agaacattcc ttttctttt    180 tttcttggtt cttgtgtggg tcagcc atg gat gtt cca ttt cca ctg cat aga   233
                              Met Asp Val Pro Phe Pro Leu His Arg
                                1               5 cca ttg agt tgc aca agt gtc tcc aat gca ata acc cac ctc aag atc    281
Pro Leu Ser Cys Thr Ser Val Ser Asn Ala Ile Thr His Leu Lys Ile
 10              15                  20                  25 aaa cct ttt ctt ggg ttt gtc tct cat gga acc aca agt cta tca gta    329
Lys Pro Phe Leu Gly Phe Val Ser His Gly Thr Thr Ser Leu Ser Val
             30                  35                  40 caa tct tct tca tgg agg aag gat gga atg gtt act ggg gtt tca ttt    377
Gln Ser Ser Ser Trp Arg Lys Asp Gly Met Val Thr Gly Val Ser Phe
         45                  50                  55 cca ttt tgt gca aat ctc tcg gga aga aga cgg aga aaa gtt tca act    425
Pro Phe Cys Ala Asn Leu Ser Gly Arg Arg Arg Arg Lys Val Ser Thr
     60                  65                  70 act agg agt caa gga tct tca cct aag ggg ttt gtg cca agg aag ccc    473
Thr Arg Ser Gln Gly Ser Ser Pro Lys Gly Phe Val Pro Arg Lys Pro
 75                  80                  85 tca ggg atg agc acg caa aga aag gtt cag aag agc aat ggt gat aaa    521
Ser Gly Met Ser Thr Gln Arg Lys Val Gln Lys Ser Asn Gly Asp Lys
 90                  95                 100                 105 gaa agt caa agt act tca aca tct aaa gaa tct gaa att tcc aac cag    569
Glu Ser Gln Ser Thr Ser Thr Ser Lys Glu Ser Glu Ile Ser Asn Gln
            110                 115                 120 aag acg gtt gaa gca aga gtt gaa act agt gac gat gac act aaa gta    617
Lys Thr Val Glu Ala Arg Val Glu Thr Ser Asp Asp Asp Thr Lys Val
        125                 130                 135 gtg gtg agg gac cac aag ttt ctg gag gat gag gat gaa atc aat ggt    665
Val Val Arg Asp His Lys Phe Leu Glu Asp Glu Asp Glu Ile Asn Gly
    140                 145                 150 tct act aaa tca ata agt atg tca cct gtt cgt gta tca tct caa ttt    713
Ser Thr Lys Ser Ile Ser Met Ser Pro Val Arg Val Ser Ser Gln Phe
155                 160                 165 gtt gaa agt gaa gaa act ggt ggt gat gac aag gat gct gta aag tta    761
Val Glu Ser Glu Glu Thr Gly Gly Asp Asp Lys Asp Ala Val Lys Leu
170                 175                 180                 185 aac aaa tca aag aga tcg gaa gag agt gat ttt cta att gat tct gta    809
Asn Lys Ser Lys Arg Ser Glu Glu Ser Asp Phe Leu Ile Asp Ser Val
            190                 195                 200 ata aga gaa caa agt gga tct cag ggg gaa act aat gcc agt agc aag    857
Ile Arg Glu Gln Ser Gly Ser Gln Gly Glu Thr Asn Ala Ser Ser Lys
        205                 210                 215 gga agc cat gct gtg ggt aca aaa ctt tat gag ata ttg cag gtg gat    905
Gly Ser His Ala Val Gly Thr Lys Leu Tyr Glu Ile Leu Gln Val Asp
    220                 225                 230
```

```
gtt gag cca caa caa ttg aaa gaa aat aat gct ggg aat gtt gaa tac      953
Val Glu Pro Gln Gln Leu Lys Glu Asn Asn Ala Gly Asn Val Glu Tyr
235                 240                 245 aaa gga cct gta gca agt aag cta ttg gaa att act aag gct agt gat     1001
Lys Gly Pro Val Ala Ser Lys Leu Leu Glu Ile Thr Lys Ala Ser Asp
250                 255                 260                 265 gtg gaa cac act gaa agc aat gag att gat gac tta gac act aat agt     1049
Val Glu His Thr Glu Ser Asn Glu Ile Asp Asp Leu Asp Thr Asn Ser
                270                 275                 280 ttc ttt aaa tca gat tta att gaa gag gat gag cca tta gct gca gga     1097
Phe Phe Lys Ser Asp Leu Ile Glu Glu Asp Glu Pro Leu Ala Ala Gly
            285                 290                 295 aca gtg gag act gga gat tct tct cta aac tta aga ttg gag atg gaa     1145
Thr Val Glu Thr Gly Asp Ser Ser Leu Asn Leu Arg Leu Glu Met Glu
        300                 305                 310 gca aat cta cgt agg cag gct ata gaa agg ctt gcc gag gaa aat tta     1193
Ala Asn Leu Arg Arg Gln Ala Ile Glu Arg Leu Ala Glu Glu Asn Leu
    315                 320                 325 ttg caa ggg atc aga tta ttt tgt ttt cca gag gtt gta aaa cct gat     1241
Leu Gln Gly Ile Arg Leu Phe Cys Phe Pro Glu Val Val Lys Pro Asp
330                 335                 340                 345 gaa gat gtc gag ata ttt ctt aac aga ggt ctt tcc act ttg aag aat     1289
Glu Asp Val Glu Ile Phe Leu Asn Arg Gly Leu Ser Thr Leu Lys Asn
                350                 355                 360 gag tct gat gtc ttg att atg gga gct ttt aat gag tgg cgc tat agg     1337
Glu Ser Asp Val Leu Ile Met Gly Ala Phe Asn Glu Trp Arg Tyr Arg
            365                 370                 375 tct ttt act aca agg cta act gag act cat ctc aat gga gat tgg tgg     1385
Ser Phe Thr Thr Arg Leu Thr Glu Thr His Leu Asn Gly Asp Trp Trp
        380                 385                 390 tct tgc aag atc cat gtt ccc aag gaa gca tac agg gct gat ttt gtg     1433
Ser Cys Lys Ile His Val Pro Lys Glu Ala Tyr Arg Ala Asp Phe Val
    395                 400                 405 ttt ttt aat gga caa gat gtc tat gac aac aat gat gga aat gac ttc     1481
Phe Phe Asn Gly Gln Asp Val Tyr Asp Asn Asn Asp Gly Asn Asp Phe
410                 415                 420                 425 agt ata act gtg aaa ggt ggt atg caa atc att gac ttt gaa aat ttc     1529
Ser Ile Thr Val Lys Gly Gly Met Gln Ile Ile Asp Phe Glu Asn Phe
                430                 435                 440 ttg ctt gag gag aaa tgg aga gaa cag gag aaa ctt gct aaa gaa caa     1577
Leu Leu Glu Glu Lys Trp Arg Glu Gln Glu Lys Leu Ala Lys Glu Gln
            445                 450                 455 gct gaa aga gaa aga cta gcg gaa gaa caa aga cga ata gaa gca gag     1625
Ala Glu Arg Glu Arg Leu Ala Glu Glu Gln Arg Arg Ile Glu Ala Glu
        460                 465                 470 aaa gct gaa att gaa gct gac aga gca caa gca aag gaa gag gct gca     1673
Lys Ala Glu Ile Glu Ala Asp Arg Ala Gln Ala Lys Glu Glu Ala Ala
    475                 480                 485 aag aaa aag aaa gta ttg cga gaa ttg atg gta aaa gcc acg aag act     1721
Lys Lys Lys Lys Val Leu Arg Glu Leu Met Val Lys Ala Thr Lys Thr
490                 495                 500                 505 cgt gat atc acg tgg tac ata gag cca agt gaa ttt aaa tgc gag gac     1769
Arg Asp Ile Thr Trp Tyr Ile Glu Pro Ser Glu Phe Lys Cys Glu Asp
                510                 515                 520 aag gtc agg tta tac tat aac aaa agt tca ggt cct ctc tcc cat gct     1817
Lys Val Arg Leu Tyr Tyr Asn Lys Ser Ser Gly Pro Leu Ser His Ala
            525                 530                 535 aag gac ttg tgg atc cac gga gga tat aat aat tgg aag gat ggt ttg     1865
Lys Asp Leu Trp Ile His Gly Gly Tyr Asn Asn Trp Lys Asp Gly Leu
        540                 545                 550
```

```
                                                        -continued
tct att gtc aaa aag ctt gtt aaa tct gag aga ata gat ggt gat tgg   1913
Ser Ile Val Lys Lys Leu Val Lys Ser Glu Arg Ile Asp Gly Asp Trp
555                 560                 565 tgg tat aca gag gtt gtt att cct gat cag gca ctt ttc ttg gat tgg   1961
Trp Tyr Thr Glu Val Val Ile Pro Asp Gln Ala Leu Phe Leu Asp Trp
570                 575                 580                 585 gtt ttt gct gat ggt cca ccc aag cat gcc att gct tat gat aac aat   2009
Val Phe Ala Asp Gly Pro Pro Lys His Ala Ile Ala Tyr Asp Asn Asn
                590                 595                 600 cac cgc caa gac ttc cat gcc att gtc ccc aac cac att ccg gag gaa   2057
His Arg Gln Asp Phe His Ala Ile Val Pro Asn His Ile Pro Glu Glu
            605                 610                 615 tta tat tgg gtt gag gaa gaa cat cag atc ttt aag aca ctt cag gag   2105
Leu Tyr Trp Val Glu Glu Glu His Gln Ile Phe Lys Thr Leu Gln Glu
        620                 625                 630 gag aga agg ctt aga gaa gcg gct atg cgt gct aag gtt gaa aaa aca   2153
Glu Arg Arg Leu Arg Glu Ala Ala Met Arg Ala Lys Val Glu Lys Thr
    635                 640                 645 gca ctt ctg aaa act gaa aca aag gaa aga act atg aaa tca ttt tta   2201
Ala Leu Leu Lys Thr Glu Thr Lys Glu Arg Thr Met Lys Ser Phe Leu
650                 655                 660                 665 ctg tct cag aag cat gta gta tat act gag cct ctt gat atc caa gct   2249
Leu Ser Gln Lys His Val Val Tyr Thr Glu Pro Leu Asp Ile Gln Ala
                670                 675                 680 gga agc agc gtc aca gtt tac tat aat ccc gcc aat aca gta ctt aat   2297
Gly Ser Ser Val Thr Val Tyr Tyr Asn Pro Ala Asn Thr Val Leu Asn
            685                 690                 695 ggt aaa cct gaa att tgg ttc aga tgt tca ttt aat cgc tgg act cac   2345
Gly Lys Pro Glu Ile Trp Phe Arg Cys Ser Phe Asn Arg Trp Thr His
        700                 705                 710 cgc ctg ggt cca ttg cca cct cag aaa atg tcg cct gct gaa aat ggc   2393
Arg Leu Gly Pro Leu Pro Pro Gln Lys Met Ser Pro Ala Glu Asn Gly
    715                 720                 725 acc cat gtc aga gca act gtg aag gtt cca ttg gat gca tat atg atg   2441
Thr His Val Arg Ala Thr Val Lys Val Pro Leu Asp Ala Tyr Met Met
730                 735                 740                 745 gat ttt gta ttt tcc gag aga gaa gat ggt ggg att ttt gac aat aag   2489
Asp Phe Val Phe Ser Glu Arg Glu Asp Gly Gly Ile Phe Asp Asn Lys
                750                 755                 760 agc gga atg gac tat cac ata cct gtg ttt gga gga gtc gct aaa gaa   2537
Ser Gly Met Asp Tyr His Ile Pro Val Phe Gly Gly Val Ala Lys Glu
            765                 770                 775 cct cca atg cat att gtc cat att gct gtc gaa atg gca cca att gca   2585
Pro Pro Met His Ile Val His Ile Ala Val Glu Met Ala Pro Ile Ala
        780                 785                 790 aag gtg gga ggc ctt ggt gat gtt gtt act agt ctt tcc cgt gct gtt   2633
Lys Val Gly Gly Leu Gly Asp Val Val Thr Ser Leu Ser Arg Ala Val
    795                 800                 805 caa gat tta aac cat aat gtg gat att atc tta cct aag tat gac tgt   2681
Gln Asp Leu Asn His Asn Val Asp Ile Ile Leu Pro Lys Tyr Asp Cys
810                 815                 820                 825 ttg aag atg aat aat gtg aag gac ttt cgg ttt cac aaa aac tac ttt   2729
Leu Lys Met Asn Asn Val Lys Asp Phe Arg Phe His Lys Asn Tyr Phe
                830                 835                 840 tgg ggt ggg act gaa ata aaa gta tgg ttt gga aag gtg gaa ggt ctc   2777
Trp Gly Gly Thr Glu Ile Lys Val Trp Phe Gly Lys Val Glu Gly Leu
            845                 850                 855 tcg gtc tat ttt ttg gag cct caa aac ggg tta ttt tcg aaa ggg tgc   2825
Ser Val Tyr Phe Leu Glu Pro Gln Asn Gly Leu Phe Ser Lys Gly Cys
        860                 865                 870
```

| | |
|---|---|
| gtc tat ggt tgt agc aat gat ggt gaa cga ttt ggt ttc ttc tgt cac<br>Val Tyr Gly Cys Ser Asn Asp Gly Glu Arg Phe Gly Phe Phe Cys His<br>875                     880                          885 | 2873 |
| gcg gct ttg gag ttt ctt ctg caa ggt gga ttt agt ccg gat atc att<br>Ala Ala Leu Glu Phe Leu Leu Gln Gly Gly Phe Ser Pro Asp Ile Ile<br>890                   895                       900                   905 | 2921 |
| cat tgc cat gat tgg tct agt gct cct gtt gct tgg ctc ttt aag gaa<br>His Cys His Asp Trp Ser Ser Ala Pro Val Ala Trp Leu Phe Lys Glu<br>910                           915                       920 | 2969 |
| caa tat aca cac tat ggt cta agc aaa tct cgt ata gtc ttc acg ata<br>Gln Tyr Thr His Tyr Gly Leu Ser Lys Ser Arg Ile Val Phe Thr Ile<br>                  925                       930                       935 | 3017 |
| cat aat ctt gaa ttt ggg gca gat ctc att ggg aga gca atg act aac<br>His Asn Leu Glu Phe Gly Ala Asp Leu Ile Gly Arg Ala Met Thr Asn<br>940                         945                        950 | 3065 |
| gca gac aaa gct aca aca gtt tca cca act tac tca cag gag gtg tct<br>Ala Asp Lys Ala Thr Thr Val Ser Pro Thr Tyr Ser Gln Glu Val Ser<br>      955                       960                       965 | 3113 |
| gga aac cct gta att gcg cct cac ctt cac aag ttc cat ggt ata gtg<br>Gly Asn Pro Val Ile Ala Pro His Leu His Lys Phe His Gly Ile Val<br>970                     975                       980                   985 | 3161 |
| aat ggg att gac cca gat att tgg gat cct tta aac gat aag ttc att<br>Asn Gly Ile Asp Pro Asp Ile Trp Asp Pro Leu Asn Asp Lys Phe Ile<br>                  990                       995                       1000 | 3209 |
| ccg att ccg tac acc tca gaa aac gtt gtt gaa ggc aaa aca gca<br>Pro Ile Pro Tyr Thr Ser Glu Asn Val Val Glu Gly Lys Thr Ala<br>                 1005                     1010                    1015 | 3254 |
| gcc aag gaa gct ttg cag cga aaa ctt gga ctg aaa cag gct gac<br>Ala Lys Glu Ala Leu Gln Arg Lys Leu Gly Leu Lys Gln Ala Asp<br>                 1020                     1025                    1030 | 3299 |
| ctt cct ttg gta gga att atc acc cgc tta act cac cag aaa gga<br>Leu Pro Leu Val Gly Ile Ile Thr Arg Leu Thr His Gln Lys Gly<br>                 1035                     1040                    1045 | 3344 |
| atc cac ctc att aaa cat gct att tgg cgc acc ttg gaa cgg aac<br>Ile His Leu Ile Lys His Ala Ile Trp Arg Thr Leu Glu Arg Asn<br>                 1050                     1055                    1060 | 3389 |
| gga cag gta gtc ttg ctt ggt tct gct cct gat cct agg gta caa<br>Gly Gln Val Val Leu Leu Gly Ser Ala Pro Asp Pro Arg Val Gln<br>                 1065                     1070                    1075 | 3434 |
| aac gat ttt gtt aat ttg gca aat caa ttg cac tcc aaa tat aat<br>Asn Asp Phe Val Asn Leu Ala Asn Gln Leu His Ser Lys Tyr Asn<br>                 1080                     1085                    1090 | 3479 |
| gac cgc gca cga ctc tgt cta aca tat gac gag cca ctt tct cac<br>Asp Arg Ala Arg Leu Cys Leu Thr Tyr Asp Glu Pro Leu Ser His<br>                 1095                     1100                    1105 | 3524 |
| ctg ata tat gct ggt gct gat ttt att cta gtt cct tca ata ttt<br>Leu Ile Tyr Ala Gly Ala Asp Phe Ile Leu Val Pro Ser Ile Phe<br>                 1110                     1115                    1120 | 3569 |
| gag cca tgt gga cta aca caa ctt acc gct atg aga tat ggt tca<br>Glu Pro Cys Gly Leu Thr Gln Leu Thr Ala Met Arg Tyr Gly Ser<br>                 1125                     1130                    1135 | 3614 |
| att cca gtc gtg cgt aaa act gga gga ctt tat gat act gta ttt<br>Ile Pro Val Val Arg Lys Thr Gly Gly Leu Tyr Asp Thr Val Phe<br>                 1140                     1145                    1150 | 3659 |
| gat gtt gac cat gac aaa gag aga gca caa cag tgt ggt ctt gaa<br>Asp Val Asp His Asp Lys Glu Arg Ala Gln Gln Cys Gly Leu Glu<br>                 1155                     1160                    1165 | 3704 |
| cca aat gga ttc agc ttt gat gga gca gat gct ggc gga gtt gat<br>Pro Asn Gly Phe Ser Phe Asp Gly Ala Asp Ala Gly Gly Val Asp<br>                 1170                     1175                    1180 | 3749 |

```
tat gct ctg aat aga gct ctc tct gct tgg tac gat ggt cgg gat      3794
Tyr Ala Leu Asn Arg Ala Leu Ser Ala Trp Tyr Asp Gly Arg Asp
            1185                1190                1195 tgg ttc aac tct tta tgc aag cag gtc atg gaa caa gat tgg tct      3839
Trp Phe Asn Ser Leu Cys Lys Gln Val Met Glu Gln Asp Trp Ser
            1200                1205                1210 tgg aac cga cct gct ctt gat tat ttg gag ctt tac cat gct gct      3884
Trp Asn Arg Pro Ala Leu Asp Tyr Leu Glu Leu Tyr His Ala Ala
            1215                1220                1225 aga aag tta gaa tag ttagtttgtg agatgctagc agaaaaattc acgagatctg  3939
Arg Lys Leu Glu
            1230 caatctgtac aggttcagtg tttgcgtctg gacagctttt ttatttccta tatcaaagta 3999 taaatcaagt ctacactgag atcaatagca gacagtcctc agttcatttc attttttgtg 4059 caacatatga aagagcttag cctctaataa tgtagtcatt gatgattatt tgttttggga 4119 agaaatgaga aatcaaagga tgcaaaatac tctgaaaaaa aaaaaaaa             4167

<210> SEQ ID NO 2
<211> LENGTH: 1230
<212> TYPE: PRT
<213> ORGANISM: Solanum tuberosum

<400> SEQUENCE: 2

Met Asp Val Pro Phe Pro Leu His Arg Pro Leu Ser Cys Thr Ser Val
1               5                   10                  15

Ser Asn Ala Ile Thr His Leu Lys Ile Lys Pro Phe Leu Gly Phe Val
            20                  25                  30

Ser His Gly Thr Thr Ser Leu Ser Val Gln Ser Ser Trp Arg Lys
        35                  40                  45

Asp Gly Met Val Thr Gly Val Ser Phe Pro Phe Cys Ala Asn Leu Ser
    50                  55                  60

Gly Arg Arg Arg Lys Val Ser Thr Thr Arg Ser Gln Gly Ser Ser
65                  70                  75                  80

Pro Lys Gly Phe Val Pro Arg Lys Pro Ser Gly Met Ser Thr Gln Arg
                85                  90                  95

Lys Val Gln Lys Ser Asn Gly Asp Lys Glu Ser Gln Ser Thr Ser Thr
            100                 105                 110

Ser Lys Glu Ser Glu Ile Ser Asn Gln Lys Thr Val Glu Ala Arg Val
        115                 120                 125

Glu Thr Ser Asp Asp Thr Lys Val Val Arg Asp His Lys Phe
    130                 135                 140

Leu Glu Asp Glu Asp Glu Ile Asn Gly Ser Thr Lys Ser Ile Ser Met
145                 150                 155                 160

Ser Pro Val Arg Val Ser Ser Gln Phe Val Glu Ser Glu Thr Gly
                165                 170                 175

Gly Asp Asp Lys Asp Ala Val Lys Leu Asn Lys Ser Lys Arg Ser Glu
            180                 185                 190

Glu Ser Asp Phe Leu Ile Asp Ser Val Ile Arg Glu Gln Ser Gly Ser
        195                 200                 205

Gln Gly Glu Thr Asn Ala Ser Ser Lys Gly Ser His Ala Val Gly Thr
    210                 215                 220

Lys Leu Tyr Glu Ile Leu Gln Val Asp Val Glu Pro Gln Gln Leu Lys
225                 230                 235                 240

Glu Asn Asn Ala Gly Asn Val Glu Tyr Lys Gly Pro Val Ala Ser Lys
                245                 250                 255
```

-continued

```
Leu Leu Glu Ile Thr Lys Ala Ser Asp Val Glu His Thr Glu Ser Asn
            260                 265                 270

Glu Ile Asp Asp Leu Asp Thr Asn Ser Phe Phe Lys Ser Asp Leu Ile
            275                 280                 285

Glu Glu Asp Glu Pro Leu Ala Ala Gly Thr Val Glu Thr Gly Asp Ser
            290                 295                 300

Ser Leu Asn Leu Arg Leu Glu Met Glu Ala Asn Leu Arg Arg Gln Ala
305                 310                 315                 320

Ile Glu Arg Leu Ala Glu Glu Asn Leu Leu Gln Gly Ile Arg Leu Phe
                325                 330                 335

Cys Phe Pro Glu Val Val Lys Pro Asp Glu Asp Val Glu Ile Phe Leu
            340                 345                 350

Asn Arg Gly Leu Ser Thr Leu Lys Asn Glu Ser Asp Val Leu Ile Met
            355                 360                 365

Gly Ala Phe Asn Glu Trp Arg Tyr Arg Ser Phe Thr Thr Arg Leu Thr
            370                 375                 380

Glu Thr His Leu Asn Gly Asp Trp Trp Ser Cys Lys Ile His Val Pro
385                 390                 395                 400

Lys Glu Ala Tyr Arg Ala Asp Phe Val Phe Asn Gly Gln Asp Val
                405                 410                 415

Tyr Asp Asn Asn Asp Gly Asn Asp Phe Ser Ile Thr Val Lys Gly Gly
            420                 425                 430

Met Gln Ile Ile Asp Phe Glu Asn Phe Leu Leu Glu Glu Lys Trp Arg
            435                 440                 445

Glu Gln Glu Lys Leu Ala Lys Glu Gln Ala Glu Arg Glu Arg Leu Ala
            450                 455                 460

Glu Glu Gln Arg Arg Ile Glu Ala Glu Lys Ala Glu Ile Glu Ala Asp
465                 470                 475                 480

Arg Ala Gln Ala Lys Glu Glu Ala Ala Lys Lys Lys Val Leu Arg
                485                 490                 495

Glu Leu Met Val Lys Ala Thr Lys Thr Arg Asp Ile Thr Trp Tyr Ile
            500                 505                 510

Glu Pro Ser Glu Phe Lys Cys Glu Asp Lys Val Arg Leu Tyr Tyr Asn
            515                 520                 525

Lys Ser Ser Gly Pro Leu Ser His Ala Lys Asp Leu Trp Ile His Gly
530                 535                 540

Gly Tyr Asn Asn Trp Lys Asp Gly Leu Ser Ile Val Lys Lys Leu Val
545                 550                 555                 560

Lys Ser Glu Arg Ile Asp Gly Asp Trp Trp Tyr Thr Glu Val Val Ile
                565                 570                 575

Pro Asp Gln Ala Leu Phe Leu Asp Trp Val Phe Ala Asp Gly Pro Pro
            580                 585                 590

Lys His Ala Ile Ala Tyr Asp Asn Asn His Arg Gln Asp Phe His Ala
            595                 600                 605

Ile Val Pro Asn His Ile Pro Glu Glu Leu Tyr Trp Val Glu Glu Glu
            610                 615                 620

His Gln Ile Phe Lys Thr Leu Gln Glu Glu Arg Arg Leu Arg Glu Ala
625                 630                 635                 640

Ala Met Arg Ala Lys Val Glu Lys Thr Ala Leu Leu Lys Thr Glu Thr
                645                 650                 655

Lys Glu Arg Thr Met Lys Ser Phe Leu Leu Ser Gln Lys His Val Val
            660                 665                 670

Tyr Thr Glu Pro Leu Asp Ile Gln Ala Gly Ser Ser Val Thr Val Tyr
            675                 680                 685
```

```
Tyr Asn Pro Ala Asn Thr Val Leu Asn Gly Lys Pro Glu Ile Trp Phe
    690             695                 700

Arg Cys Ser Phe Asn Arg Trp Thr His Arg Leu Gly Pro Leu Pro Pro
705             710                 715                 720

Gln Lys Met Ser Pro Ala Glu Asn Gly Thr His Val Arg Ala Thr Val
        725                 730                 735

Lys Val Pro Leu Asp Ala Tyr Met Met Asp Phe Val Phe Ser Glu Arg
            740                 745                 750

Glu Asp Gly Gly Ile Phe Asp Asn Lys Ser Gly Met Asp Tyr His Ile
                755                 760                 765

Pro Val Phe Gly Gly Val Ala Lys Glu Pro Pro Met His Ile Val His
770                 775                 780

Ile Ala Val Glu Met Ala Pro Ile Ala Lys Val Gly Gly Leu Gly Asp
785                 790                 795                 800

Val Val Thr Ser Leu Ser Arg Ala Val Gln Asp Leu Asn His Asn Val
                805                 810                 815

Asp Ile Ile Leu Pro Lys Tyr Asp Cys Leu Lys Met Asn Asn Val Lys
                820                 825                 830

Asp Phe Arg Phe His Lys Asn Tyr Phe Trp Gly Gly Thr Glu Ile Lys
            835                 840                 845

Val Trp Phe Gly Lys Val Glu Gly Leu Ser Val Tyr Phe Leu Glu Pro
850                 855                 860

Gln Asn Gly Leu Phe Ser Lys Gly Cys Val Tyr Gly Cys Ser Asn Asp
865                 870                 875                 880

Gly Glu Arg Phe Gly Phe Phe Cys His Ala Ala Leu Glu Phe Leu Leu
            885                 890                 895

Gln Gly Gly Phe Ser Pro Asp Ile Ile His Cys His Asp Trp Ser Ser
                900                 905                 910

Ala Pro Val Ala Trp Leu Phe Lys Glu Gln Tyr Thr His Tyr Gly Leu
            915                 920                 925

Ser Lys Ser Arg Ile Val Phe Thr Ile His Asn Leu Glu Phe Gly Ala
    930                 935                 940

Asp Leu Ile Gly Arg Ala Met Thr Asn Ala Asp Lys Ala Thr Thr Val
945                 950                 955                 960

Ser Pro Thr Tyr Ser Gln Glu Val Ser Gly Asn Pro Val Ile Ala Pro
                965                 970                 975

His Leu His Lys Phe His Gly Ile Val Asn Gly Ile Asp Pro Asp Ile
            980                 985                 990

Trp Asp Pro Leu Asn Asp Lys Phe Ile Pro Ile Pro Tyr Thr Ser Glu
        995                 1000                1005

Asn Val Val Glu Gly Lys Thr Ala Ala Lys Glu Ala Leu Gln Arg
    1010                1015                1020

Lys Leu Gly Leu Lys Gln Ala Asp Leu Pro Leu Val Gly Ile Ile
    1025                1030                1035

Thr Arg Leu Thr His Gln Lys Gly Ile His Leu Ile Lys His Ala
    1040                1045                1050

Ile Trp Arg Thr Leu Glu Arg Asn Gly Gln Val Val Leu Leu Gly
    1055                1060                1065

Ser Ala Pro Asp Pro Arg Val Gln Asn Asp Phe Val Asn Leu Ala
    1070                1075                1080

Asn Gln Leu His Ser Lys Tyr Asn Asp Arg Ala Arg Leu Cys Leu
    1085                1090                1095

Thr Tyr Asp Glu Pro Leu Ser His Leu Ile Tyr Ala Gly Ala Asp
```

```
                  1100              1105              1110
Phe Ile Leu Val Pro Ser Ile Phe Glu Pro Cys Gly Leu Thr Gln
        1115              1120              1125
Leu Thr Ala Met Arg Tyr Gly Ser Ile Pro Val Val Arg Lys Thr
        1130              1135              1140
Gly Gly Leu Tyr Asp Thr Val Phe Asp Val Asp His Asp Lys Glu
        1145              1150              1155
Arg Ala Gln Gln Cys Gly Leu Glu Pro Asn Gly Phe Ser Phe Asp
        1160              1165              1170
Gly Ala Asp Ala Gly Gly Val Asp Tyr Ala Leu Asn Arg Ala Leu
        1175              1180              1185
Ser Ala Trp Tyr Asp Gly Arg Asp Trp Phe Asn Ser Leu Cys Lys
        1190              1195              1200
Gln Val Met Glu Gln Asp Trp Ser Trp Asn Arg Pro Ala Leu Asp
        1205              1210              1215
Tyr Leu Glu Leu Tyr His Ala Ala Arg Lys Leu Glu
        1220              1225              1230

<210> SEQ ID NO 3
<211> LENGTH: 61
<212> TYPE: PRT
<213> ORGANISM: Solanum tuberosum

<400> SEQUENCE: 3

Arg Ser Phe Thr Thr Arg Leu Thr Glu Thr His Leu Asn Gly Asp Trp
1               5                   10                  15
Trp Ser Cys Lys Ile His Val Pro Lys Glu Ala Tyr Arg Ala Asp Phe
            20                  25                  30
Val Phe Phe Asn Gly Gln Asp Val Tyr Asp Asn Asn Asp Gly Asn Asp
        35                  40                  45
Phe Ser Ile Thr Val Lys Gly Gly Met Gln Ile Ile Asp
    50                  55                  60

<210> SEQ ID NO 4
<211> LENGTH: 1641
<212> TYPE: DNA
<213> ORGANISM: Solanum tuberosum

<400> SEQUENCE: 4
atgaagcaca gttcagctat ttccgctgtt ttgaccgatg acaattcgac aatggcaccc      60
ctagaggaag atgtcaacac tgaaaatatt ggcctcctaa atttggatcc aactttggaa     120
ccttatctag atcacttcag acacagaatg aagagatatg tggatcagaa aatgctcatt     180
gaaaaatatg agggaccccct tgaggaattt gctcaaggtt atttaaaatt tggattcaac    240
agggaagatg gttgcatagt ctatcgtgaa tgggctcctg ctgctcagga agcagaagtt     300
attggcgatt caatggtag gaacggttct aaccacatga tggagaagga ccagtttggt      360
gtttggagta ttagaattcc tgatgttgac agtaagccag tcattccaca caactccaga     420
gttaagtttc gttcaaaca tggtaatgga gtgtgggtag atcgtatccc tgcttggata      480
aagtatgcca ctgcagacgc cacaaagttt gcagcaccat atgatggtgt ctactgggac    540
ccaccacctt cagaaaggta ccacttcaaa taccctcgcc ctcccaaacc ccgaccccca    600
cgaatctacg aagcacatgt cggcatgagc agctctgagc acgtgtaaa ttcgtatcgt     660 gagtttgcag atgatgtttt acctcggatt aaggcaaata actataatac tgtccagttg    720
atggccataa tggaacattc ttactatgga tcatttggat atcatgttac aaactttttt    780
```

-continued

```
gctgtgagca atagatatgg aaacccggag gacctaaagt atctgataga taaagcacat    840
agcttgggtt tacaggttct ggtggatgta gttcacagtc atgcaagcaa taatgtcact    900
gatggcctca atggctttga tattggccaa ggttctcaag aatcctactt tcatgctgga    960
gagcgagggt accataagtt gtgggatagc aggctgttca actatgccaa ttgggaggtt   1020
cttcgtttcc ttctttccaa cttgaggtgg tggctagaag agtataactt tgacggattt   1080
cgatttgatg gaataacttc tatgctgtat gttcatcatg gaatcaatat gggatttaca   1140
ggaaactata atgagtattt cagcgaggct acagatgttg atgctgtggt ctatttaatg   1200
ttggccaata atctgattca aagattttc ccagacgcaa ctgttattgc cgaagatgtt   1260
tctggtatgc cgggccttag ccggcctgtt tctgagggag gaattggttt tgattaccgc   1320
ctggcaatgg caatcccaga taagtggata gattatttaa agaataagaa tgatgaagat   1380
tggtccatga aggaagtaac atcgagtttg acaaatagga gatatacaga gaagtgtata   1440
gcatatgcgg agagccatga tcagtctatt gtcggtgaca agaccattgc atttctccta   1500
atgaacaaag agatgtattc tggcatgtct tgcttgacag atgcttctcc tgttgttgat   1560
gcaggaattg cgcttgacaa gatgatccat tttttttcaca atggccttgg gaggagaggg   1620
gtacctcaat ttcatgggta a                                             1641
```

<210> SEQ ID NO 5
<211> LENGTH: 546
<212> TYPE: PRT
<213> ORGANISM: Solanum tuberosum
<300> PUBLICATION INFORMATION:
<308> DATABASE ACCESSION NUMBER: Swiss Prot / P30924
<309> DATABASE ENTRY DATE: 1993-07-26

<400> SEQUENCE: 5

```
Met Lys His Ser Ser Ala Ile Ser Ala Val Leu Thr Asp Asp Asn Ser
1               5                   10                  15

Thr Met Ala Pro Leu Glu Glu Asp Val Asn Thr Glu Asn Ile Gly Leu
            20                  25                  30

Leu Asn Leu Asp Pro Thr Leu Glu Pro Tyr Leu Asp His Phe Arg His
        35                  40                  45

Arg Met Lys Arg Tyr Val Asp Gln Lys Met Leu Ile Glu Lys Tyr Glu
    50                  55                  60

Gly Pro Leu Glu Glu Phe Ala Gln Gly Tyr Leu Lys Phe Gly Phe Asn
65                  70                  75                  80

Arg Glu Asp Gly Cys Ile Val Tyr Arg Glu Trp Ala Pro Ala Ala Gln
                85                  90                  95

Glu Ala Glu Val Ile Gly Asp Phe Asn Gly Arg Asn Gly Ser Asn His
            100                 105                 110

Met Met Glu Lys Asp Gln Phe Gly Val Trp Ser Ile Arg Ile Pro Asp
        115                 120                 125

Val Asp Ser Lys Pro Val Ile Pro His Asn Ser Arg Val Lys Phe Arg
    130                 135                 140

Phe Lys His Gly Asn Gly Val Trp Val Asp Arg Ile Pro Ala Trp Ile
145                 150                 155                 160

Lys Tyr Ala Thr Ala Asp Ala Thr Lys Phe Ala Ala Pro Tyr Asp Gly
                165                 170                 175

Val Tyr Trp Asp Pro Pro Pro Ser Glu Arg Tyr His Phe Lys Tyr Pro
            180                 185                 190

Arg Pro Pro Lys Pro Arg Ala Pro Arg Ile Tyr Glu Ala His Val Gly
        195                 200                 205
```

```
Met Ser Ser Ser Glu Pro Arg Val Asn Ser Tyr Arg Glu Phe Ala Asp
        210                 215                 220

Asp Val Leu Pro Arg Ile Lys Ala Asn Asn Tyr Asn Thr Val Gln Leu
225                 230                 235                 240

Met Ala Ile Met Glu His Ser Tyr Tyr Gly Ser Phe Gly Tyr His Val
            245                 250                 255

Thr Asn Phe Phe Ala Val Ser Asn Arg Tyr Gly Asn Pro Glu Asp Leu
                260                 265                 270

Lys Tyr Leu Ile Asp Lys Ala His Ser Leu Gly Leu Gln Val Leu Val
            275                 280                 285

Asp Val His Ser His Ala Ser Asn Asn Val Thr Asp Gly Leu Asn
290                 295                 300

Gly Phe Asp Ile Gly Gln Gly Ser Gln Glu Ser Tyr Phe His Ala Gly
305                 310                 315                 320

Glu Arg Gly Tyr His Lys Leu Trp Asp Ser Arg Leu Phe Asn Tyr Ala
                325                 330                 335

Asn Trp Glu Val Leu Arg Phe Leu Leu Ser Asn Leu Arg Trp Trp Leu
                340                 345                 350

Glu Glu Tyr Asn Phe Asp Gly Phe Arg Phe Asp Gly Ile Thr Ser Met
            355                 360                 365

Leu Tyr Val His His Gly Ile Asn Met Gly Phe Thr Gly Asn Tyr Asn
370                 375                 380

Glu Tyr Phe Ser Glu Ala Thr Asp Val Asp Ala Val Val Tyr Leu Met
385                 390                 395                 400

Leu Ala Asn Asn Leu Ile His Lys Ile Phe Pro Asp Ala Thr Val Ile
                405                 410                 415

Ala Glu Asp Val Ser Gly Met Pro Gly Leu Ser Arg Pro Val Ser Glu
            420                 425                 430

Gly Gly Ile Gly Phe Asp Tyr Arg Leu Ala Met Ala Ile Pro Asp Lys
            435                 440                 445

Trp Ile Asp Tyr Leu Lys Asn Lys Asn Asp Glu Asp Trp Ser Met Lys
            450                 455                 460

Glu Val Thr Ser Ser Leu Thr Asn Arg Arg Tyr Thr Glu Lys Cys Ile
465                 470                 475                 480

Ala Tyr Ala Glu Ser His Asp Gln Ser Ile Val Gly Asp Lys Thr Ile
                485                 490                 495

Ala Phe Leu Leu Met Asn Lys Glu Met Tyr Ser Gly Met Ser Cys Leu
                500                 505                 510

Thr Asp Ala Ser Pro Val Val Asp Ala Gly Ile Ala Leu Asp Lys Met
            515                 520                 525

Ile His Phe Phe His Asn Gly Leu Gly Arg Arg Gly Val Pro Gln Phe
530                 535                 540

His Gly
545

<210> SEQ ID NO 6
<211> LENGTH: 2649
<212> TYPE: DNA
<213> ORGANISM: Solanum tuberosum
<300> PUBLICATION INFORMATION:
<308> DATABASE ACCESSION NUMBER: EMBL / AJ011890
<309> DATABASE ENTRY DATE: 1999-04-07
<300> PUBLICATION INFORMATION:
<302> TITLE: Improvments in or relating to plant starch composition
<308> DATABASE ACCESSION NUMBER: EMBL / A58164
<309> DATABASE ENTRY DATE: 1998-03-05
<310> PATENT DOCUMENT NUMBER: WO 96 34968
<311> PATENT FILING DATE: 1996-05-03
```

<312> PUBLICATION DATE: 1996-11-07

<400> SEQUENCE: 6

```
atggtgtata cactctctgg agttcgtttt cctactgttc catcagtgta caaatctaat      60
ggattcagca gtaatggtga tcggaggaat gctaatgttt ctgtattctt gaaaaagcac     120
tctcttttcac ggaagatctt ggctgaaaag tcttcttaca attccgaatt ccgaccttct    180
acagttgcag catcggggaa agtccttgtg cctggaaccc agagtgatag ctcctcatcc     240
tcaacagacc aatttgagtt cactgagaca tctccagaaa attccccagc atcaactgat    300
gtagatagtt caacaatgga acacgctagc cagattaaaa ctgagaacga tgacgttgag    360
ccgtcaagtg atcttacagg aagtgttgaa gagctggatt ttgcttcatc actacaacta    420
caagaaggtg taaactgga ggagtctaaa acattaaata cttctgaaga gacaattatt     480
gatgaatctg ataggatcag agagagggc atccctccac ctggacttgg tcagaagatt     540
tatgaaatag accccctttt gacaaactat cgtcaacacc ttgattacag gtattcacag    600
tacaagaaac tgagggaggc aattgacaag tatgagggtg gtttggaagc cttttctcgt    660
ggttatgaaa aatgggtttt cactcgtagt gctacaggta tcacttaccg tgagtgggct    720
cttggtgccc agtcagctgc cctcattgga gatttcaaca attgggacgc aaatgctgac    780
attatgactc ggaatgaatt tggtgtctgg gagattttc tgccaaataa tgtggatggt    840
tctcctgcaa ttcctcatgg gtccagagtg aagatacgta tggacactcc atcaggtgtt    900
aaggattcca ttcctgcttg gatcaactac tctttacagc ttcctgatga aattccatat    960
aatggaatac attatgatcc acccgaagag gagaggtata tcttccaaca cccacggcca   1020
aagaaaccaa gtcgctgag aatatatgaa tctcatattg gaatgagtag tccggagcct   1080
aaaattaact catacgtgaa ttttagagat gaagttcttc ctcgcataaa aaagcttggg   1140
tacaatgcgc tgcaaattat ggctattcaa gagcattctt attacgctag ttttggttat   1200
catgtcacaa atttttttgc accaagcagc cgttttggaa cgcccgacga ccttaagtct   1260
ttgattgata agctcatgaa gctaggaatt gttgttctca tggacattgt tcacagccat   1320
gcatcaaata atactttaga tggactgaac atgtttgact gcaccgatag ttgttacttt   1380
cactctggag ctcgtggtta tcattggatg tgggattccc gcctctttaa ctatggaaac   1440
tgggaggtac ttaggtatct tctctcaaat gcgagatggt ggttggatgc gttcaaattt   1500
gatggattta gatttgatgg tgtgacatca atgatgtata ttcaccacgg attatcggtg   1560
ggattcactg gaactacga ggaatacttt ggactcgcaa ctgatgtgga tgctgttgtg   1620
tatctgatgc tggtcaacga tcttattcat gggcttttcc cagatgcaat taccattggt   1680
gaagatgtta gcggaatgcc gacattttgt attcccgtcc aagagggggg tgttggcttt   1740
gactatcggc tgcatatggc aattgctgat aaacggattg agttgctcaa gaaacgggat   1800
gaggattgga gagtgggtga tattgttcat acactgacaa atagaagatg gtcggaaaag   1860
tgtgtttcat acgctgaaag tcatgatcaa gctctagtcg gtgataaaac tatagcattc   1920
tggctgatgg acaaggatat gtatgatttt atggctctgg atagaccgtc aacatcatta   1980
atagatcgtg ggatagcatt gcacaagatg attaggcttg taactatggg attaggagga   2040
gaagggtacc taaatttcat gggaaatgaa ttcggccacc ctgagtggat tgatttccct   2100
agggctgaac aacacctctc tgatggctca gtaatcccg aaaccaatt ccgttatgat    2160
aaatgcagac ggagatttga cctgggagat gcagaatatt taagataccg tgggttgcaa   2220
gaatttgacc ggcctatgca gtatcttgaa gataaatatg agtttatgac ttcagaacac   2280
```

```
cagttcatat cacgaaagga tgaaggagat aggatgattg tatttgaaaa aggaaaccta    2340 gttttttgtct ttaattttca ctggacaaaa agctattcag actatcgcat agcctgcctg    2400
aagcctggaa atacccggt tgccttggac tcagatgatc cacttttttgg tggcttcggg     2460 agaattgatc ataatgccga atatttcacc tttgaaggat ggtatgatga tcgtcctcgt    2520
tcaattatgg tgtatgcacc ttgtaaaaca gcagtggtct atgcactagt agacaaagaa    2580
gaagaagaag aagaagaaga agaagaagaa gtagcagcag tagaagaagt agtagtagaa    2640
gaagaatga                                                            2649
```

<210> SEQ ID NO 7
<211> LENGTH: 882
<212> TYPE: PRT
<213> ORGANISM: Solanum tuberosum

<400> SEQUENCE: 7

```
Met Val Tyr Thr Leu Ser Gly Val Arg Phe Pro Thr Val Pro Ser Val
1               5                   10                  15

Tyr Lys Ser Asn Gly Phe Ser Ser Asn Gly Asp Arg Arg Asn Ala Asn
            20                  25                  30

Val Ser Val Phe Leu Lys Lys His Ser Leu Ser Arg Lys Ile Leu Ala
        35                  40                  45

Glu Lys Ser Ser Tyr Asn Ser Glu Phe Arg Pro Ser Thr Val Ala Ala
    50                  55                  60

Ser Gly Lys Val Leu Val Pro Gly Thr Gln Ser Asp Ser Ser Ser
65                  70                  75                  80

Ser Thr Asp Gln Phe Glu Phe Thr Glu Thr Ser Pro Glu Asn Ser Pro
                85                  90                  95

Ala Ser Thr Asp Val Asp Ser Ser Thr Met Glu His Ala Ser Gln Ile
            100                 105                 110

Lys Thr Glu Asn Asp Asp Val Glu Pro Ser Ser Asp Leu Thr Gly Ser
        115                 120                 125

Val Glu Glu Leu Asp Phe Ala Ser Ser Leu Gln Leu Gln Glu Gly Gly
    130                 135                 140

Lys Leu Glu Glu Ser Lys Thr Leu Asn Thr Ser Glu Glu Thr Ile Ile
145                 150                 155                 160

Asp Glu Ser Asp Arg Ile Arg Glu Arg Gly Ile Pro Pro Gly Leu
                165                 170                 175

Gly Gln Lys Ile Tyr Glu Ile Asp Pro Leu Leu Thr Asn Tyr Arg Gln
            180                 185                 190

His Leu Asp Tyr Arg Tyr Ser Gln Tyr Lys Lys Leu Arg Glu Ala Ile
        195                 200                 205

Asp Lys Tyr Glu Gly Gly Leu Glu Ala Phe Ser Arg Gly Tyr Glu Lys
    210                 215                 220

Met Gly Phe Thr Arg Ser Ala Thr Gly Ile Thr Tyr Arg Glu Trp Ala
225                 230                 235                 240

Leu Gly Ala Gln Ser Ala Ala Leu Ile Gly Asp Phe Asn Asn Trp Asp
                245                 250                 255

Ala Asn Ala Asp Ile Met Thr Arg Asn Glu Phe Gly Val Trp Glu Ile
            260                 265                 270

Phe Leu Pro Asn Asn Val Asp Gly Ser Pro Ala Ile Pro His Gly Ser
        275                 280                 285

Arg Val Lys Ile Arg Met Asp Thr Pro Ser Gly Val Lys Asp Ser Ile
    290                 295                 300

Pro Ala Trp Ile Asn Tyr Ser Leu Gln Leu Pro Asp Glu Ile Pro Tyr
```

```
            305                 310                 315                 320
Asn Gly Ile His Tyr Asp Pro Pro Glu Glu Arg Tyr Ile Phe Gln
                325                 330                 335
His Pro Arg Pro Lys Lys Pro Lys Ser Leu Arg Ile Tyr Glu Ser His
                340                 345                 350
Ile Gly Met Ser Ser Pro Glu Pro Lys Ile Asn Ser Tyr Val Asn Phe
                355                 360                 365
Arg Asp Glu Val Leu Pro Arg Ile Lys Lys Leu Gly Tyr Asn Ala Leu
            370                 375                 380
Gln Ile Met Ala Ile Gln Glu His Ser Tyr Tyr Ala Ser Phe Gly Tyr
385                 390                 395                 400
His Val Thr Asn Phe Phe Ala Pro Ser Ser Arg Phe Gly Thr Pro Asp
                405                 410                 415
Asp Leu Lys Ser Leu Ile Asp Lys Ala His Glu Leu Gly Ile Val Val
                420                 425                 430
Leu Met Asp Ile Val His Ser His Ala Ser Asn Asn Thr Leu Asp Gly
                435                 440                 445
Leu Asn Met Phe Asp Cys Thr Asp Ser Cys Tyr Phe His Ser Gly Ala
            450                 455                 460
Arg Gly Tyr His Trp Met Trp Asp Ser Arg Leu Phe Asn Tyr Gly Asn
465                 470                 475                 480
Trp Glu Val Leu Arg Tyr Leu Leu Ser Asn Ala Arg Trp Trp Leu Asp
                485                 490                 495
Ala Phe Lys Phe Asp Gly Phe Arg Phe Asp Gly Val Thr Ser Met Met
                500                 505                 510
Tyr Ile His His Gly Leu Ser Val Gly Phe Thr Gly Asn Tyr Glu Glu
                515                 520                 525
Tyr Phe Gly Leu Ala Thr Asp Val Asp Ala Val Val Tyr Leu Met Leu
            530                 535                 540
Val Asn Asp Leu Ile His Gly Leu Phe Pro Asp Ala Ile Thr Ile Gly
545                 550                 555                 560
Glu Asp Val Ser Gly Met Pro Thr Phe Cys Ile Pro Val Gln Glu Gly
                565                 570                 575
Gly Val Gly Phe Asp Tyr Arg Leu His Met Ala Ile Ala Asp Lys Arg
                580                 585                 590
Ile Glu Leu Leu Lys Lys Arg Asp Glu Asp Trp Arg Val Gly Asp Ile
            595                 600                 605
Val His Thr Leu Thr Asn Arg Arg Trp Ser Glu Lys Cys Val Ser Tyr
            610                 615                 620
Ala Glu Ser His Asp Gln Ala Leu Val Gly Asp Lys Thr Ile Ala Phe
625                 630                 635                 640
Trp Leu Met Asp Lys Asp Met Tyr Asp Phe Met Ala Leu Asp Arg Pro
                645                 650                 655
Ser Thr Ser Leu Ile Asp Arg Gly Ile Ala Leu His Lys Met Ile Arg
                660                 665                 670
Leu Val Thr Met Gly Leu Gly Gly Glu Gly Tyr Leu Asn Phe Met Gly
                675                 680                 685
Asn Glu Phe Gly His Pro Glu Trp Ile Asp Phe Pro Arg Ala Glu Gln
                690                 695                 700
His Leu Ser Asp Gly Ser Val Ile Pro Gly Asn Gln Phe Arg Tyr Asp
705                 710                 715                 720
Lys Cys Arg Arg Arg Phe Asp Leu Gly Asp Ala Glu Tyr Leu Arg Tyr
                725                 730                 735
```

```
Arg Gly Leu Gln Glu Phe Asp Arg Pro Met Gln Tyr Leu Glu Asp Lys
                740                 745                 750

Tyr Glu Phe Met Thr Ser Glu His Gln Phe Ile Ser Arg Lys Asp Glu
        755                 760                 765

Gly Asp Arg Met Ile Val Phe Glu Lys Gly Asn Leu Val Phe Val Phe
    770                 775                 780

Asn Phe His Trp Thr Lys Ser Tyr Ser Asp Tyr Arg Ile Ala Cys Leu
785                 790                 795                 800

Lys Pro Gly Lys Tyr Pro Val Ala Leu Asp Ser Asp Pro Leu Phe
                805                 810                 815

Gly Gly Phe Gly Arg Ile Asp His Asn Ala Glu Tyr Phe Thr Phe Glu
                820                 825                 830

Gly Trp Tyr Asp Asp Arg Pro Arg Ser Ile Met Val Tyr Ala Pro Cys
    835                 840                 845

Lys Thr Ala Val Val Tyr Ala Leu Val Asp Lys Glu Glu Glu Glu Glu
                850                 855                 860

Glu Glu Glu Glu Glu Glu Val Ala Ala Val Glu Val Val Val Glu
865                 870                 875                 880

Glu Glu

<210> SEQ ID NO 8
<211> LENGTH: 1255
<212> TYPE: DNA
<213> ORGANISM: Solanum tuberosum

<400> SEQUENCE: 8
attttgtatt cccgttcaag atgggggtgt ggctttgac tatcggctgc atatggcaat      60
tgctgataaa tggattgagt tgctcaagaa acgggatgag gattggagag tgggtgatat     120
tgttcataca ctgacaaata aagatggtc ggaaaagtgt gtttcatacg ctgaaagtca      180
tgatcaagct ctagtcggtg ataaaactat agcattctgg ctgatggaca aggatatgta     240
tgattttatg gctttggata gaccgtcaac atcattaata gatcgtggga tagcattgca     300
caagatgatt aggcttgtaa ctatgggatt aggaggagaa gggtacctaa atttcatggg     360
aaatgaattc ggccacccotg agtggattga tttccctagg gctgaacaac acctctctga     420
tggctcagta attcccggaa accaattcag ttatgataaa tgcagacgga gatttgacct     480
gggagatgca gaatattaa ataccgtgg gttgcaagaa tttgaccggg ctatgcagta      540
tcttgaagat aaatatgagt ttatgacttc agaacaccag ttcatatcac gaaaggatga     600
aggagatagg atgattgtat tgaaaaagg aaacctagtt tttgtcttta atttcactg      660
gacaaaaagc tattcagact atcgcatagg ctgcctgaag cctggaaaat acaaggttgc     720
cttggactca gatgatccac tttttggtgg cttcgggaga attgatcata atgccgaatg     780
tttccacctt gaaggatggt atgatgatcg tcctcgttca attatggtgt atgcacctag     840
tagaacagca gtggtctatg cactagtaga caaagaagaa gaagaagaag aagtagcagt     900
agtagaagaa gtagtagtag aagaagaatg aacgaacttg tgatcgcgtt gaaagatttg     960
aacgctacat agagcttctt gacgtatctg gcaatattgc atcagtcttg gcggaatttc    1020
atgtgacaaa aggtttgcaa ttcttttccac tattagtagt gcaacgatat acgcagagat    1080
gaagtgctga acaaacatat gtaaaatcga tgaatttatg tcgaatgctg gacgggctt      1140
cagcaggttt tgcttagtga gttctgtaaa ttgtcatctc tttatatgta cagccaacta    1200
gaaatcaatt atgtgagacc taaaatacaa taaccataaa atggaaatag tgctg          1255
```

```
<210> SEQ ID NO 9
<211> LENGTH: 20
<212> TYPE: DNA
<213> ORGANISM: Artificial Sequence
<220> FEATURE:
<223> OTHER INFORMATION: PCR Primer

<400> SEQUENCE: 9
gggggtgttg gctttgacta                                              20

<210> SEQ ID NO 10
<211> LENGTH: 20
<212> TYPE: DNA
<213> ORGANISM: Artificial Sequence
<220> FEATURE:
<223> OTHER INFORMATION: PCR Primer

<400> SEQUENCE: 10
cccttctcct cctaatccca                                              20
```

PLANT CELLS AND PLANTS WHICH SYNTHESIZE A STARCH WITH AN INCREASED FINAL VISCOSITY

CROSS-REFERENCE TO RELATED APPLICATIONS

This application is a divisional of U.S. patent application Ser. No. 10/539,723, filed Jun. 20, 2005, now U.S. Pat. No. 7,714,186 which is the U.S. National Stage Application of International Application PCT/EP/03/014840, filed Dec. 19, 2003, which claims benefit of EP 02028530.0, filed Dec. 19, 2002, and EP 03090275.3, filed Aug. 29, 2003.

DESCRIPTION

The present invention relates to plant cells and plants which are genetically modified, the genetic modification leading to the reduction of the activity of SSIII and BEI and BEII proteins in comparison with corresponding plant cells, of wild-type plants, which have not been genetically modified. Furthermore, the present invention relates to means and methods for the generation of such plant cells and plants. Such plant cells and plants synthesize a modified starch which is characterized in that it has an amylose content of at least 30% and a phosphate content which is increased in comparison with starch from corresponding wild-type plants which have not been genetically modified and which have a final viscosity in the RVA analysis which is increased over the prior art and/or a modified side-chain distribution and/or an increased gel strength in the Texture Analyser and/or a modified granule morphology and/or a modified mean granule size. The present invention thus also relates to the starch synthesized by the plant cells and plants according to the invention, and to methods for producing this starch.

In view of the increasing importance which is currently attached to plant constituents as renewable raw materials, one of the tasks of biotechnology research is to attempt an adaptation of these vegetable raw materials to the requirements of the processing industry. In order to make possible the use of renewable raw materials in as many fields of application as possible, it is additionally necessary to arrive at very diverse substances.

The polysaccharide starch is a polymer of chemically uniform units, the glucose molecules. However, it takes the form of a highly complex mixture of different forms of molecules which differ with regard to their degree of polymerization and the occurrence of branches of the glucose chains. Starch is therefore no uniform raw material. One distinguishes between two chemically different components of starch, amylose and amylopectin. In typical plants used for starch production such as, for example, maize, wheat or potato, amylose starch accounts for approximately 20%-30% and amylopectin starch for approximately 70%-80% of the starch synthesized. Amylose has long been regarded as a linear polymer consisting of α-1,4-glycosidically linked α-D-glucose monomers. However, more recent studies have demonstrated the presence of α-1,6-glycosidic branch points (approx. 0.1%) (Hizukuri and Takagi, Carbohydr. Res. 134, (1984), 1-10; Takeda et al., Carbohydr. Res. 132, (1984), 83-92).

Various methods are available for determining the amylose content. Some of these methods are based on the iodine-binding capacity of amylose, which can determine potentiometrically (Banks & Greenwood, in W. Banks & C. T. Greenwood, Starch and its components (pp. 51-66), Edinburgh, Edinburgh University Press), amperometrically (Larson et al., Analytical Chemistry 25(5), (1953), 802-804) or spectrophotometrically (Morrison & Laignelet, J. Cereal Sc. 1, (1983), 9-20). The amylose content may also be determined calorimetrically by means of DSC (differential scanning calorimetry) measurements (Kugimiya & Donovan, Journal of Food Science 46, (1981), 765-770; Sievert & Holm, Starch/Stärke 45 (4), (1993), 136-139). It is furthermore possible to determine the amylose content via the use of SEC (size exclusion chromatography) chromatography of native or debranched starch. This method has been recommended in particular for determining the amylose content of genetically modified starches (Gérard et al., Carbohydrate Polymers 44, (2001), 19-27).

In contrast to amylose, amylopectin shows a higher degree of branching and has approximately 4% of branch points brought about by the occurrence of additional α-1,6-glycosidic linkages. Amylopectin constitutes a complex mixture of glucose chains with different branching patterns.

Another important difference between amylose and amylopectin is their molecular weight. While amylose, depending on the origin of the starch, has a molecular weight of $5 \times 10^5$-$10^6$ Da, the molecular weight of amylopectin is between $10^7$ and $10^8$ Da. The two macromolecules can be distinguished on the basis of their molecular weight and their different physico-chemical properties, and the simplest way of visualizing this is through their different iodine-binding properties.

In addition to the amylose/amylopectin ratio and the phosphate content, the functional properties of starch are affected greatly by the molecular weight, the side-chain distribution pattern, the ionic content, the lipid and protein content, the mean granule size and the granule morphology and the like. Important functional properties which may be mentioned in this context are solubility, the retrogradation behaviour, the water-binding capacity, the film-forming properties, viscosity, the gelatinization properties, freeze-thaw-stability, acid stability, gel strength and the like. Granule size may also be of importance for various applications.

The skilled workers frequently resort to different methods to determine the gelatinization properties, one of which is the final viscosity. Depending on the method used, absolute values in particular, but also relative values, may differ between one and the same starch sample. A rapid and effective method for analysing the gelatinization properties is the RVA analysis. Depending on the choice of the parameters and the temperature profile in the RVA analysis, different RVA profiles are obtained for one and the same sample. It should be mentioned that in some cases different profiles were used in the prior art mentioned hereinbelow when determining the gelatinization properties.

An overview over different plant species with a reduction of the enzymes participating in starch biosynthesis can be found in Kossmann and Lloyd (2000, Critical Reviews in Plant Sciences 19(3), 171-126).

To date, plants have been described in which the activity of an SSIII protein (Abel et al., 1996, The Plant Journal 10(6), 981-991; Lloyd et al., 1999, Biochemical Journal 338, 515-521) or the activity of a BEI protein (Kossman et al. 1991, Mol Gen Genet 230, 39-44); Safford et al., 1998, Carbohydrate Polymers 35, 155-168, or the activity of a BEII protein (Jobling et al., 1999, The Plant Journal 18(2): 163-171, or the activity of a BEI and a BEII protein (Schwall et al., 2000, Nature Biotechnology 18, 551-554; WO 96/34968), or the activity of a BEI and an SSIII (WO 00/08184) protein are reduced.

In plants in which the activity of an SSIII protein is reduced, a relative shift of the amylopectin side chains from longer chains towards shorter chains (Lloyd et al., 1999, Biochemical Journal 338, 515-521), a 70% higher phosphate content, no changes in the amylose content (Abel et al., 1996, The Plant Journal 10(6), 9891-991) and a reduced final viscosity in the RVA analysis (Abel, 1995, PhD Thesis at the Freie Universität Berlin) are observed in comparison with corresponding wild-type plants. In such plants, which are also described in WO 00/08184, a 197% increase in the phosphate content, 123% increase in the amylose content and a final viscosity in the RVA analysis which drops to 76% of that of the wild type can be observed in the isolated starch in comparison with untransformed wild-type plants. Moreover, the gel strength of the starch in question drops to 84% of the wild type.

The spectrophotometric analysis by the method of Morrison & Laignelet (1983, J. Cereal Sc. 1, 9-20) reveals an amylose content of up to a maximum of 89.14% (corresponding to 344% of the wild type) and a starch phosphate content which corresponds to up to a maximum of 522% of the phosphate content of starch isolated from corresponding wild-type plants in plants with a reduced activity of both a BEI and a BEII protein. The RVA analysis reveals a final viscosity value in these starches which is increased up to a maximum of 237%. Moreover, the modified granule morphology in starch grains isolated from such plants is distinguished by the fact that the granules have large grooves in the centre of the granule in question when viewed under the microscope under polarized light.

As a result, the skilled worker is familiar with plant cells and plants and starches synthesized by them which have an increased amylose and phosphate content but whose final viscosity in the RVA analysis is increased by not more than up to a maximum of 256% in comparison with wild-type plants which have not been genetically modified. Higher final viscosities in the RVA analysis have not been achieved to date. However, this would be desirable since less starch solids have to be employed, for example when using such a starch as thickener, gelling agent or binder, in order to achieve the desired effect. This allows for example the reduction of the amount of additives in human and animal foods, in healthcare products and in cosmetics. It would also be possible to employ smaller amounts of starch when using such a starch in glues, leading to reduced costs for example in making, for example, paper, cardboard and insulating board.

The present invention is thus based on the object of providing plant cells, plants and starch from suitable plant cells or plants with an increased amylose content and an increased phosphate content and, in the RVA analysis, a final viscosity which is increased by at least 270% and/or an increased gel strength of the gelatinized starch and/or a modified granule morphology.

This object is achieved by providing the embodiments specified in the patent claims.

A first aspect of the present invention thus relates to a plant cell which is genetically modified, the genetic modification leading to the reduction of the activity of one or more SSIII proteins occurring endogenously in the plant cell and to the reduction of the activity of one or more BEI proteins which occur endogenously in the plant cell and to the reduction of the activity of one or more BEII proteins which occur endogenously in the plant cell in comparison to corresponding plant cells, of wild-type plants, which have not been genetically modified.

In this context, the genetic modification can be any genetic modification which leads to a reduction of the activity of one or more SSIII proteins which occur endogenously in the plant cell and to the reduction of the activity of one or more BEI proteins which occur endogenously in the plant cell and to the reduction of the activity of one or more BEII proteins which occur endogenously in the plant cell in comparison to corresponding plant cells, of wild-type plants, which have not been genetically modified.

For the purposes of the invention, the genetic modification may encompass for example the generation of plant cells according to the invention by subjecting one or more genes to mutagenesis. The type of mutation is irrelevant as long as it leads to a reduction of the activity of an SSIII protein and/or a BEI protein and/or a BEII protein. In connection with the present invention, the term "mutagenesis" is understood as meaning any type of mutation, such as, for example, deletions, point mutations (nucleotide substitutions), insertions, inversions, gene conversions or chromosome translocation.

In this context, the mutation can be generated by using chemical agents or high-energy radiation (for example x-rays, neutron, gamma, UV radiation). Agents which can be employed for generating chemically induced mutations, and the mutations generated thereby by the action of the mutagens in question, are described, for example, by Ehrenberg and Husain, 1981, (Mutation Research 86, 1-113), Müller, 1972 (Biologisches Zentralblatt 91 (1), 31-48). The generation of rice mutants using gamma rays, ethyl methanesulfonate (EMS), N-methyl-N-nitrosurea or sodium azide (NaN3) is described, for example, in Jauhar and Siddiq (1999, Indian Journal of Genetics, 59 (1), 23-28), in Rao (1977), Cytologica 42, 443-450), Gupta and Sharma (1990, Oryza 27, 217-219) and Satoh and Omura (1981, Japanese Journal of Breeding 31 (3), 316-326). The generation of wheat mutants using NaN3 or maleic hydrazide is described in Arora et al. (1992 Annals of Biology 8 (1), 65-69). An overview over the generation of wheat mutants using different types of high-energy radiation and chemical agents is given in Scarascia-Mugnozza et al. (1993, Mutation Breeding Review 10, 1-28). Svec et al. (1998, Cereal Research Communications 26 (4), 291-396) describes the use of N-ethyl-N-nitrosurea for generating mutants in triticale. The use of MMS and gamma radiation for generating millet mutations is described in Shashidhara et al. (1990, Journal of Maharashtra Agriculture Universities 15 (1), 20-23).

The generation of mutants in plant species whose propagation is predominantly vegetatively was described for example for potatoes which produce a modified starch (Hovenkamp-Hermelink et al. (1987, Theoretical and Applied Genetics 75, 217-221) and for mint with an increased oil yield/modified oil quality (Dwivedi et al., 2000, Journal of Medicinal and Aromatic Plant Sciences 22, 460-463). All of these methods are suitable in principle for-generating the plant cells according to the invention and the starch produced by them.

Mutations in the relevant genes, in particular in genes encoding a BEI protein and/or a BEII protein and/or an SSIII protein, can be identified with the aid of methods known to the skilled worker. Analyses based on hybridizations with probes (Southern blot), the amplification by means of polymerase chain reaction (PCR), the sequencing of genomic sequences in question, and the search for individual nucleotide substitutions, may be employed in particular. One method of identifying mutations with the aid of hybridization patterns is, for example, the search for restriction fragment length polymorphisms (RFLP) (Nam et al., 1989, The Plant Cell 1, 699-705; Leister and Dean, 1993, The Plant Journal 4 (4), 745-750). An example of a method based on PCR is the analysis of amplified fragment length polymorphisms (AFLP) (Castiglioni et al., 1998, Genetics 149, 2039-2056; Meksem et al., 2001, Molecular Genetics and Genomics 265, 207-214; Meyer et al., 1998, Molecular and General Genetics 259,150-160). The use of amplified fragments cleaved with the aid of restriction endonucleases (cleaved amplified polymorphic sequences, CAPS) may also be used for identifying mutations (Konieczny and Ausubel, 1993, The Plant Journal 4, 403-410; Jarvis et al., 1994, Plant Molecular Biology 24, 685-687; Bachem et al., 1996, The Plant Journal 9 (5), 745-753). Methods for determining SNPs have been described, inter alia, by Qi et al. (2001, Nucleic Acids Research 29 (22), e116) Drenkard et al. (2000, Plant Physiology 124, 1483-1492) and Cho et al. (1999, Nature Genetics 23, 203-207). Methods which are particularly suitable are those which permit a large number of plants to be analysed within a short time for mutations in specific genes. Such a method, known as TILLING (targeting induced local lesions in genomes), has been described by McCallum et al. (2000, Plant Physiology 123, 439-442).

The use of all of these methods is suitable in principle for the purposes of the present invention.

Hoogkamp et al. (2000, Potato Research 43, 179-189) have isolated stable potato mutants which contain an amylose-free starch. These plants no longer synthesize active enzyme for a granule-bound starch synthase (GBSS I). After subjecting these plants to another mutagenesis, those which additionally have mutations in genes which are involved in starch biosynthesis may be selected. Plants which synthesize starch with improved characteristics might thus be generated. Using the suitable method, it is also possible to identify and isolate the plant cells according to the invention which produce a starch according to the invention.

Moreover, the plant cells according to the invention may also be generated with the aid of homologous transposons, that is to say transposons which are naturally present in the plant cells in question. A detailed description of this method is given hereinbelow.

All of the abovementioned methods are suitable in principle for generating plant cells according to the invention and the modified starch synthesized by them. The present invention therefore also relates to methods for generating genetically modified plant cells which synthesize a modified starch, this starch being characterized in that it has an amylose content of at least 30%, in that it has an increased phosphate content in comparison with starch from corresponding wild-type plant cells which have not been genetically modified and in that it has an increased final viscosity in the RVA analysis in comparison with starch from corresponding wild-type plant cells which have not been genetically modified.

A further aspect of the present invention relates to methods for generating a plant cell which synthesizes a modified starch, comprising the genetic modification of the plant cell, the genetic modification leading to the reduction of the activity of one or more SSIII proteins which occur endogenously in the plant cell and to the reduction of the activity of one or more BEI proteins which occur endogenously in the plant cell and to the reduction of the activity of one or more BEII proteins which occur endogenously in the plant cell, in comparison with corresponding plant cells, of wild-type plants, which have not been genetically modified.

Yet a further aspect of the present invention relates to methods for generating a genetically modified plant which synthesizes a modified starch, in which
a) a plant cell is generated as described above;
b) a plant is regenerated from, or using, the plant cell generated in accordance with a); and,
c) if appropriate, further plants are generated from the plant generated in accordance with step b).

In connection with the present invention, the term "genetically modified" means that the genetic information of the plant cell is altered.

In this context, a reduction of the activity of one or more SSIII proteins which occur endogenously in the plant cell and a reduction of the activity of one or more BEI proteins which occur endogenously in the plant cell and a reduction of the activity of one or more BEII proteins which occur endogenously in the plant cell is observed in the plant cells according to the invention in comparison with corresponding plant cells, of wild-type plants, which have not been genetically modified.

The genetic modifications for generating the plant cells according to the invention can be performed simultaneously or in consecutive steps. In this context, each genetic modification can lead to the reduction of the activity of one or more SSIII proteins and/or one or more BEI proteins and/or one or more BEII proteins. The starting material may be either wild-type plants or wild-type plant cells in which no previous genetic modification in order to reduce the activity of one or more SSIII proteins and/or one or more BEI proteins and/or one or more BEII proteins has been performed, or else genetically modified plant cells or plants in which the activity of one or more SSIII proteins and/or one or more BEI proteins and/or one or more BEII proteins has already been carried out by genetic modification. If such genetically modified plants (plant cells) constitute the starting material, the genetic modifications which are subsequently carried out preferably only relate to the activity of in each case one or more proteins whose activity has not been reduced yet (SSIII, BEI or BEII).

For example, a reduction of the expression of one or more SSIII genes which occur endogenously in the plant cell and a reduction of the expression of one or more BEI genes which occur endogenously in the plant cell and a reduction of the expression of one or more BEII genes which occur endogenously in the plant cell and/or a reduction of the activity of in each case one or more of the abovementioned proteins which occur in the plant cell is observed in genetically modified plant cells according to the invention in comparison with plant cells, of wild-type plants, which have not been genetically modified.

For the purposes of the present invention, the term "reduction of the activity" refers to a reduction of the expression of endogenous genes which encode SSIII, BEI and/or BEII proteins, and/or a reduction of the amount of SSIII, BEI and/or BEII protein in the cells and/or a reduction of the enzymatic activity of the SSIII, BEI and/or BEII proteins in the cells.

The reduction of the expression can be determined for example by measuring the amount of SSIII, BEI or BEII protein-encoding transcripts, for example by Northern blot analysis or RT-PCR. A reduction preferably means, in this context, a reduction of the amount of transcripts by at least 50%, in particular by at least 70%, preferably by at least 85% and especially preferably by at least 95% in comparison to corresponding cells which have not been genetically modified.

The reduction of the amount of SSIII, BEI and/or BEII proteins which results in a reduced activity of these proteins in the plant cells in question can be determined for example by immunological methods such as Western blot analysis, ELISA (enzyme-linked immunosorbent assay) or RIA (radio-immune assay). In this context, a reduction preferably means a reduction of the amount of SSIII, BEI and/or BEII protein by at least 50%, in particular by at least 70%, preferably by at least 85% and especially preferably by at least 95% in comparison to corresponding cells which have not been genetically modified.

In connection with the present invention, SSIII protein is understood as meaning a class of soluble starch synthases (ADP-glucose-1,4-alpha-D-glucan-4-alpha-D-glucosyltransferase; EC 2.4.1.21). Soluble starch synthases catalyze a glycosylation reaction, in which glucose residues of the substrate ADP-glucose are transferred to alpha-1,4-linked glucan chains, with formation of an alpha-1,4 linkage (ADP glucose+{(1,4)-alpha-D-glucosyl}(N)<=>ADP+{(1,4)-alpha-D-glucosyl}(N+1)).

SSIII proteins are described, for example, by Marshall et al. (1996, The Plant Cell 8, 1121-1135), Lie et al. (2000, Plant Physiology 123, 613-624), Abel et al. (The Plant Journal 10(6); (1996); 981-991) and in WO 00/66745. The structure of SSIII proteins frequently shows a sequence of domains. At the N terminus, SSIII proteins have a signal peptide for the transport into plastids. Towards the C terminus, this is followed by an N-terminal region, an SSIII-specific region and a catalytic domain (Li et al., 2000, Plant Physiology 123, 613-624). Further analyses which are based on primary sequence alignments, revealed that the potato SSIII protein has what is known as a carbohydrate binding domain (CBM). This domain (Pfam motiv cbm 25) comprises the amino acids 377 to 437 of the sequence of the potato SSIII protein shown in Seq ID No. 2. In connection with the present invention, an SSIII protein is therefore to be understood as meaning starch synthases which have at least 50%, preferably at least 60%, especially preferably at least 70%, more preferably at least 80% and in particular at least 90% identity with the sequence shown in Seq ID No. 3.

The term homology, or identity, is understood as meaning the number of agreeing amino acids (identity) with other proteins, expressed in percent. The identity is preferably determined by comparing the Seq ID No. 3 with other proteins with the aid of computer programmes. If sequences which are compared with each other are different in length, the identity is to be determined in such a way that the number of amino acids which the short sequences shares with the longer sequence determines the percentage identity. The identity can be determined routinely by means of known computer programmes which are publicly available such as, for example, ClustalW (Thompson et al., Nucleic Acids Research 22 (1994), 4673-4680). ClustalW is made publicly available by Julie Thompson and Toby Gibson, European Molecular Biology Laboratory, Meyerhofstrasse 1, D 69117 Heidelberg, Germany. ClustalW can likewise be downloaded from various internet pages, inter alia the IGBMC (Insitut de Génétique et de Biologie Moléculaire et Cellulaire, B.P.163, 67404 Illkirch Cedex, France and the EBI and all mirrored EBI internet pages (European Bioinformatics Institute, Wellcome Trust Genome Campus, Hinxton, Cambridge CB10 1SD, UK).

If the ClustalW computer programme Version 1.8 is used to determine the identity between, for example, the reference protein of the present application and other proteins, the following parameters are to be set: KTUPLE=1, TOPDIAG=5, WINDOW=5, PAIRGAP=3, GAPOPEN=10, GAPEXTEND=0.05, GAPDIST=8, MAXDIV=40, MATRIX=GONNET, ENDGAPS(OFF), NOPGAP, NOHGAP.

One possibility of finding similar sequences is to carry out sequence database researches. Here, one or more sequences are entered as what is known as a query. This query sequence is then compared with sequences present in the selected databases using statistical computer programmes. Such database queries (blast searches) are known to the skilled worker and can be carried out at different suppliers. If, for example, such a database query is carried out at the NCBI (National Center for Biotechnology Information), the standard setting for the respective comparison query should be used. For protein sequences comparisons (blastp), these settings are: Limit entrez=not activated; Filler=low complexity activated; Expect value=10; word size=3; Matrix=BLOSUM62; Gap costs: Existence=11, Extension=1. The result of such a query is, among other parameters, the degree of identity between the query sequence and the similar sequences found in the databases.

Thus, an SSIII protein is to be understood as meaning, in connection with the present invention, starch synthases which, when using at least one of the above-described methods for determining the identity with the sequence shown in Seq ID No. 3, have at least 50%, preferably at least 60%, especially preferably at least 70%, more preferably at least 80% and in particular at least 90% identity.

For the purposes of the present invention, the term SSIII gene is understood as meaning a nucleic acid molecule (DNA, cDNA, RNA) which encodes an SSIII protein, preferably from potato. Nucleic acid molecules encoding an SSIII protein have been-described for a variety of plant species such as, for example, potato (Abel et al., The Plant Journal 10(6); (1996); 981-991), wheat (WO 00/66745, Li et al., 2000, Plant Physiology 123, 613-624; Genbank Acc. No AF258608; Genbank Acc. No AF258609), maize (Gao et al., 1998, Plant Cell 10 (3), 399-412; Genbank Acc. No AF023159), *Vignia* (Genbank Acc. No AJ225088), rice (Genbank Acc. No AY100469; Genbank Acc. No AF43291) and *Arabidopsis* (Genbank Acc. No AC007296).

For the purposes of the present invention, the term "branching enzyme" or "BE protein" ($\alpha$-1,4-glucan: $\alpha$-1,4-glucan-6-glycosyltransferase, E.C. 2.4.1.18) is understood as meaning a protein which catalyzes a transglycosylation reaction in which $\alpha$-1,4-linkages of an $\alpha$-1,4-glucan donor are hydrolyzed and the $\alpha$-1,4-glucan chains liberated in this process are transferred to an $\alpha$-1,4-glucan acceptor chain, where they are converted into $\alpha$-1,6 linkages.

The term "BEI protein" is to be understood as meaning, for the purposes of the present invention, an isoform I branching enzyme (branching enzyme=BE). The BEI protein is preferably derived from potato plants.

In this context, isoform terminology relies on the nomenclature proposed by Smith-White and Preiss (Smith-White and Preiss, Plant Mol Biol. Rep. 12, (1994), 67-71, Larsson et al., Plant Mol Biol. 37, (1998), 505-511). This nomenclature assumes that all enzymes which have a higher degree of homology (identity) at the amino acid level with the maize BEI protein (GenBank Acc. No. D11081; Baba et al., Biochem. Biophys. Res. Commun. 181 (1), (1991), 87-94; Kim et al. Gene 216, (1998), 233-243) than to the maize BEII protein (Genbank Acc. No AF072725, U65948) are referred to as isoform I branching enzymes, abbreviated to BEI proteins.

The term "BEII protein" is to be understood as meaning, for the purposes of the present invention, an isoform II branching enzyme (branching enzyme=BE). This enzyme preferably originates from potato plants. In connection with the present invention, all enzymes which, at the amino acid level, have a higher degree of homology (identity) with the maize BEII protein (Genbank Acc. No AF072725, U65948) than with the maize BEI protein (Genbank Acc. No. D 11081, AF 072724) shall be referred to as BEII protein.

The term "BEI gene" is understood as meaning, for the purposes of the present invention, a nucleic acid molecule (cDNA, DNA) which encodes a "BEI protein", preferably a BEI protein from potato plants. Such nucleic acid molecules have been described for a large number of plants, for example for maize (Genbank Acc. No. D 11081, AF 072724), rice (Genbank Acc. No. D11082), pea (Genbank Acc. No. X80010) and potato. Various forms of the BEI gene, or the BEI protein, from potato have been described, for example, by Khoshnoodi et al., Eur. J. Biochem. 242 (1), 148-155 (1996), Genbank Acc. No. Y 08786 and by Kossmann et al., Mol. Gen. Genet. 230, (1991), 39-44). In potato plants, the BEI gene is expressed predominantly in the tubers and to a very minor degree in the leaves (Larsson et al., Plant Mol. Biol. 37, (1998), 505-511).

The term "BEII gene" is to be understood as meaning, for the purposes of the present invention, a nucleic acid molecule (for example cDNA, DNA) which encodes a "BEII protein", preferably a BEII protein from potato plants. Such nucleic acid molecules have been described for a large number of plants, for example for potato (GenBank Acc. No. AJ000004, AJ011888, AJ011889, AJ011885, AJ011890, EMBL GenBank A58164), maize (AF 072725, U65948), barley (AF064561), rice (D16201) and wheat (AF 286319). In potato plants, the BEII gene is expressed predominantly in the tubers and to a very minor degree in the leaves (Larsson et al., Plant Mol. Biol. 37, (1998), 505-511).

The term "transgenic" is to be understood as meaning, in the present context, that the genetic information of the plant cells according to the invention deviates from corresponding plant cells which have not been genetically modified owing to the introduction of a foreign nucleic acid molecule or several foreign nucleic acid molecules into the cell.

In a further embodiment of the present invention, the genetic modification of the transgenic plant cell according to the invention consists in the introduction of one or more foreign nucleic acid molecules whose presence and/or expression leads to the reduction of the activity of SSIII and BEI and BEII proteins in comparison to corresponding plant cells, of wild-type plants, which have not been genetically modified. Specifically, the term "genetic manipulation" is understood as meaning the introduction of homologous and/or heterologous nucleic acid molecules and/or foreign nucleic acid molecules which have been subjected to mutagenesis into a plant cell, where said introduction of these molecules leads to the reduction of the activity of an SSIII protein and/or a BEI protein and/or BEII protein.

The term "foreign nucleic acid molecule" or "of foreign nucleic acid molecules" is understood as meaning, for the purposes of the present invention, such a molecule which either does not occur naturally in the plant cells in question, or which does not naturally occur in the plant cells in the specific spatial arrangement, or which is localized at a site in the genome of the plant cell where it does not occur naturally. The foreign nucleic acid molecule is preferably a recombinant molecule which consists of various elements whose combination, or specific spatial arrangement, does not naturally occur in plant cells.

The foreign nucleic acid molecule(s) which is, or are, used for the genetic modification may take the form of a hybrid nucleic acid construct or of several separate nucleic acid constructs, in particular of what are known as single, dual and triple constructs. Thus, the foreign nucleic acid molecule may be, for example, what is known as a "triple construct", which is understood as meaning one single vector for plant transformation which contains not only the genetic information for inhibiting the expression of one or more endogenous SSIII genes, but also the genetic information for inhibiting the expression of one or more BEI genes and of one or more BEII genes, or whose presence, or expression, leads to the reduction of the activity of one or more SSIII, BEI and BEII proteins.

In a further embodiment, the foreign nucleic acid molecule may be what is known as a "dual construct", which is understood as meaning a vector for plant transformation which contains the genetic information for inhibiting the expression of two out of the three target genes (SSIII, BEI, BEII gene) or whose presence, or expression, leads to the reduction of the activity of two out of the three target proteins (SSIII, BEI, BEII proteins). The inhibition of the expression of the third target gene and/or the reduction of the activity of the third target protein is effected, in this embodiment of the invention, with the aid of a separate, foreign nucleic acid molecule which contains the relevant genetic information for inhibiting this third target gene.

In a further embodiment of the invention, it is not a triple construct which is introduced into the genome of the plant cell, but several different foreign nucleic acid molecules are introduced, one of these foreign nucleic acid molecules being, for example, a DNA molecule which constitutes, for example, a cosuppression construct which brings about a reduction of the expression of one or more endogenous SSIII genes, and a further foreign nucleic acid molecule being a DNA molecule which encodes, for example, an antisense RNA which brings about a reduction of the expression of one or more endogenous BEI and/or BEII genes. When constructing the foreign nucleic acid molecules, however, the use of any combination of antisense, cosuppression, ribozyme and double-stranded RNA constructs or in-vivo mutagenesis which leads to a simultaneous reduction of the gene expression of endogenous genes encoding one or more SSIII, BEI and BEII proteins, or which leads to a simultaneous reduction of the activity of one or more SSIII, BEI and BEII proteins, is also suitable in principle.

The foreign nucleic acid molecules can be introduced into the genome of the plant cell either simultaneously ("cotransformation") or else one after the other, i.e. in succession at different times ("supertransformation").

The foreign nucleic acid molecules can also be introduced into different individual plants of one species. This may give rise to plants in which the activity of one target protein, or two target proteins, (BEI, BEII, SSIII) is reduced. Subsequent hybridizing may then give rise to plants in which the activity of all three of the target proteins is reduced.

Instead of a wild-type plant cell or plant, a mutant which is distinguished by already showing a reduced activity of one or more target proteins (BEI, BEII, SSIII) may further be used for introducing a foreign nucleic acid molecule or for generating the plant cells or plants according to the invention. The mutants may take the form of spontaneously occurring mutants or else of mutants which have been generated by the specific application of mutagens. Possibilities of generating such mutants have been described further above.

The plant cells according to the invention and their starch can be generated, or produced, by using what is known as insertion mutagenesis (review article: Thorneycroft et al., 2001, Journal of experimental Botany 52 (361), 1593-1601). Insertion mutagenesis is to be understood as meaning, in particular, the insertion of transposons or what is kown as transfer DNA (T-DNA) into a gene encoding a BEI protein and/or BEII protein and/or an SSIII protein, thus reducing the activity of said proteins in the cell in question.

The transposons may take the form of transposons which occur naturally in the cell (endogenous transposons) or else those which do not occur naturally in said cell but have been introduced into the cell by means of recombinant methods, such as, for example, by transforming the cell (heterologous transposons). Modifying the expression of genes by means of transposons is known to the skilled worker. A review of the utilization of endogenous and heterologous transposons as tools in plant biotechnology can be found in Ramachandran and Sundaresan (2001, Plant Physiology and Biochemistry 39, 234-252). The possibility of identifying mutants in which specific genes have been inactivated by transposon insertion mutagenesis can be found in a review by Maes et al. (1999, Trends in Plant Science 4 (3), 90-96). The generation of rice mutants with the aid of endogenous transposons is described by Hirochika (2001, Current Opinion in Plant Biology 4, 118-122). The identification of maize genes with the aid of endogenous retrotransposons is shown, for example, in Hanley et al. (2000, The Plant Journal 22 (4), 557-566). The possibility of generating mutants with the aid of retrotransposons and methods for identifying mutants are described by Kumar and Hirochika (2001, Trends in Plant Science 6 (3), 127-134). The activity of heterologous transposons in different species has been described both for dicotyledonous and for monocotyledonous plants, for example for rice (Greco et al., 2001, Plant Physiology 125, 1175-1177; Liu et al., 1999, Molecular and General Genetics 262, 413-420; Hiroyuki et al., 1999, The Plant Journal 19 (5), 605-613; Jeon and Gynheung, 2001, Plant Science 161, 211-219), barley (2000, Koprek et al., The Plant Journal 24 (2), 253-263), *Arabidopsis thaliana* (Aarts et al., 1993, Nature 363, 715-717, Schmidt and Willmitzer, 1989, Molecular and General Genetics 220, 17-24; Altmann et al., 1992, Theoretical and Applied Gentics 84, 371-383; Tissier-et al., 1999, The Plant Cell 11, 1841-1852), tomato (Beizile and Yoder, 1992, The Plant Journal 2 (2), 173-179) and potato (Frey et al., 1989, Molecular and General Genetics 217, 172-177; Knapp et al., 1988, Molecular and General Genetics 213, 285-290).

In principle, the plant cells and plants according to the invention, and the starch produced by them, can be generated, or produced, with the aid of both homologous and heterologous transposons, the use of homologous transposons also including those transposons which are already naturally present in the plant genome.

T-DNA insertion mutagenesis is based on the fact that certain segments (T-DNA) of Ti plasmids from *Agrobacterium* are capable of integrating into the genome of plant cells. The site of integration into the plant chromosome is not fixed but may take place at any position. If the T-DNA integrates in a segment of the chromosome which constitutes a gene function, this may lead to a modification of the gene expression and thus also to an altered activity of a protein encoded by the gene in question. In particular, the integration of a T-DNA into the coding region of a protein frequently means that the protein in question can no longer be synthesized in active form, or not at all, by the cell in question. The use of T-DNA insertions for the generation of mutants is described, for example, for *Arabidopsis thaliana* (Krysan et al., 1999, The Plant Cell 11, 2283-2290; Atipiroz-Leehan and Feldmann, 1997, Trends in genetics 13 (4), 152-156; Parinov and Sundaresan, 2000, Current Opinion in Biotechnology 11, 157-161) and rice (Jeon and An, 2001, Plant Science 161, 211-219; Jeon et al., 2000, The Plant Journal 22 (6), 561-570). Methods for identifying mutants which have been generated with the aid of T-DNA insertion mutagenesis are described, inter alia, by Young et al., (2001, Plant Physiology 125, 513-518), Parinov et al. (1999, The Plant cell 11, 2263-2270), Thorneycroft et al. (2001, Journal of Experimental Botany 52, 1593-1601), and McKinney et al. (1995, The Plant Journal 8 (4),613-622).

In principle, T-DNA mutagenesis is suitable for generating the plant cells according to the invention and for producing the starch produced by them.

In a further embodiment of the present invention, the presence and/or the expression of one or more foreign nucleic acid molecules leads to the inhibition of the expression of endogenous genes which encode SSIII proteins, BEI proteins and BEII proteins.

The plant cells according to the invention can be generated by various methods with which the skilled worker is familiar, for example by those which lead to an inhibition of the expression of endogenous genes encoding an SSIII, BEI or BEII protein. They include, for example, the expression of a corresponding antisense RNA or a double-stranded RNA construct, the provision of molecules or vectors which confer a cosuppression effect, the expression of a suitably constructed ribozyme which specifically cleaves transcripts encoding an SSIII, BEI or BEII protein, or what is known as "in-vivo mutagenesis". Moreover, the reduction of the SSIII and/or BEI and/or BEII activity in the plant cells may also be brought about by the simultaneous expression of sense and antisense RNA molecules of the specific target gene to be repressed, preferably the SSIII and/or BEI and/or BEII gene. The skilled worker is familiar with these methods.

Moreover, it is known that the generation in planta of double-stranded RNA molecules of promoter sequences in trans can lead to methylation and transcriptional inactivation of homologous copies of this promoter (Mette et al., EMBO J. 19, (2000), 5194-5201).

Other methods for reducing the activity of proteins are described hereinbelow.

All of these methods are based on the introduction of one or more foreign nucleic acid molecules into the genome of plant cells.

To inhibit gene expression by means of antisense or cosuppression technology it is possible to use, for example, a DNA molecule which encompasses all of the sequence encoding an SSIII and/or BEI and/or BEII protein including any flanking sequences which may be present, or else DNA molecules which only encompass parts of the coding sequence, which must be long enough in order to bring about an antisense effect, or cosuppression effect, in the cells. Sequences which are suitable generally have a minimum length of not less than 15 bp, preferably a length of 100-500 bp, and for effective antisense or cosuppression inhibition in particular sequences which have a length of over 500 bp.

Another possibility which is suitable for antisense or cosuppression approaches is the use of DNA sequences with a high degree of homology with the endogenous sequences which encode SSIII, BEI or BEII proteins and which occur endogenously in the plant cell. The minimum degree of homology should exceed approximately 65%. The use of sequences with homology levels of at least 90%, in particular between 95 and 100%, is to be preferred.

The use of introns, i.e. noncoding regions of genes, which encode SSIII, BEI and/or BEII proteins is also feasible for achieving an antisense or cosuppression effect.

The use of intron sequences for inhibiting the gene expression of genes which encode starch biosynthesis proteins has been described in the international patent applications WO97/04112, WO97/04113, WO98/37213, WO98/37214.

The skilled worker is familiar with methods for achieving an antisense and cosuppression effect. The cosuppression inhibition method has been described, for example, in Jorgensen (Trends Biotechnol. 8 (1990), 340-344), Niebel et al., (Curr. Top. Microbiol. Immunol. 197 (1995), 91-103), Flavell et al. (Curr. Top. Microbiol. Immunol. 197 (1995), 43-46), Palaqui and Vaucheret (Plant. Mol. Biol. 29 (1995), 149-159), Vaucheret et al., (Mol. Gen. Genet. 248 (1995), 311-317), de Borne et al. (Mol. Gen. Genet. 243 (1994), 613-621).

The expression of ribozymes for reducing the activity of specific enzymes in cells is also known to the skilled worker and described, for example, in EP-B1 0321201. The expression of ribozymes in plant cells has been described, for example, in Feyter et al. (Mol. Gen. Genet. 250, (1996), 329-338).

Moreover, the reduction of the SSIII and/or BEI and/or BEII activity in the plant cells may also be achieved by what is known as "in-vivo mutagenesis", where an RNA-DNA oligonucleotide hybrid ("chimeroplast") is introduced into cells by means of transforming cells (Kipp, P. B. et al., Poster Session at the "5$^{th}$ International Congress of Plant Molecular Biology, 21-27 Sep. 1997, Singapore; R. A. Dixon and C. J. Arntzen, Meeting report on "Metabolic Engineering in Transgenic Plants", Keystone Symposia, Copper Mountain, Colo., USA, TIBTECH 15, (1997), 441-447; International Patent Application WO 9515972; Kren et al., Hepatology 25, (1997), 1462-1468; Cole-Strauss et al., Science 273, (1996), 1386-1389; Beetham et al., 1999, PNAS 96, 8774-8778).

Part of the DNA component of the RNA-DNA oligonucleotide is homologous with a nucleic acid sequence of an endogenous SSIII, BEI and/or BEII gene, but contains a mutation in comparison with the nucleic acid sequence of an endogenous SSIII, BEI and/or BEII gene or contains a heterologous region which is surrounded by the homologous regions.

Owing to base pairing of the homologous regions of the RNA-DNA oligonucleotide and of the endogenous nucleic acid molecule, followed by homologous recombination, the mutation or heterologous region contained in the DNA component of the RNA-DNA oligonucleotide can be transferred into the genome of a plant cell. This leads to a reduction of the activity of one or more SSIII, BEI and/or BEII proteins.

Moreover, the reduction of the SSIII and/or BEI and/or BEII activity in the plant cells may also be caused by the simultaneous expression of sense and antisense RNA molecules of the specific target gene to be repressed, preferably the SSIII and/or BEI and/or BEII gene.

This may be achieved for example by the use of chimeric constructs which contain "inverted repeats" of the respective target gene or parts of the target gene. The chimeric constructs encode sense and antisense RNA molecules of the target gene in question. Sense and antisense RNA are synthesized simultaneously in planta as one RNA molecule, it being possible for sense and antisense RNA to be separated from each other by a spacer and to form a double-stranded RNA molecule.

It has been demonstrated that the introduction of inverted-repeat DNA constructs in the genome of plants is a highly effective method for repressing the genes corresponding to the inverted-repeat DNA constructs (Waterhouse et al., Proc. Natl. Acad. Sci. USA 95, (1998), 13959-13964; Wang and Waterhouse, Plant Mol. Biol. 43, (2000), 67-82;Singh et al., Biochemical Society Transactions Vol. 28 part 6 (2000), 925-927; Liu et al., Biochemical Society Transactions Vol. 28 part 6 (2000), 927-929); Smith et al., (Nature 407, (2000), 319-320; International Patent Application WO99/53050 A1). Sense and antisense sequences of the target gene(s) may also be expressed separately from one another by means of identical or different promoters (Nap, J-P et al, 6$^{th}$ International Congress of Plant Molecular Biology, Quebec, 18-24 Jun., 2000; Poster S7-27, Session S7).

The reduction of the SSIII and/or the BEI and/or the BEII activity in the plant cells can thus also be achieved by generating double-stranded RNA molecules of SSIII and/or BEI and/or BEII genes. To this end, it is preferred to introduce, into the genome of plants, inverted repeats of DNA molecules of SSIII and/or BEI and/or BEII genes or cDNAs, the DNA molecules to be transcribed (SSIII, BEI or BEII gene or cDNA, or fragments of these genes or cDNAs) being under the control of a promoter which governs the expression of said DNA molecules.

Moreover, it is known that the formation of double-stranded RNA molecules of promoter DNA molecules in plants in trans can lead to methylation and transcriptional inactivation of homologous copies of these promoters, hereinbelow referred to as target promoters (Mette et al., EMBO J. 19, (2000), 5194-5201).

Thus, it is possible, via the inactivation of the target promoter, to reduce the gene expression of a specific target gene (for example SSIII, BEI or BEII gene) which is naturally under the control of this target promoter.

This means that the DNA molecules which encompass the target promoters of the genes to be repressed (target genes) are in this case—in contrast to the original function of promoters in plants—not used as control elements for the expression of genes or cDNAs, but as transcribable DNA molecules themselves.

To generate the double-stranded target promoter RNA molecules in planta, where they may be present in the form of RNA hairpin molecules, it is preferred to use constructs which contain inverted repeats of the target promoter DNA molecules, the target promoter DNA molecules being under the control of a promoter which governs the gene expression of said target promoter DNA molecules. These constructs are subsequently introduced into the genome of plants. Expression of the inverted repeats of said target promoter DNA molecules leads to the formation of double-stranded target promoter RNA molecules in planta (Mette et al., EMBO J. 19, (2000), 5194-5201). The target promoter can thus be inactivated.

The reduction of the SSIII and/or BEI and/or BEII activity in the plant cells can thus also be achieved by generating double-stranded RNA molecules of promoter sequences of SSIII and/or BEI and/or BEII genes. To this end, it is preferred to introduce, into the genome of plants, inverted repeats of promoter DNA molecules of SSIII and/or BEI and/or BEII promoters, the target promoter DNA molecules to be transcribed (SSIII, BEI and/or BEII promoter) being under the control of a promoter which governs the expression of said target promoter DNA molecules.

The skilled worker furthermore knows to achieve the activity of one or more SSIII, BEI and/or BEII proteins by expressing nonfunctional derivatives, in particular trans-dominant mutants, of such proteins and/or by expressing antagonists/inhibitors of such proteins.

Antagonists/inhibitors of such proteins encompass for example antibodies, antibody fragments or molecules with similar binding characteristics. For example, a cytoplasmic scFv antibody was employed for modulating the activity of the phytochrome A protein in genetically modified tobacco plants (Owen, Bio/Technology 10 (1992), 790-4; Review: Franken, E, Teuschel, U. and Hain, R., Current Opinion in Biotechnology 8, (1997), 411-416; Whitelam, Trends Plant Sci. 1 (1996), 268-272).

Useful promoters for the expression of nucleic acids which reduce the activity of a target gene are, for example, the promoter of the cauliflower mosaic virus 35S RNA and the maize ubiquitin promoter for constitutive expression, the patatin gene promoter B33 (Rocha-Sosa et al., EMBO J. 8 (1989), 23-29), the MCPI promoter of the potato metallocarbopeptidase inhibitor gene (Hungarian Patent Application HU9801674) or the potato GBSSI promoter (International Patent Application WO 92/11376) for tuber-specific expression in potatoes, or a promoter which ensures expression uniquely in photosynthetically active tissues, for example the ST-LS1 promoter (Stockhaus et al., Proc. Natl. Acad. Sci. USA 84 (1987), 7943-7947; Stockhaus et al., EMBO J. 8 (1989), 2445-2451), the Ca/b promoter (see, for example, U.S. Pat. Nos. 5,656,496, 5,639,952, Bansal et al., Proc. Natl. Acad. Sci. USA 89, (1992), 3654-3658) and the Rubisco SSU promoter (see, for example, U.S. Pat. Nos. 5,034,322, 4,962,028), or, for endosperm-specific expression, the glutelin promoter (Leisy et al., Plant Mol. Biol. 14, (1990), 41-50; Zheng et al., Plant J. 4, (1993), 357-366; Yoshihara et al., FEBS Lett. 383, (1996), 213-218), the Shrunken-1 promoter (Werr et al., EMBO J. 4, (1985), 1373-1380), the wheat HMG promoter, the USP promoter, the phaseolin promoter or promoters of zein genes from maize (Pedersen et al., Cell 29, (1982), 1015-1026; Quatroccio et al., Plant Mol. Biol. 15 (1990), 81-93).

The expression of the foreign nucleic acid molecule(s) is particularly advantageous in those plant organs which store starch. Examples of such organs are the tuber of the potato plant or the kernels, or endosperm, of maize, wheat or rice plants. This is why it is preferred to use promoters which confer expression in these organs.

However, it is also possible to use promoters which are activated only at a point in time determined by external factors (see, for example, WO 93/07279). Promoters which may be of particular interest in this context are promoters of heat-shock proteins, which permit simple induction. Others which can be [lacuna] are seed-specific promoters such as, for example, the Vicia faba USP promoter, which ensures seed-specific expression in Vicia faba and other plants (Fiedler et al., Plant Mol. Biol. 22, (1993), 669-679; Bäumlein et al., Mol. Gen. Genet. 225, (1991), 459-467). Fruit-specific promoters such as, for example, those described in WO91/01373 may furthermore also be employed.

Another element which may be present is a termination sequence, which serves for the correct termination of transcription and for the addition of a poly-A tail to the transcript, which is believed to have a function in stabilizing the transcripts. Such elements are described in the literature (cf., for example, Gielen et al., EMBO J. 8 (1989), 23-29) and can be substituted as desired.

The transgenic plant cells according to the invention synthesize a modified starch whose physico-chemical properties, in particular the amylose content and the amylose/amylopectin ratio, the phosphorus content, the viscosity behaviour, the gel strength, the granule size and/or the granule morphology is modified in comparison with starch synthesized in wild-type plants so that it is better suited to specific uses.

The present invention therefore also relates to a genetically modified plant cell according to the invention, in particular to a transgenic plant cell which synthesizes a modified starch.

Surprisingly, it has been found that the starch composition in the plant cells according to the invention is modified in such a way that the amylose content amounts to at least 30% and the phosphate content is increased and the end viscosity in the RVA analysis is increased in comparison with starch from plant cells from corresponding wild-type plants, so that this starch is better suited to specific uses.

In particular the starches according to the invention have the advantage that they gelatinize completely under standard conditions despite the increased amylose content. This markedly improves the processability of the starch in comparison with other starches with an increased amylose content. An increased temperature or increased pressure is therefore not necessary for gelatinizing the starch according to the invention. This is why the use of specific apparatuses such as, for example, jet cookers, extruders or autoclaves can be dispensed with when breaking down these starches. Another advantage of the starches according to the invention is that, when subjected to processing with hot rollers, they may be applied to the latter in the form of a suspension. Other starches with an increased amylose content would gelatinize, when subjected to this type of processing, to a limited extent only, if at all, and would not be capable of being applied to the rollers in question in the form of a paste or film.

The starches according to the invention are particularly suitable for all applications where the thickening ability, the gelling characteristics or the binding characteristics of added substances are of importance. The starch according to the invention is therefore particularly suitable for the production of foodstuffs such as, for example, baked goods, instant food, blancmange, soups, confectionery, chocolate, icecream, batter for fish or meat, frozen desserts or extruded snacks. Moreover, the starch according to the invention is suitable for the production of glues, for applications in textile processing, as additive to building materials, for applications in the field of animal nutrition, as additive for cosmetics, and in papermaking.

The starch which has been isolated from plant cells according to the invention is particularly suitable for the production of pregelatinized starch. Pregelatinized starches are physically modified starches which are produced predominantly by wet-heat treatment. As opposed to native starch, they form dispersions/pastes or gels with cold water, depending on the concentration of the pregelatinized starch used and as a function of the starch type used for producing the pregelatinized starch. Owing to these characteristics, a series of possible applications exist for pregelatinized starches in the food industry and in addition in many fields of industry. The use of pregelatinized starch, also referred to as cold-swelling starch, instead of native starch frequently has the advantage that production processes can be simplified and shortened.

The production of, for example, instant desserts and instant blancmange requires pregelatinized starches which, after being stirred into cold fluid such as, for example, water or milk, form firm gels in a short time as is the case with, for example, a blancmange which requires boiling. These demands are not met by the commercial pregelatinized starches made with wheat starch, potato starch or corn starch. To obtain the abovementioned characteristics, additives to the pregelatinized starch such as gelatin, alginate, carrageenan and/or inorganic salts are required in the case of the pregelatinized starches which are currently commercially available. This addition of what are known as adjuvants is not required for example after the production of pregelatinized starches using starches according to the invention which are isolated from plant cells according to the invention.

The present invention also relates to a plant cell according to the invention with a modified starch with modified granule morphology.

For the purposes of the present invention, the term granule morphology is intended to refer to size and surface structure of native starch granules. Starch is stored in the storage organs such as, for example, tubers, roots, embryos or endosperm of plants, as a crystalline structure in granular form. Starch granules in which these granular structures are retained after the starch has been isolated from plant cells are referred to as native starch. The mean granule size (determined by the method described hereinbelow) of the native starch according to the invention is markedly lower than that of native starch isolated from wild-type plants. In the scanning electron micrograph (see FIGS. 4 and 5) it can be seen clearly that, surprisingly, native starch granules according to the invention have a rough surface with many pores. The surface structure of native starch granules isolated from wild-type plants, in contrast, is predominantly smooth in structure and no pores are discernible.

Both the presence of smaller granules and the rough surface with its pores lead to the fact that the surface area of starch granules according to the invention is considerably larger—at the same volume—than the surface area of starch granules isolated from wild-type plants. The starch according to the invention is therefore particularly suited to the use as carrier for, for example, flavourings, pharmacologically active substances, prebiotics, probiotic microorganisms, enzymes or colorants. These starches are also particularly suitable for coagulating substances and in papermaking.

A further possible application for the starches according to the invention is in the field of drilling for raw materials. Thus, when drilling for crude oil, adjuvants and/or lubricants must be employed which avoid overheating of the drill or drill column. Owing to its particular gelatinization properties, the starch according to the invention is therefore also particularly suited to the use in this field.

The present invention also relates to a plant cell according to the invention which contains a modified starch with an amylose content of at least 30% and which has an increased phosphate content and an increased final viscosity in the RVA analysis in comparison with starch from corresponding plant cells, from wild-type plants, which have not been genetically modified.

In connection with the present inveniton, the amylose content is determined by the method of Hovenkamp-Hermelink et al. (Potato Research 31, (1988), 241-246) described further below for potato starch. This method may also be applied to isolated starches from other plant species. Methods for isolating starches are known to the skilled worker.

For the purposes of the present invention, "phosphate content" of the starch refers to the content of phosphate covalently bonded in the form of starch phosphate monoesters.

In connection with the present invention, the term "increased phosphate content" means that the total phosphate content of covalently bonded phosphate and/or the phosphate content in C-6 position of the starch synthesized in the plant cells according to the invention is increased, by preference by at least 270%, more preferably by at least 300%, especially preferably by at least 350% in comparison with starch from plant cells of corresponding wild-type plants.

For the purposes of the present invention, the term "phosphate content in C6 position" is understood as meaning the content of phosphate groups which are bonded at the carbon atom position "6" of the glucose monomers of the starch. In principle, the positions C2, C3 and C6 of the glucose units can be phosphorylated in starch in vivo. In connection with the present invention, the determination of the phosphate content in C6 position (=C6-P content) can be carried out via the determination of glucose-6-phosphate by means of a visual-enzymatic test (Nielsen et al., Plant Physiol. 105, (1994), 111-117) (see below).

In connection with the present invention, the term "total phosphate content" of the starch refers to the content of phosphate bound covalently in C2, C3 and C6 position of the glucose units in the form of starch phosphate monoesters. The content of phosphorylated non-glucans such as, for example, phospholipids, does not come under the term "total phosphate content" in accordance with the invention. Phosphorylated non-glucans must therefore be removed quantitatively before determining the total phosphate content. Methods for separating the phosphorylated non-glucans (for example phospholipids) and the starch are known to the skilled worker.

Methods for determining the total phosphate content are known to the skilled worker and described hereinbelow.

In a further embodiment of the invention, the plant cells according to the invention synthesize a starch which have a phosphate content of 40-120 nmol, in particular 60-110 nmol, preferably 80-100 C6-P per mg starch in C6 position of the glucose monomers of the starch.

A protocol for carrying out the RVA analysis is described further below. Mention must be made in particular that the RVA analysis of potato starches frequently operates with an 8% starch suspension (w/w). The documentation included with the apparatus "RVAsuper3" (instructions, Newport Scientific Pty Ltd., Investment Support Group, Warded NSW 2102, Australia) recommends a suspension containing approximately 10% of starch for the analysis of potato starch.

Surprisingly, it has been found in the case of the starch from potato plants in relation to the present invention, that it was not possible to use an 8% starch suspension (2 g of starch in 25 ml of water) for the analysis since the final viscosity achieved values beyond the range of the apparatus. This is why only 6% starch suspensions (1.5 g of starch in 25 ml of water) were employed for the RVA analysis instead of 8% starch suspensions. In connection with the present invention, "increased end viscosity in the RVA analysis" is therefore understood as meaning an increase by at least 150%, especially by at least 200%, in particular by at least 250%, in comparison with wild-type plants which have not been genetically modified. The increase of the end viscosities relates to 6% starch suspensions in this context.

In connection with the present invention, a potato starch is furthermore understood as meaning one with an at least 300 RVU, especially 400 RVU, in particular 500 RVU final viscosity in the RVA analysis with a 6% starch content. The determination of the RVU values will be discussed in detail hereinbelow.

In a further preferred embodiment, the present invention relates to plant cells according to the invention which synthesize a modified starch which, after gelatinization in water, forms a gel with an increased gel strength in comparison with a gel made with starch of corresponding wild-type plant cells which have not been genetically modified.

For the purposes of the present invention, the term "increased gel strength" is understood as meaning an increase of the gel strength by preference by at least 300%, in particular by at least 500%, more preferably by at least 700% and especially preferably by at least 800%, up to a maximum of not more than 2000% or by not more than 1500% in comparison with the gel strength of starch from corresponding wild-type plant cells which have not been genetically modified.

In connection with the present invention, the gel strength shall be determined with the aid of a Texture Analyser under the conditions described hereinbelow.

To prepare starch gels, the crystalline structure of native starch must first be destroyed by heating in aqueous suspension with constant stirring. This was carried out with the aid of a Rapid Visco Analyser (Newport Scientific Pty Ltd., Investmet Support Group, Warriewod NSW 2102, Australia). As already mentioned further above, the 8% starch suspension was replaced by an only 6% starch suspension in the case of starch from potato plants since the final viscosities of the 8% suspensions were outside the operating range of the apparatus. To determine gel strength, the starch suspensions gelatinized in the Rapid Visco Analyser were stored over a certain period and then subjected to analysis using a Texture Analyser. Accordingly, 8% gelatinized starch suspensions were also replaced by 6% gelatinized starch suspensions for determining gel strength.

In a further embodiment of the present invention, the modified starch synthesized in the plant cells according to the invention is distinguished not only by an increased amylose content in comparison with starch from corresponding wild-type plants and an increased phosphate content and an increased final viscosity in the RVA analysis, but also by a modified side chain distribution.

In a further embodiment, the present invention thus relates to plant cells according to the invention which synthesize a modified starch, the modified starch being characterized by a modified side chain distribution.

In one embodiment of the present invention, the term "modified side chain distribution" is understood as meaning a reduction of the amount of short side chains with a DP (=degree of polymerization) of 6 to 11 by at least 10%, preferably by at least 15%, in particular by at least 30% and especially preferably by at least 50% in comparison with the amount of short side chains with a DP of 6 to 11 of amylopectin from wild-type plants and/or an increase in the content of short side chains with a DP of 6 to 22 by at least 5%, preferably by at least 10%, in particular by at least 15% and especially preferably by at least 30% in comparison with the amount of short side chains with a DP of 16 to 22 of amylopectin from wild-type plants.

The amount of short side chains is determined via determining the percentage of a specific side chain in the total of all side chains. The total of all side chains is determined via determining the total area under the peaks which represent the degrees of polymerization of DP 6 to 26 in the HPLC chromatogram. The percentage of a particular side chain in the total of all side chains is determined via determining the ratio of the area under the peak which represents this side chain in the HPLC chromatogram to the total area. A programme which may be used for determining the peak areas is, for example, Chromelion 6.20 from Dionex, USA.

In a further embodiment of the present invention, the modified starch synthesized in the plant cells according to the invention is distinguished not only by an increased amylose content in comparison with starch from corresponding wild-type plants and an increased phosphate content and an increased final viscosity in the RVA analysis, but also by a modified "side chain profile DP 12 to 18" and/or by a modified "side chain profile DP 19 to 24" and/or by a modified "side chain profile DP 25 to 30" and/or by a modified "side chain profile DP 37 to 42" and/or by a modified "side chain profile DP 62 to 123".

In connection with the present invention, the term modified "side chain profile DP 12 to 18" is understood as meaning a reduction of the amount of amylopectin side chains with a DP of 12 to 18 by at least 25%, preferably by at least 35%, especially preferably by at least 45% and very especially preferably by at least 55% in comparison with the amount of amylopectin side chains with a DP of 12 to 18 from wild-type plants.

In connection with the present invention, the term modified "side chain profile DP 19 to 24" is understood as meaning a reduction of the amount of amylopectin side chains with a DP of 19 to 24 by at least 10%, preferably by at least 20% and especially preferably by at least 30% in comparison with the amount of amylopectin side chains with a DP of 19 to 24 from wild-type plants.

In connection with the present invention, the term modified "side chain profile DP 25 to 30" is understood as meaning a reduction of the amount of amylopectin side chains with a DP of 25 to 30 by at least 5% in comparison with the amount of amylopectin side chains with a DP of 25 to 30 from wild-type plants.

In connection with the present invention, the term modified "side chain profile DP 37 to 42" is understood as meaning an increase of the amount of amylopectin side chains with a DP of 37 to 42 by at least 5%, preferably by at least 10% and especially preferably by at least 15% in comparison with the amount of amylopectin side chains with a DP of 37 to 42 from wild-type plants.

In connection with the present invention, the term modified "side chain profile DP 62 to 123" is understood as meaning an increase of the amount of amylopectin side chains with a DP of 62 to 123 by at least 20%, preferably by at least 35%, especially preferably by at least 50% in comparison with the amount of amylopectin side chains with a DP of 62 to 123 from wild-type plants.

The side chain profile is determined via determining the percentage of a specific group of side chains in the total of all side chains in the GPC chromatogram. To this end, the total area under the line of the GPC chromatogram is divided into individual segments, each of which represents groups of side chains of different lengths. The chosen segments contain side chains with the following degree of polymerization (DP=number of glucose monomers within one side chain): DP<11, DP12-18, DP19-24, DP25-30, DP31-36, DP37-42, DP43-48, DP49-55, DP56-61 and DP62-123. To elution volume with the molecular mass, the GPC column used is calibrated with dextran standards (Fluka, Product# 31430). The dextrans used, their associated molecular mass and the elution volumes are shown in FIG. 9. Using the resulting calibration graph, the elution diagram is shown as a molecular weight distribution. To determine the molecular weight of the individual side chains, a molecular weight of 162 was set for glucose. The total area under the line in the GPC chromatogram is set as 100% and the percentage of the areas of the individual segments is calculated based on the percentage of the total area.

In a further especially preferred embodiment, the amylopectin of starch according to the invention, from plant cells according to the invention or plants according to the invention, shows an increased amount of the amylopectin side chains with a DP of greater than 123 in comparison with the amount of side chains with a DP of greater than 123 from amylopectin of wild-type plants.

The plant cells according to the invention may be used for the regeneration of intact plants.

The plants obtainable by regeneration of the transgenic plant cells according to the invention are likewise subject-matter of the present invention.

The plant cells according to the invention may belong to any plant species, i.e. to both monocotyledonous and dicotyledonous plants. They are preferably plant cells of agricultural useful plants, i.e. plants which are grown by man for the purposes of nutrition or for technical, in particular industrial, purposes. The invention preferably relates to fibre-forming plants (for example flax, hemp, cotton), oil-storing plants (for example oilseed rape, sunflower, soybean), sugar-storing plants (for example sugar beet, sugar cane, sugar millet) and protein-storing plants (for example legumes).

In a further preferred embodiment, the invention relates to fodder plants, in particular to fodder grasses and forage grasses (alfalfa, clover and the like) and vegetable plants (for example tomato, lettuce, chicory).

In a further preferred embodiment, the invention relates to plant cells from starch-storing plants (for example wheat, barley, oats, rye, potato, maize, rice, pea, cassava), with plant cells from potato being especially preferred.

A multiplicity of techniques are available for introducing DNA into a plant host cell. These techniques encompass the transformation of plant cells with T-DNA using *Agrobacterium tumefaciens* or *Agrobacterium rhizogenes* as transformation agent, the fusion of protoplasts, injection, the electroporation of DNA, the introduction of the DNA by means of the biolistic approach, and other possibilities.

The use of the agrobacteria-mediated transformation of plant cells has been studied intensively and described sufficiently in EP 120516; Hoekema, Ind.: The Binary Plant Vector System Offsetdrukkerij Kanters B.V., Alblasserdam (1985), Chapter V; Fraley et al., Crit. Rev. Plant Sci. 4, 1-46 and in An et al. EMBO J. 4, (1985), 277-287. As regards the transformation of potato, see, for example, Rocha-Sosa et al., EMBO J. 8, (1989), 29-33.).

The transformation of monocotyledonous plants by means of vectors based on transformation with agrobacterium has also been described (Chan et al., Plant Mol. Biol. 22, (1993), 491-506; Hiei et al., Plant J. 6, (1994) 271-282; Deng et al, Science in China 33, (1990), 28-34; Wilmink et al., Plant Cell Reports 11, (1992), 76-80; May et al., Bic)/Technology 13, (1995), 486-492; Conner and Domisse, Int. J. Plant Sci. 153 (1992), 550-555; Ritchie et al, Transgenic Res. 2, (1993), 252-265). An alternative system for the transformation of monocotyledonous plants is the transformation by means of the biolistic approach (Wan and Lemaux, Plant Physiol. 104, (1994), 37-48; Vasil et al., Bio/Technology 11 (1993), 1553-1558; Ritala et al., Plant Mol. Biol. 24, (1994), 317-325; Spencer et al., Theor. Appl. Genet. 79, (1990), 625-631), protoplast transformation, the electroporation of partially permeabilized cells, the introduction of DNA by means of glass fibres. In particular the transformation of maize has been described repeatedly in the literature (cf., for example, WO95/06128, EP0513849, EP0465875, EP0292435; Fromm et al., Biotechnology 8, (1990), 833-844; Gordon-Kamm et al., Plant Cell 2, (1990), 603-618; Koziel et al., Biotechnology 11 (1993), 194-200; Moroc et al., Theor. Appl. Genet. 80, (1990), 721-726).

The successful transformation of other cereal species has also been described, for example for barley (Wan and Lemaux, see above; Ritala et al., see above; Krens et al., Nature 296, (1982), 72-74) and wheat (Nehra et al., Plant J. 5, (1994), 285-297). All of the abovementioned methods are suitable for the purposes of the present invention.

Any promoter which is active in plant cells is generally suitable for the expression of the foreign nucleic acid molecule(s). The promoter may be chosen in such a way that expression in the plants according to the invention takes place constitutively or only in a specific tissue, at a particular point in time of plant development or at a point in time determined by external factors. As regards the plant, the promoter may be homologous or heterologous.

In a further embodiment of the invention, at least one antisense RNA is expressed in plant cells in order to reduce the activity of one or more SSIII proteins and/or BEI proteins and/or BEII proteins.

The present invention therefore also relates to a plant cell according to the invention, wherein said foreign nucleic acid molecules are selected from the group consisting of a) DNA molecules encoding at least one antisense RNA which brings about a reduction of the expression of at least one endogenous gene encoding SSIII proteins and/or BEI proteins and/or BEII proteins;

b) DNA molecules which, via a cosuppression effect, lead to a reduction of the expression of at least one endogenous gene encoding SSIII protein(s) and/or BEI protein(s) and/or BEII protein(s);

c) DNA molecules encoding at least one ribozyme which specifically cleaves transcripts of at least one endogenous gene encoding SSIII proteins and/or BEI proteins and/or BEII proteins; and d) Nucleic acid molecules introduced by means of in-vivo mutagenesis which lead to a mutation or insertion of a heterologous sequence in at least one endogenous gene encoding SSIII protein(s) and/or BEI protein(s) and/or BEII protein(s), the mutation or insertion bringing about a reduction of the expression of at least one gene encoding SSIII protein(s) and/or BEI protein(s) and/or BEII protein(s), or the synthesis of inactive SSIII and/or BEI and/or BEII proteins;

e) DNA molecules which simultaneously encode at least one antisense RNA and at least one sense RNA, where said antisense RNA and said sense RNA form a double-stranded RNA molecule which brings about a reduction of the expression of at least one endogenous gene encoding SSIII protein(s) and/or BEI protein(s) and/or BEII protein(s);

f) DNA molecules containing transposons, the integration of the transposon sequences leading to a mutation or an insertion in at least one endogenous gene encoding SSIII protein(s) and/or BEI protein(s) and/or BEII protein(s) which brings about a reduction of the expression of at least one gene encoding an SSIII protein(s) and/or BEI protein(s) and/or BEII protein(s), or which results in the synthesis of inactive SSIII and/or BEI and/or BEII proteins; and g) T-DNA molecules which, owing to the insertion into at least one endogenous gene encoding SSIII protein(s) and/or BEI protein(s) and/or BEII protein(s), brings about a reduction of the expression of at least one endogenous gene encoding SSIII protein(s) and/or BEI protein(s) and/or BEII protein(s), or which result in the synthesis of inactive SSIII and/or BEI and/or BEII proteins.

In a further aspect, the present invention relates to any kind of propagation material of plants according to the invention.

A further aspect of the present invention relates to the use of the nucleic acid molecules described herein for the generation of the plant cells and plants according to the invention.

A further aspect of the present invention relates to a composition comprising at least one of the above nucleic acid molecules, where the at least one nucleic acid molecule, after introduction into a plant cell, leads to the reduction of at least one SSIII protein which occurs endogenously in the plant cell and at least one BEII protein which occurs endogenously in the plant cell and preferably furthermore to the reduction of at least one BEI protein which occurs endogenously in the plant cell. The composition may comprise one or more nucleic acid constructs (cf. above).

A further aspect of the present invention relates to the use of the compositions according to the invention for the generation of the plant cells and plants according to the invention, and to a host cell, in particular a plant cell, containing the composition according to the invention.

Yet a further aspect of the present invention relates to a transformation system in plant cells, comprising at least one nucleic acid molecule and at least one plant cell, where the at least one nucleic acid molecule leads to the reduction of the activity of in each case at least one of the SSIII, BEI and BEII proteins which occur endogenously in the plant cell unless the activity of these proteins has been reduced already by an existing genetic modification of said plant cell. For the purposes of the present invention, "transformation system" thus relates to a combination of at least one plant cell to be transformed and at least one nucleic acid molecule as described above which is used for the transformation. Further components with which the skilled worker in the field of the transformation of plant cells is familiar and which are required in the transformation process, including buffers and the like, may be present in the transformation system according to the invention.

(RB, left T-DNA border, LB, right T-DNA border; CaMV35, cauliflower mosaic virus 35S promoter; NOS, polyadenylation sequence of the *Agrobacterium tumefaciens* nopaline synthase gene; OCS, polyadenylation sequence of the *Agrobacterium tumefaciens* octopine synthase gene; B33, promoter of the potato patatin gene; BEII, coding sequences of the potato BEII gene; bar, sequence encoding a *Streptomyces hygroscopicus* phosphinothricin acetyltransferase).

Figure 7:
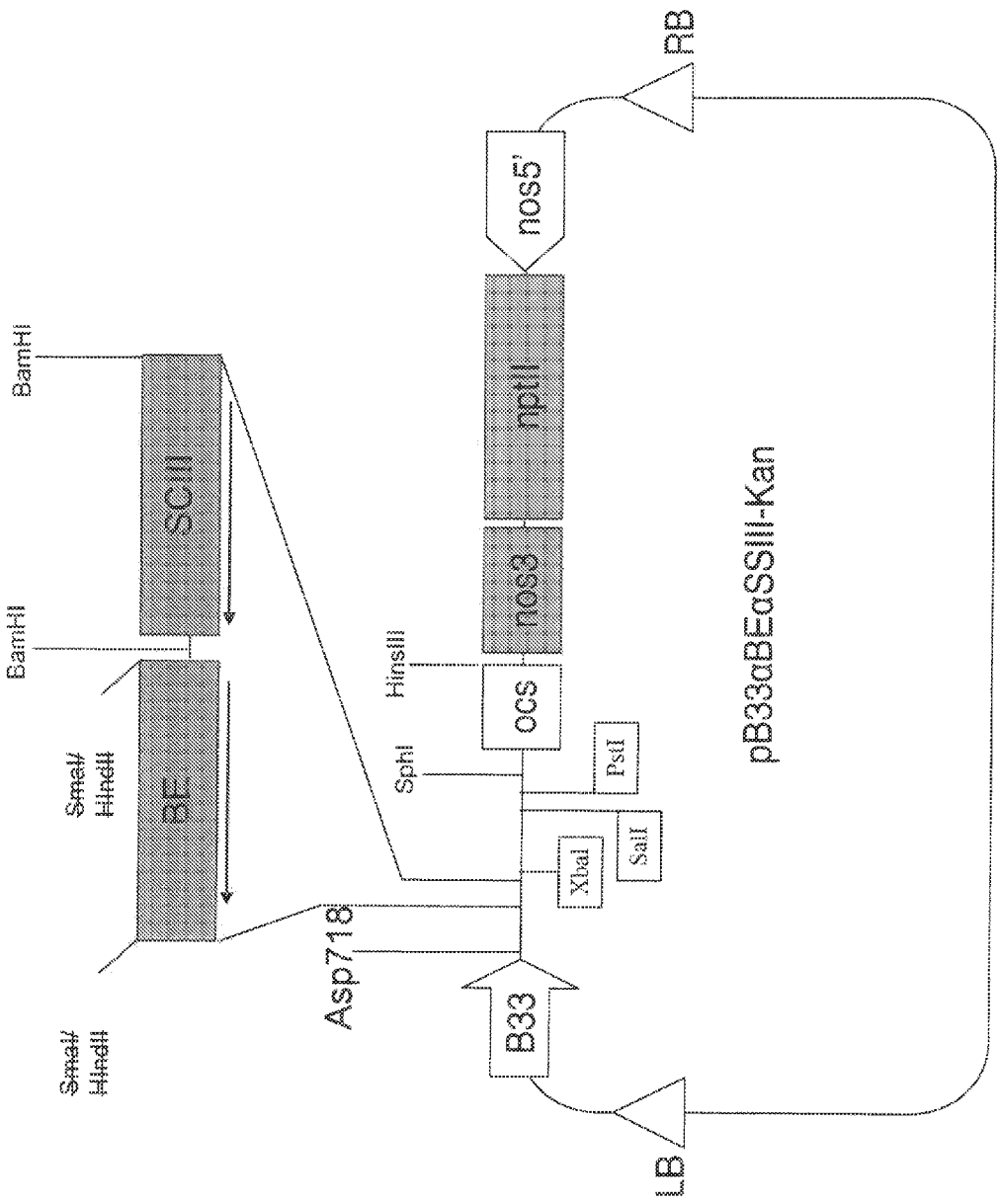

FIG. 7:
Schematic representation of the vector pB33-α-BE-α-SSIII-Kan, which was used for the generation of transgenic plants with a reduced activity of an SSIII protein and a BEI protein (RB, left T-DNA border, LB, right T-DNA border; nos5', promoter of the *Agrobacterium nopaline* synthase gene; nptII, gene encoding the activity of a neomycin phosphotransferase; nos3, polyadenylation sequence of the *Agrobacterium tumefaciens* nopaline synthase gene; OCS, polyadenylation sequence of the *Agrobacterium tumefaciens* octopine synthase gene; B33, promoter of the potato patatin gene; BE, coding sequences of the potato BEI gene; SSIII, coding sequences of the potato SSIII gene).

Figure 8:
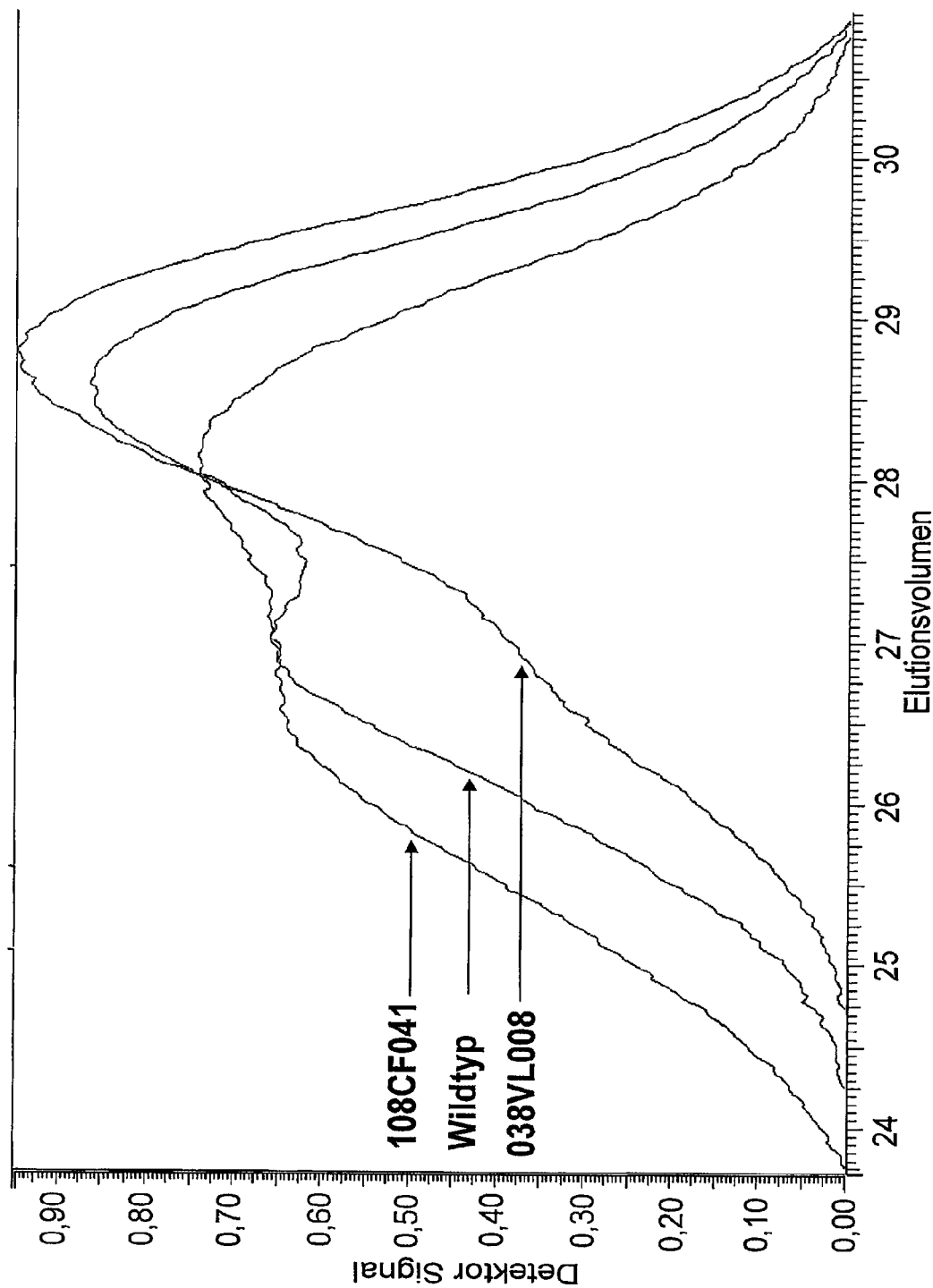

FIG. 8
The figure shows the entire elution diagram of the amylopectin from starches of lines 038VL008, 108CF041 and wild type. As shown in the figure, the amount of bigger side chains in line 108CF041 is markedly higher in contrast to the background 038VL008 and/or the corresponding wild type.

Figure 9:
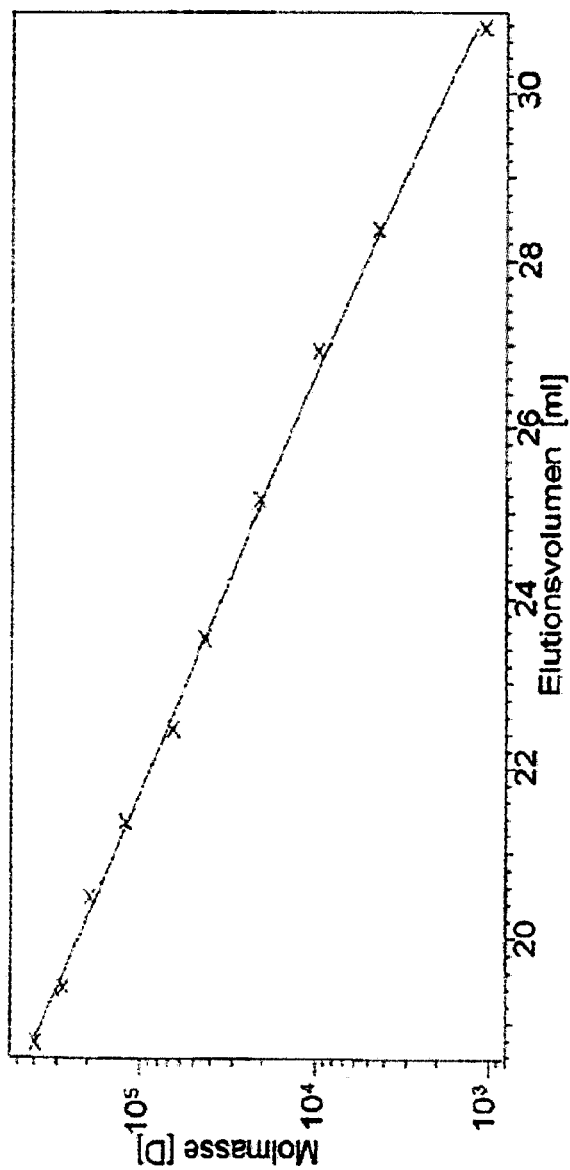

FIG. 9
Calibration curve and table with corresponding dextran standards

Figure 10:
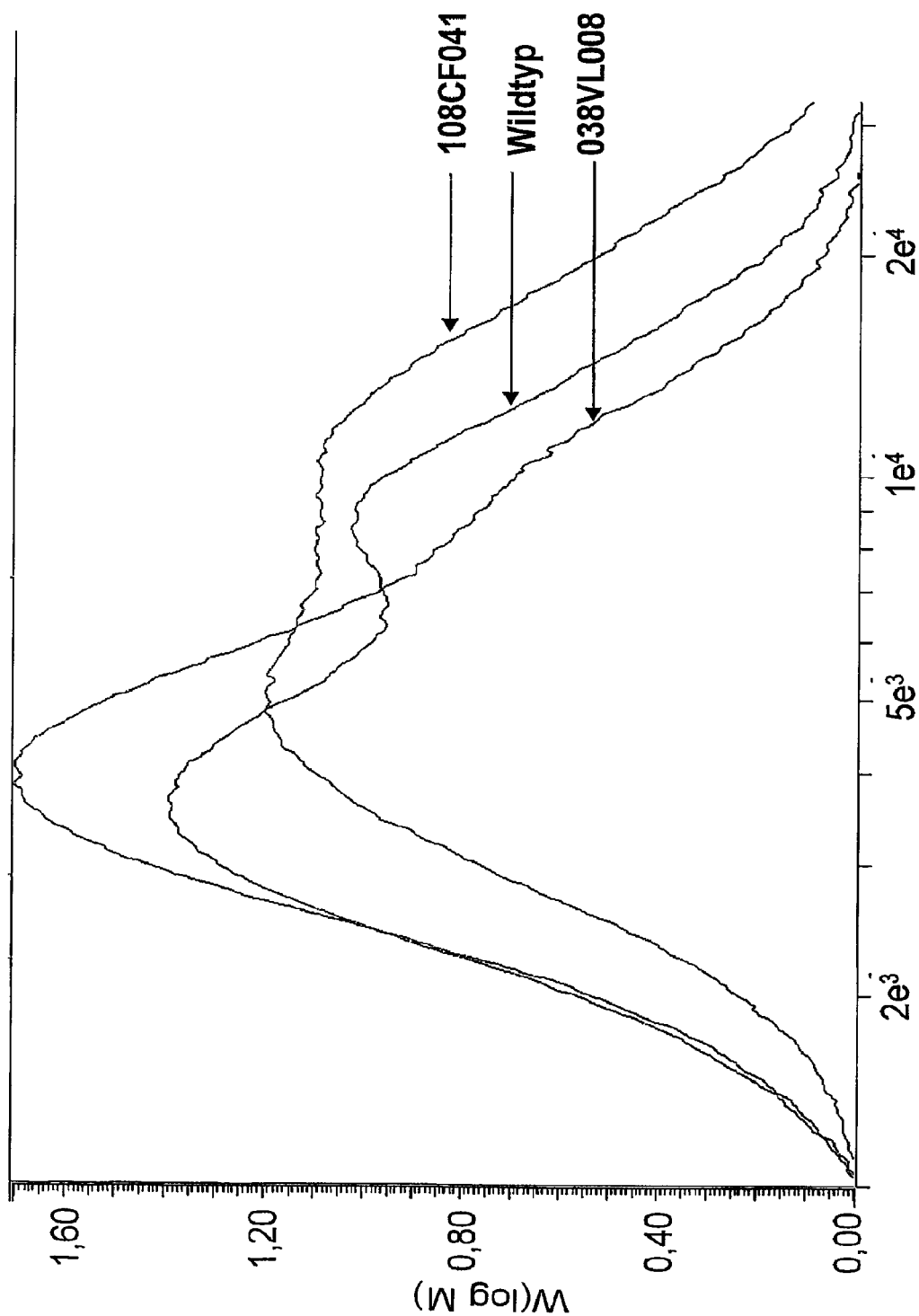

FIG. 10
The figure shows the entire elution diagram of the amylopectin from starches of lines 038VL008, 108CF041 and wild type. In contrast to FIG. 8, the x axis does not show the elution volume, but the molecular weight. The elution diagram of FIG. 8 as a function of the molecular weight distribution is shown with the aid of the calibration graph of FIG. 9.

Figure 11:
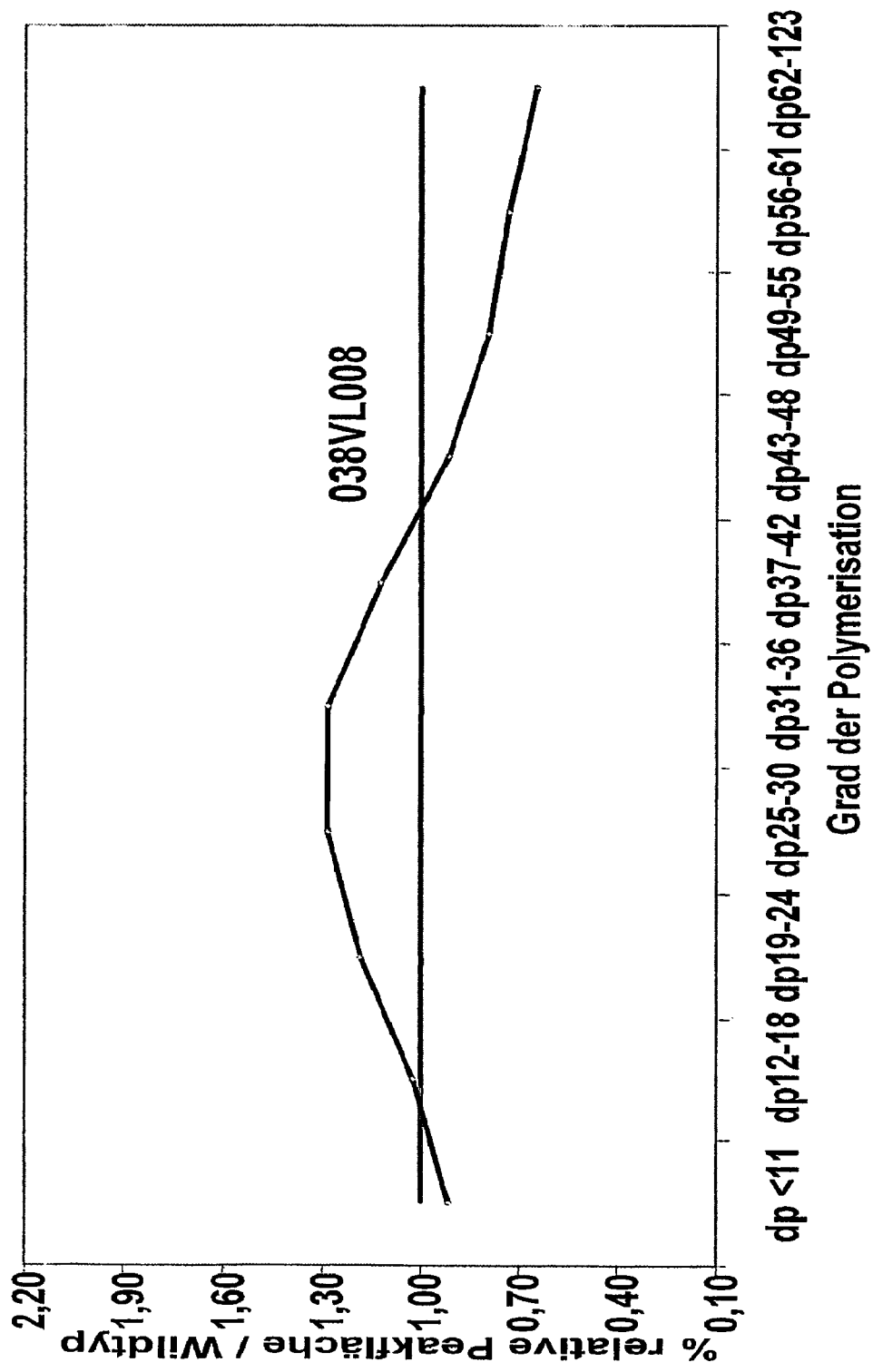

FIG. 11
This represents the side chain profile distribution of the amylopectin from plants of line 038VL008 in comparison with the side chain profile of amylopectin from wild-type plants.

Figure 12:
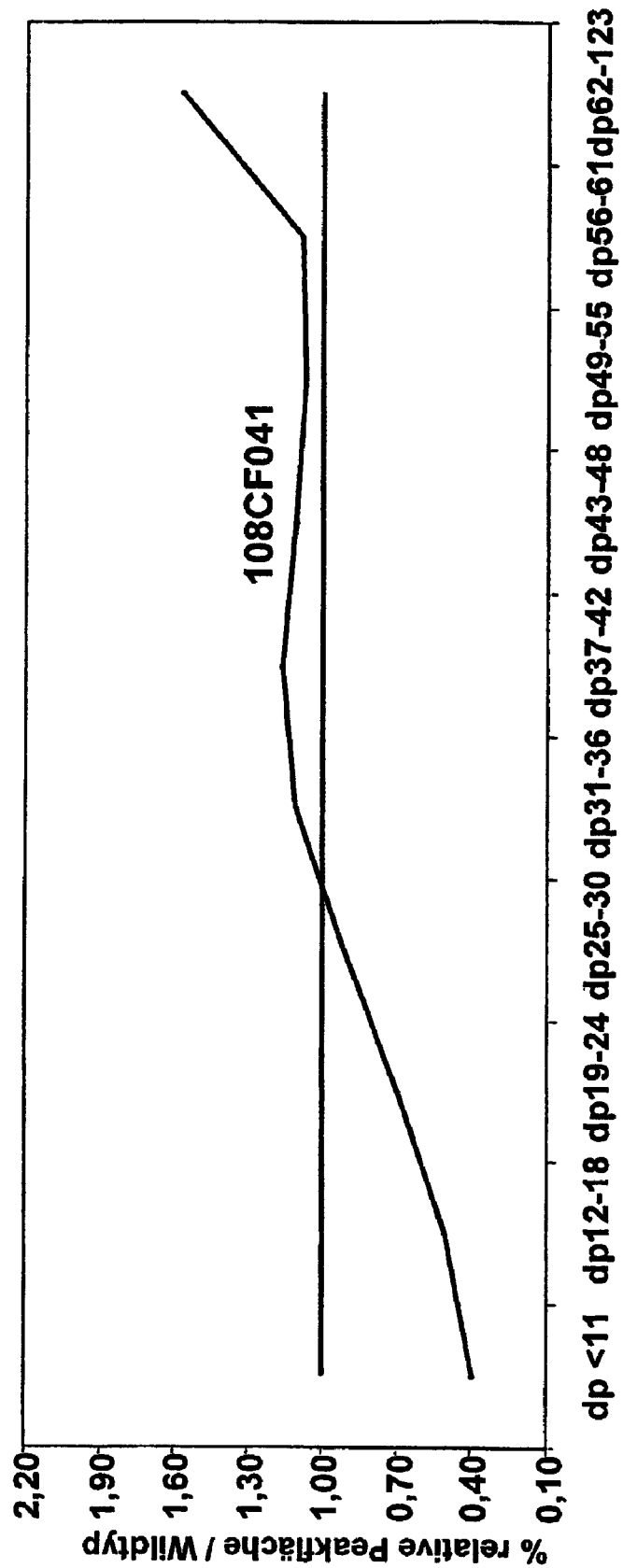

FIG. 12
This represents the side chain profile distribution of the amylopectin from plants of line 108CF041 in comparison with the side chain profile of amylopectin from wild-type plants.

DESCRIPTION OF THE SEQUENCES

Seq ID 1:
Nucleic acid sequence of the potato (*Solanum tuberosum*) starch synthase SSIII with indication of the sequences which encode the corresponding SSIII protein.

Seq ID 2:
Amino acid sequence of a potato SSIII protein.

Seq ID 3:
Amino acid sequence of the Pfam cbm25 binding domain of the potato SSIII protein (*Solanum tuberosum*).

Seq ID 4:
Coding nucleic acid sequence of the potato (*Solanum tuberosum*) branching enzyme BEI.

Seq ID 5:
Amino acid sequence of the potato (*Solanum tuberosum*) branching enzyme BEI.

Seq ID 6:
Coding nucleic acid sequence of the potato (*Solanum tuberosum*) branching enzyme BEII.

Seq ID 7:
Amino acid sequence of the potato (*Solanum tuberosum*) branching enzyme BEII.

Seq ID 8:
PCR-amplified nucleic acid sequence of the potato (*Solanum tuberosum*) branching enzyme BEII.

General Methods

The following methods were used in the examples:

Starch Analysis a) Determination of the Amylose Content and of the Amylose/Amylopectin Ratio Starch was isolated from potato plants by standard methods, and the amylose content and the amylose:amylopectin ratio was determined by the method described by Hovenkamp-Hermelink et al. (Potato Research 31, (1988), 241-246).

b) Determination of the Phosphate Content

In starch, the positions C2, C3 and C6 of the glucose units can be phosphorylated. To determine the C6-P content of starch, 50 mg of starch are hydrolysed for 4 h at 95° C. in 500 µl of 0.7 M HCl. The samples are then centrifuged for 10 minutes at 15 500 g and the supernatants are removed. 7 µl of the supernatants are mixed with 193 µl of imidazole buffer (100 mM imidazole, pH 7.4; 5 mM $MgCl_2$, 1 mM EDTA and 0.4 mM NAD). The measurement was carried out in a photometer at 340 nm. After the base absorption had been established, the enzyme reaction was started by addition of 2 units glucose-6-phosphate dehydrogenase (from Leuconostoc mesenteroides, Boehringer Mannheim). The change in absorption is directly proportional to the concentration of the G-6-P content of the starch.

The total phosphate content was determined by the method of Ames (Methods in Enzymology VIII, (1966), 115-118).

Approximately 50 mg of starch are treated with 30 µl of ethanolic magnesium nitrate solution and ashed for 3 hours at 500° C. in a muffle oven. The residue is treated with 300 µl of 0.5 M hydrochloric acid and incubated for 30 minutes at 60° C. One aliquot is subsequently made up to 300 µl 0.5 M hydrochloric acid and this is added to a mixture of 100 µl of 10% ascorbic acid and 600 µl of 0.42% ammonium molybdate in 2 M sulphuric acid and incubated for 20 minutes at 45° C.

This is followed by a photometric determination at 820 nm with a phosphate calibration series as standard.

c) Determination of the Gel Strength (Texture Analyser)

1.5 g of starch (DM) are gelatinized in the RVA apparatus in 25 ml of an aqueous suspension (temperature programme: see item d) "Determination of the viscosity characteristics by means of a Rapid Visco Analyser (RVA)") and subsequently stored for 24 hours at room temperature in a sealed container. The samples are fixed under the probe (round piston with planar surface) of a Texture Analyser TA-XT2 from Stable Micro Systems (Surrey, UK) and the gel strength was determined using the following parameters:

| | |
|---|---|
| Test speed | 0.5 mm/s |
| Depth of penetration | 7 mm |
| Contact surface | 113 mm² |
| Pressure | 2 g | d) Determination of the Viscosity Characteristics by Means of a Rapid Visco Analyser (RVA)

Standard Method 2 g of starch (DM) are taken up in 25 ml of $H_2O$ (VE-type water, conductivity of at least 15 mega ohm) and used for the analysis in a Rapid Visco Analyser (Newport Scientific Pty Ltd., Investmet Support Group, Warriewod NSW 2102, Australia). The apparatus is operated following the manufacturer's instructions. The viscosity values are indicated in RVUs in accordance with the manufacturer's operating manual, which is incorporated into the description herewith by reference. To determine the viscosity of the aqueous starch solution, the starch suspension is first heated for one minute at 50° C. (step 1), and then heated from 50° C. to 95° C. at a rate of 12° C. per minute (step 2). The temperature is then held for 2.5 minutes at 95° C. (step 3). Then, the solution is cooled from 95° C. to 50° C. at a rate of 12° C. per minute (step 4). The viscosity is determined during the entire duration.

In particular in those cases where the limits of the measuring range of the RVA were insufficient when 2.0 g (DM) of starch in 25 ml of $H_2O$ (VE-type water, conductivity of at least 15 mega ohm) were weighed in, only 1.5 g of starch (DM) were taken up in 25 ml of $H_2O$ (VE-type water, conductivity of at least 15 mega ohm).

For reasons of comparison with the prior art, a modified temperature profile was additionally used in some cases.

The following temperature profiles were used:

RVA Analytical Method 1:

To determine the viscosity of a 6% aqueous starch solution, the starch suspension is first stirred for 10 seconds at 960 rpm and subsequently heated at 50° C. at a stirring speed of 160 rpm, initially for a minute (step 1). The temperature was then raised from 50° C. to 95° C. at a heating rate of 12° C. per minute (step 2). The temperature is held for 2.5 minutes at 95° C. (step 3) and then cooled from 95° C. to 50° C. at 12° C. per minute (step 4). In the last step (step 5), the temperature of 50° C. is held for 2 minutes.

After the programme has ended, the stirrer is removed and the beaker covered. The gelatinized starch is now available for the texture analysis after 24 hours.

RVA Analytical Method 2:

To determine the viscosity of a 6% aqueous starch solution, the starch suspension is first stirred for 10 seconds at 960 rpm and subsequently heated at 50° C. at a stirring speed of 160 rpm, initially for two minutes (step 1). The temperature was then raised from 50° C. to 95° C. at a heating rate of 1.5° C. per minute (step 2). The temperature is held for 15 minutes at 95° C. (step 3) and then cooled from 95° C. to 50° C. at 1.5° C. per minute (step 4). In the last step (step 5), the temperature of 50° C. is held for 15 minutes.

After the programme has ended, the stirrer is removed and the beaker covered. The gelatinized starch is now available for the texture analysis after 24 hours.

RVA Analytical Method 3:

To determine the viscosity of a 10% aqueous starch solution, the starch suspension is first stirred for 10 seconds at 960 rpm and subsequently heated at 50° C. at a stirring speed of 160 rpm, initially for two minutes (step 1). The temperature was then raised from 50° C. to 95° C. at a heating rate of 1.5° C. per minute (step 2). The temperature is held for 15 minutes at 95° C. (step 3) and then cooled from 95° C. to 50° C. at 1.5° C. per minute (step 4). In the last step (step 5), the temperature of 50° C. is held for 15 minutes. This profile of the RVA analysis corresponds to the one employed in WO 9634968.

After the programme has ended, the stirrer is removed and the beaker covered. The gelatinized starch is now available for the texture analysis after 24 hours.

The profile of the RVA analysis contains parameters which are shown for the comparison of different measurements and substances. In the context of the present invention, the following terms are to be understood as follows:

1. Maximum Viscosity (RVA Max)

The maximum viscosity is understood as meaning the highest viscosity value, measured in RVUs, obtained in step 2 or 3 of the temperature profile.

2. Minimum Viscosity (RVA Min)

The minimum viscosity is understood as meaning the lowest viscosity value, measured in RVUs, observed in the temperature profile after the maximum viscosity. Normally, this takes place in step 3 of the temperature profile.

3. Final Viscosity (RVA Fin)

The final viscosity is understood as meaning the viscosity value, measured in RVUs, observed at the end of the measurement.

4. Setback (RVA Set)

What is known as the "setback" is calculated by subtracting the value of the final viscosity from that of the minimum occurring after the maximum viscosity in the curve.

5. Gelatinization Temperature (RVA T)

The gelatinization temperature is understood as meaning the point in time of the temperature profile where, for the first time, the viscosity increases drastically for a brief period.

e) Analysis of the Side-Chain Distribution of the Amylopectin by Means of Ion-Exchange Chromatography To separate amylose and amylopectin, 200 mg of starch are dissolved in 50 ml reaction vessels, using 12 ml of 90% (v/v) DMSO in $H_2O$. After addition of 3 volumes of ethanol, the precipitate is separated by centrifugation for 10 minutes at about 1800 g at room temperature (RT). The pellet is then washed with 30 ml of ethanol, dried and dissolved in 40 ml of 1% (w/v) NaCl solution at 75° C. After the solution has cooled to 30° C., approximately 90 mg of thymol are added slowly, and this solution is incubated for at least 60 h at 30° C. The solution is then centrifuged for 30 minutes at 2000 g (RT). The supernatant is then treated with 3 volumes of ethanol, and the amylopectin which settles out is separated by centrifugation for 5 minutes at 2000 g (RT).

The pellet (amylopectin) is then washed with ethanol and dried using acetone. By addition of DMSO to the pellet, one obtains a 1% solution, of which 200 μl are treated with 345 μl of water, 10 μl of 0.5 M sodium acetate (pH 3.5) and 5 μl of isoamylase (dilution 1:10; Megazyme) and incubated for about 16 hours at 37° C. A 1:5 aqueous dilution of this digest is subsequently filtered through a 0.2 μm filter, and 100 μl of the filtrate are analysed by ion chromatography (HPAEC-PAD, Dionex). Separation was performed using a PA-100 column (with suitable precolumn), while detection was performed amperometrically. The elution conditions were as follows:

Solution A—0.15M NaOH
Solution B—1 M sodium acetate in 0.15M NaOH

TABLE 1

Composition of the elution buffer for the side chain analysis of the amylopectin at different times during the HPEAC-PAD Dionex analysis. Between the times stated, the composition of the elution buffer changes in each case linearly.

| t (min) | Solution A (%) | Solution B (%) |
|---------|----------------|----------------|
| 5       | 0              | 100            |
| 35      | 30             | 70             |
| 45      | 32             | 68             |
| 60      | 100            | 0              |
| 70      | 100            | 0              |
| 72      | 0              | 100            |
| 80      | 0              | 100            |
| Stop    |                |                |

The determination of the relative amount of short side chains in the total of all side chains is carried out via the determination of the percentage of a particular side chain in the total of all side chains. The total of all side chains is determined via the determination of the total area under the peaks which represent the polymerization degrees of DP6 to 26 in the HPCL chromatogram.

The percentage of a particular side chain in the total of all side chains is determined via the determination of the ratio of the area under the peak which represents this side chain in the HPLC chromatogram to the total area. The programme Chromelion 6.20 Version 6.20 from Dionex, USA, was used for determining the peak areas.

f) Granule Size Determination

Starch was extracted from potato tubers by standard methods (see Examples). The granule size determination was then carried out using a photosedimentometer of type "Lumosed FS1" from Retsch GmbH, Germany, using the software V.2.3. The software settings were as follows:

| Substance data: | Calibration No. | 0 |
|---|---|---|
| | Density [kg/m$^3$] | 1500 |
| Sedimentation fluid: | Type | Water |
| | Viscosity [Pa s] | 0.001 |
| | Density [kg/m$^3$] | 1000 |
| | Addition | — |
| | Recordings | 5 min |
| | Cut-off [μm] | 250 |
| | Passage [%] | 100 |
| | Measuring range | 4.34-117.39 μm |
| | Calibration | N |
| | Temperature | 20° C. |

The granule size distribution was determined in aqueous solution and was carried out following the manufacturer's instructions and on the basis of the literature by, for example, H. Pitsch, Korngrößenbestimmung [granule size determination]; LABO-1988/3 Fachzeitschrift für Labortechnik, Darmstadt.

g) Scanning Electron Micrographs (SEM)

To study the surface of the starch samples, the latter were dusted onto the sample holder using a conductive adhesive. To avoid charging, the sample holders were finally sputtered with a 4 nm Pt coating. The starch samples were studied using the field emission scanning electron microscope JSM 6330 F (Jeol) at an accelerating voltage of 5 kV.

h) Determination of the Activity of the SSIII, BEI and BEII Proteins

These were carried out as specified in the examples.

Examples

Generation of the Expression Vector ME5/6 pGSV71 is a derivative of the plasmid pGSV7, which is derived from the intermediary vector pGSV1. pGSV1 is a derivative of pGSC1700, whose construction has been described by Cornelissen and Vanderwiele (Nucleic Acid Research 17, (1989), 19-25). pGSV1 was obtained from pGSC1700 by deleting the carbenicillin resistance gene and deleting the T-DNA sequences of the TL-DNA region of the plasmid pTiB6S3.

pGSV7 contains the replication origin of the plasmid pBR322 (Bolivar et al., Gene 2, (1977), 95-113) and the replication origin of the *Pseudomonas* plasmid pVS1 (Itoh et al., Plasmid 11, (1984), 206). pGSV7 additionally contains the selectable marker gene aadA, from the *Klebsiella pneumoniae* transposon Tn1331, which confers resistance to the antibiotics spectinomycin and streptomycin (Tolmasky, Plasmid 24 (3), (1990), 218-226; Tolmasky and Crosa, Plasmid 29(1), (1993), 31-40)

The plasmid pGSV71 was obtained by cloning a chimeric bar gene between the border regions of pGSV7. The chimeric bar gene contains the cauliflower mosaic virus promoter sequence for transcriptional initiation (Odell et al., Nature 313, (1985), 180), the *Streptomyces hygroscopicus* bar gene (Thompson et al., Embo J. 6, (1987), 2519-2523) and the 3'-untranslated region of the pTiT37 T-DNA nopalin synthase gene for transcriptional termination and for polyadenylation. The bar gene confers tolerance to the herbicide glufosinate-ammonium.

The T-DNA contains the right border sequence of the TL-DNA from the plasmid pTiB6S3 (Gielen et al., EMBO J. 3, (1984), 835-846) at position 198-222. A polylinker sequence is located between nucleotide 223-249. The nucleotides 250-1634 contain the cauliflower mosaic virus p35S3 promoter region (Odell et al., see above). The coding sequence of the *Streptomyces hygroscopicus* phosphinothricin resistance gene (bar) (Thompson et al. 1987, see above) is arranged between the nucleotides 1635-2186. The two terminal codons at the 5' end of the bar wild-type gene were replaced by the codons ATG and GAC. A polylinker sequence is located between the nucleotides 2187-2205. The 260 by TaqI fragment of the untranslated 3' end of the nopalin synthase gene (3'nos) from the T-DNA of the plasmid pTiT37 (Depicker et al., J. Mol. Appl. Genet. 1, (1982), 561-573) is located between the nucleotides 2206 and 2465. The nucleotides 2466-2519 contain a polylinker sequence. The left border sequence of the pTiB6S3 TL-DNA (Gielen et al., EMBO J. 3, (1984), 835-846) is located between the nucleotides 2520-2544.

The vector pGSV71 was then cut using the enzyme PstI and made blunt-ended. The B33 promoter and the ocs cassette was then excised from the vector pB33-Kan in the form of an EcoRI-HindIII fragment, made blunt-ended and inserted into the vector pGSV71 which had been cut with PstI and made blunt-ended. The resulting vector was used as starting vector for the construction of ME5/6: An oligonucleotide containing the cleavage sites EcoRI, PacI, SpeI, SrfI, SpeI, NotI, PacI and EcoRI was introduced into the PstI cleavage site of the vector ME4/6 located between the B33 promoter and the ocs element, duplicating the PstI cleavage site. The resulting expression vector was termed ME5/6.

Description of the Vector pSK-Pac:

pSK-Pac is a derivative of pSK-Bluescript (Stratagene, USA) in which a PacI cleavage site was introduced at each flank of the multiple cloning site (MCS).

Generation of Transgenic Potato Plants with a Reduced Gene Expression of a BEI, SSIII and BEII Gene To generate transgenic plants with a reduced activity of a BEI, an SSIII and a BEII protein, transgenic plants with a reduced activity of a BEI and an SSIII protein were generated in a first step. To this end, the T-DNA of the plasmid pB33-αBEI-αSSIII-Kan was transferred into potato plants with the aid of agrobacteria as described by Rocha-Sosa et al. (EMBO J. 8, (1989), 23-29).

To construct the plasmid pB33-αBEI-αSSIII-Kan (see FIG. 7), the expression vector pBin33-Kan was constructed in a first step. To this end, the promoter of the *Solanum tuberosum* patatin gene B33 (Rocha-Sosa et al., 1989, see above) was ligated in the form of a DraI fragment (nucleotides—1512-+14) into the SstI-cut vector pUC19 (Genbank Acc. No. M77789), whose ends have been made blunt-ended with the aid of T4 DNA polymerase. This gave rise to the plasmid pUC19-B33. The B33 promoter was excised from this plasmid using EcoRI and SmaI and ligated into the suitably cut vector pBinAR. This gave rise to the plant expression vector pBin33-Kan. The plasmid pBinAR is a derivative of the vector plasmid pBin19 (Bevan, Nucl. Acid Research 12, (1984), 8711-8721) and was constructed by Höfgen and Willmitzer (Plant Sci. 66, (1990), 221-230). A 1631 by HindII fragment which contains a partial cDNA encoding the potato BEI enzyme (Kossmann et al., 1991, Mol. & Gen. Genetics 230 (1-2):39-44) was then made blunt-ended and introduced into the vector pBin33, which had previously been cut with SmaI, in antisense orientation with regard to the B33 promoter (promoter of the *Solanum tuberosum* patatin gene B33; Rocha-Sosa et al., 1989). The resulting plasmid was cut open using BamHI. A 1363 by BamHI fragment containing a partial cDNA encoding the potato SSIII enzyme (Abel et al., 1996, loc.cit.) was introduced into the cleavage site, again in antisense orientation with regard to the B33 promoter.

After the transformation, various lines of transgenic potato plants in whose tubers a markedly reduced activity of a BEI and SSIII protein was observed were identified. The plants resulting from this transformation were termed 038VL.

To detect the activity of soluble starch synthases (SSIII) by non-denaturing gel electrophoresis, tissue samples of potato tubers were digested in 50 mM Tris-HCl pH 7.6, 2 mM DTT, 2.5 mM EDTA, 10% glycerol and 0.4 mM PMSF. The electrophoresis was carried out in a MiniProtean II chamber (Bio-RAD). The monomer concentration of the gels, which had a thickness of 1.5 mm, amounted to 7.5% (w/v), and 25 mM Tris-Glycin pH 8.4 acted as the gel and the running buffers. Identical amounts of protein extract were applied and separated for 2 h at 10 mA for each gel.

The activity gels were subsequently incubated in 50 mM Tricine-NaOH pH 8.5, 25 mM potassium acetate, 2 mM EDTA, 2 mM DTT, 1 mM ADP-glucose, 0.1% (w/v) amylopectin and 0.5 M sodium citrate. Glucans formed were stained with Lugol's solution.

The BEI activity was likewise detected with the aid of non-denaturing gel electrophoresis:

To isolate proteins from plants, the sample material was comminuted in liquid nitrogen using a pestle and mortar, taken up in extraction buffer (50 mM sodium citrate, pH 6.5; 1 mM EDTA, 4 mM DTT), centrifuged (10 min, 14,000 g, 4° C.) and then employed directly in the protein concentration measurement following the method of Bradford. Then, 5 to 20 µg of total protein extract (as required) were treated with 4× loading buffer (20% glycerol, 125 mM Tris HCl, pH 6.8) and applied to a BE activity gel. The running buffer (RB) was composed as follows: RB=30.2 g Tris-base, pH 8.0, 144 g glycine per 1 l $H_2O$.

After running of the gel had ended, each of the gels was incubated overnight at 37° C. in 25 ml of "phosphorylase buffer" (25 ml 1M sodium citrate pH 7.0, 0.47 g glucose-1-phosphate, 12.5 mg AMP, 2.5 mg phosphorylase a/b from rabbit). The gels were stained using Lugol's solution.

More in-depth analyses demonstrated that isolated starches from lines 038VL008 and 038VL107, in which both the BEI and the SSIII protein were reduced, showed the highest phosphate content of all independent transformants studied.

Plants of these lines were subsequently transformed with the plasmid pGSV71-αBEII-basta as described by Rocha-Sosa et al. (EMBO J. 8, (1989), 23-29).

Figure 6:
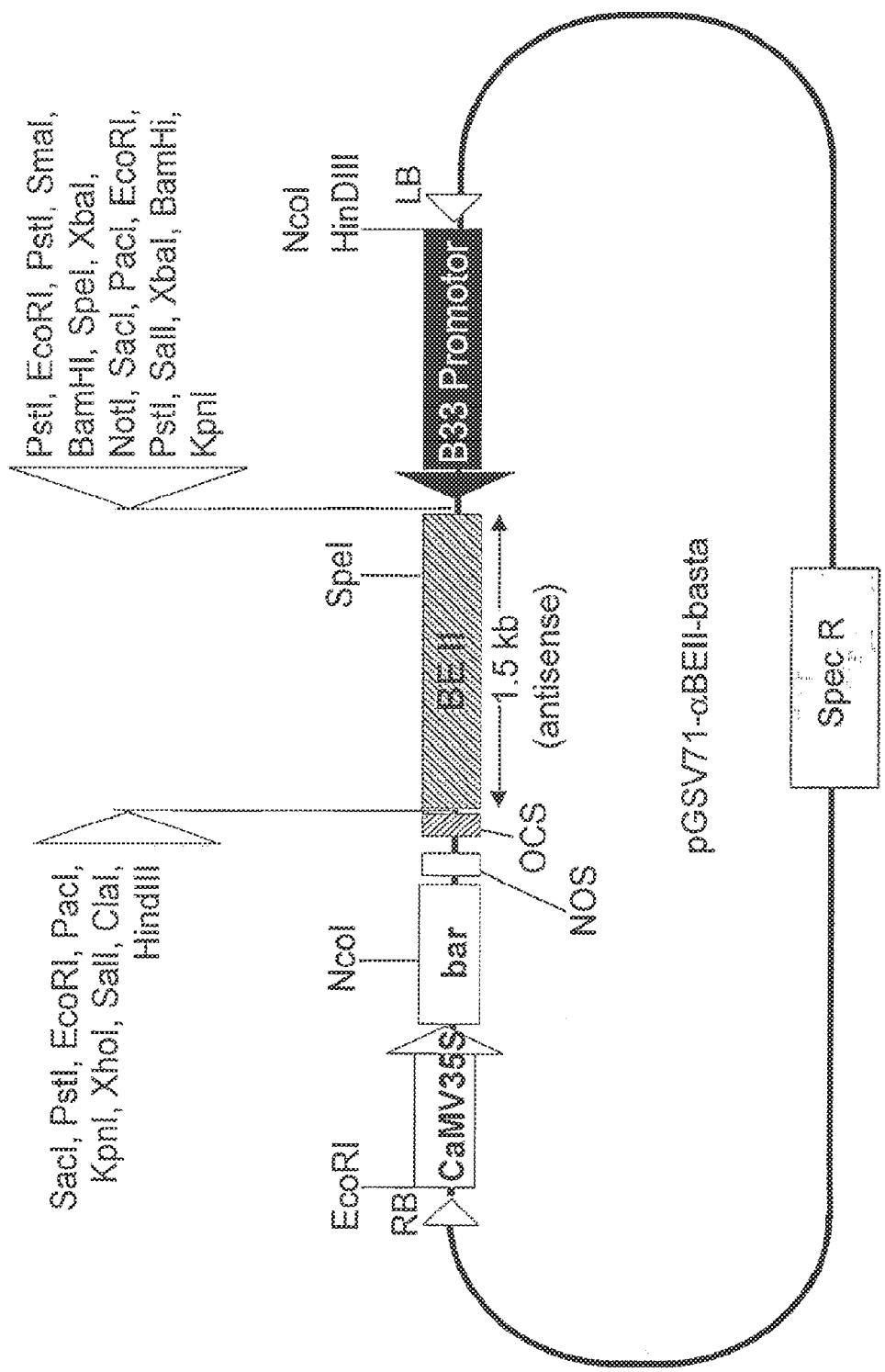
FIG. 6:
Schematic representation of the vector pGSV71-α-BEII-basta, which was used for the retransformation of plants in which a reduced activity of an SSIII protein and of a BEI protein is already observed.

Plasmid pGSV71-αBEII-basta was constructed by screening a tuber-specific potato cDNA library with a DNA fragment amplified using RT-PCR (Primer: 5'-gggggtgttg-gctttgacta (SEQ ID NO: 9) and 5'-cccttctcctcctaatccca (SEQ ID NO: 10); Stratagene ProSTAR™ HF Single-Tube RT-PCR system) with total RNA from tubers as template, following standard methods. In this manner, an approximately 1250 by DNA fragment (SEQ ID No. 8) was isolated and then subcloned into the EcoRV cleavage site of the cloning vector pSK-Pac (see hereinabove) in the form of an EcoRV-SmaI fragment and subsequently ligated into the expression vector ME5/6 in antisense orientation relative to the promoter in the form of a PacI fragment. This gave rise to the plasmid pGSV71-☐BEII-basta (see FIG. 6).

Tuber tissue samples of the independent transformants were obtained from the plants obtained by transformation with the plasmid pGSV71-αBEII-basta, which were referred to as 108CF and 110CF, and their amylose content was determined (see Methods). The starches from the independent lines whose tubers had the highest amylose content were used for a further analysis of the starch characteristics. To prove that in these plants not only the activity of a BEI and SSIII protein is reduced, but also that the activity of a BEII protein is reduced, another analysis was carried out with the aid of non-denaturing gel electrophoresis. The analysis was carried out following the same method as already carried out above for the analysis of the reducing BEI activity, with the exception that the non-denaturing polyacrylamide gel contained 0.5% of maltodextrin (Beba, 15% strength maltodextrin solution for newborns, Nestle) in addition to the above-described composition. The dextrin addition made it possible to show the different activities of the BEI and BEII proteins after incubation of the gels in "phosphorylase buffer" (25 ml 1M sodium citrate pH 7.0, 0.47 g glucose-1-phosphate, 12.5 mg AMP, 2.5 mg phosphorylase a/b from rabbit) overnight at 37° C., followed by staining with Lugol's solution in a gel.

Potato Starch Extraction Process

All tubers of one line (4 to 5 kg) are processed jointly in a commercially available juice extractor (Multipress automatic MP80, Braun). The starch-containing fruit water is collected in a 10-l bucket (ratio bucket height: bucket diameter=approx. 1.1) containing 200 ml of tap water together with a spoon-tipful (approx. 3-4 g) of sodium disulphite. The bucket is subsequently filled completely with tap water. After the starch has been allowed to settle for 2 hours, the supernatant is decanted off, the starch is resuspended in 10 l of tap water and poured over a sieve with a mesh size of 125 μm. After 2 hours (starch has again settled at the bottom of the bucket), the aqueous supernatant is again decanted off. This wash step is repeated 3 more times so that the starch is resuspended a total of 5 times in fresh tap water. Thereafter, the starches are dried at 37° C. to a water content of 12-17% and homogenized using a pestle and mortar. The starches are now available for analyses.

Example 2

Analysis of the Starch from Plants with Reduced BEI, SSIII and BEII Gene Expression The starch from various independent lines of the transformations 108CF and 110CF described in Example 1 were isolated from potato tubers. The physico-chemical properties of this starch were subsequently analysed. The results of the characterization of the modified starches are shown in Table 2 (Tab. 2) for an example of a selection of certain plant lines. The analyses were carried out by the methods described hereinabove.

Tables 2, 3 and 4 which follow summarize the results of the RVA analysis based on starch from wild-type plants:

RVA Analytical Method 1

TABLE 2

Parameters of the RVA analysis of starch isolated from wild-type plants (cv. Desiree), plants with a reduced activity of an SSIII and a BEI protein (038VL008, 038VL107), and of plants with a reduced activity of an SSIII and of a BEI and of a BEII protein (108CF041, 110CF003) in percent based on data of starch of the wild type. The RVA analysis was carried out as described in Analytical method 1.

| | RVA Max (%) | RVA Min (%) | RVA Fin (%) | RVA Set (%) | RVA T (%) | Gel strength |
|---|---|---|---|---|---|---|
| cv. Desiree | 100 | 100 | 100 | 100 | 100 | 100 |
| 038VL008 | 158.7 | 69.8 | 72.0 | 79.5 | 73.0 | 55.4 |
| 108CF041 | 59.6 | 89.9 | 227.5 | 693.7 | 150.2 | 532.3 |
| 038VL107 | 151.1 | 94.3 | 94.0 | 93.0 | 82.2 | 52.2 |
| 110CF003 | 106.4 | 158.6 | 265.0 | 625.7 | 151.5 | 737.1 |

RVA Analytical Method 2

TABLE 3

Parameters of the RVA analysis of starch isolated from wild-type plants (cv. Desiree), plants with a reduced activity of an SSIII and a BEI protein (038VL008, 038VL107), and of plants with a reduced activity of an SSIII and of a BEI and of a BEII protein (108CF041, 110CF003) in percent based on data of starch of the wild type. The RVA analysis was carried out as described in Analytical method 2.

| | RVA Max (%) | RVA Min (%) | RVA Fin (%) | RVA Set (%) | RVA T (%) | Gel strength |
|---|---|---|---|---|---|---|
| cv. Desiree | 100 | 100 | 100 | 100 | 100 | 100 |
| 038VL008 | 167.1 | 40.4 | 52.6 | 77.6 | 54.2 | 63.0 |
| 108CF041 | 44.5 | 82.5 | 187.5 | 402.7 | 137.4 | 412.2 |
| 038VL107 | 152.0 | 76.1 | 81.9 | 93.8 | 76.9 | 51.7 |
| 110CF003 | 92.4 | 172.2 | n.d. | n.d. | 139.0 | 795.0 |

RVA Analytical Method 3

TABLE 4

Parameters of the RVA analysis of starch isolated from wild-type plants (cv. Desiree), plants with a reduced activity of an SSIII and a BEI protein (038VL008, 038VL107), and of plants with a reduced activity of an SSIII and of a BEI and of a BEII protein (108CF041, 110CF003) in percent based on data of starch of the wild type. The RVA analysis was carried out as described in Analytical method 3.

| | RVA Max (%) | RVA Min (%) | RVA Fin (%) | RVA Set (%) | RVA T (%) | Gel strength |
|---|---|---|---|---|---|---|
| cv. Desiree | 100 | 100 | 100 | 100 | 100 | 100 |
| 038VL008 | n.d. | 50.2 | 76.5 | 127.8 | 77.0 | 100.5 |
| 108CF041 | 74.7 | 291.0 | n.d. | 205.7 | 236.0 | 630.3 |
| 038VL107 | n.d. | 84.5 | 86.4 | 90.1 | 102.3 | 58.1 |
| 110CF003 | 89.8 | 259.7 | n.d. | n.d. | 196.6 | 663.9 |

Figure 1:
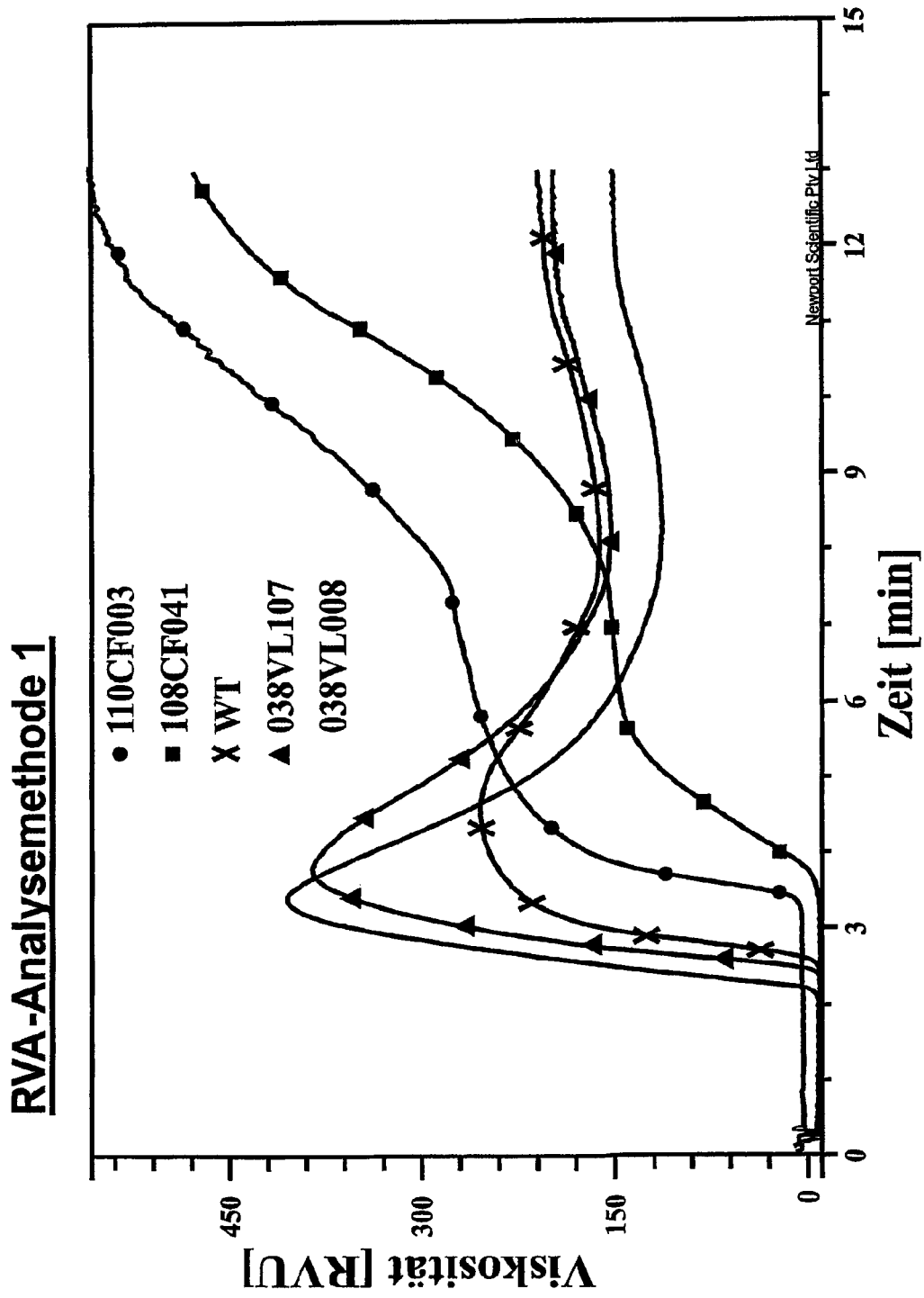
FIG. 1:
A graphic representation of the viscosity characteristics of starch from potato plants. The analysis was carried out using a Rapid Visco Analyser (Newport Scientific Pty Ltd., Investmet Support Group, Warriewod NSW 2102, Australia). The conditions under which the analysis was carried out are described under RVA analytical method 1 in the chapter "General Methods". The test starch was isolated from tubers of wild-type plants (WT), plants with a reduced activity of an SSIII protein and of a BEI protein (038VL008 and 038VL107) or from plants with a reduced activity of an SSIII protein and a BEI protein and a BEII protein (110CF003 and 108CF041). The starch was isolated by the method described under "Examples", "Starch extraction process for potatoes".

The following tables 5, 6 and 7 summarize the results of the RVA analysis. The data do not refer to the wild type, but are the actual measurements:

RVA Analytical Method 1 (See Also FIG. 1)

TABLE 5

Parameters of the RVA analysis of starch isolated from wild-type plants (cv. Desiree), plants with a reduced activity of an SSIII and a BEI protein (038VL008, 038VL107), and of plants with a reduced activity of an SSIII and of a BEI and of a BEII protein (108CF041, 110CF003) in RVUs. The RVA analysis was carried out as described in Analytical method 1.

| | RVA Max (RVU) | RVA Min (RVU) | RVA Fin (RVU) | RVA Set (RVU) | RVA T (RVU) | Gel strength |
|---|---|---|---|---|---|---|
| cv. Desiree | 255.05 | 162.33 | 210.25 | 47.92 | 4.6 | 25.1 |
| 038VL008 | 404.83 | 113.25 | 151.33 | 38.08 | 3.36 | 13.9 |
| 108CF041 | 152.08 | 145.92 | 478.33 | 332.42 | 6.91 | 133.6 |
| 038VL107 | 385.5 | 153 | 197.58 | 44.58 | 3.78 | 13.1 |
| 110CF003 | 271.5 | 257.42 | 557.25 | 299.83 | 6.97 | 185 |

Figure 2:
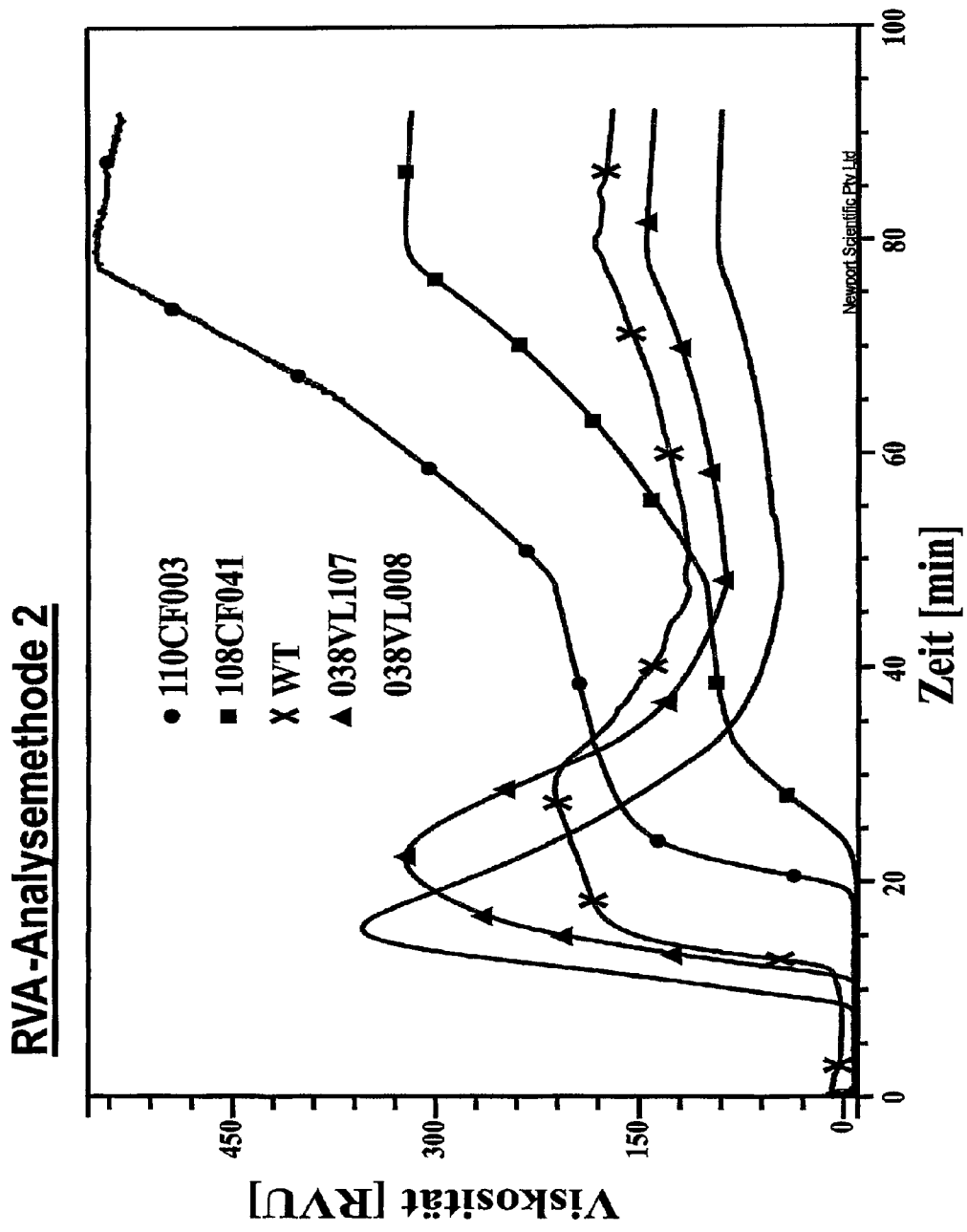
FIG. 2:
A graphic representation of the viscosity characteristics of starch from potato plants. The analysis was carried out using a Rapid Visco Analyser (Newport Scientific Pty Ltd., Investmet Support Group, Warriewod NSW 2102, Australia). The conditions under which the analysis was carried out are described under RVA analytical method 2 in the chapter "General Methods". The test starch was isolated from tubers of wild-type plants (WT), plants with a reduced activity of an SSIII protein and of a BEI protein (038VL008 and 038VL107) or from plants with a reduced activity of an SSIII protein and a BEI protein and a BEII protein (110CF003 and 108CF041). The starch was isolated by the method described under "Examples", "Starch extraction process for potatoes".

RVA Analytical Method 2 (See Also FIG. 2)

TABLE 6

Parameters of the RVA analysis of starch isolated from wild-type plants (cv. Desiree), plants with a reduced activity of an SSIII and a BEI protein (038VL008, 038VL107), and of plants with a reduced activity of an SSIII and of a BEI and of a BEII protein (108CF041, 110CF003) in RVUs. The RVA analysis was carried out as described in Analytical method 2.

| | RVA Max (RVU) | RVA Min (RVU) | RVA Fin (RVU) | RVA Set (RVU) | RVA T (RVU) | Gel strength |
|---|---|---|---|---|---|---|
| cv. Desiree | 212.17 | 113.75 | 169.25 | 55.5 | 28.78 | 23.8 |
| 038VL008 | 354.58 | 45.92 | 89 | 43.08 | 15.61 | 15 |
| 108CF041 | 94.33 | 93.83 | 317.33 | 223.5 | 39.53 | 98.1 |
| 038VL107 | 322.58 | 86.58 | 138.67 | 52.08 | 22.13 | 12.3 |
| 110CF003 | 196.08 | 195.92 | n.d. | n.d. | 39.99 | 189.2 |

Figure 3:
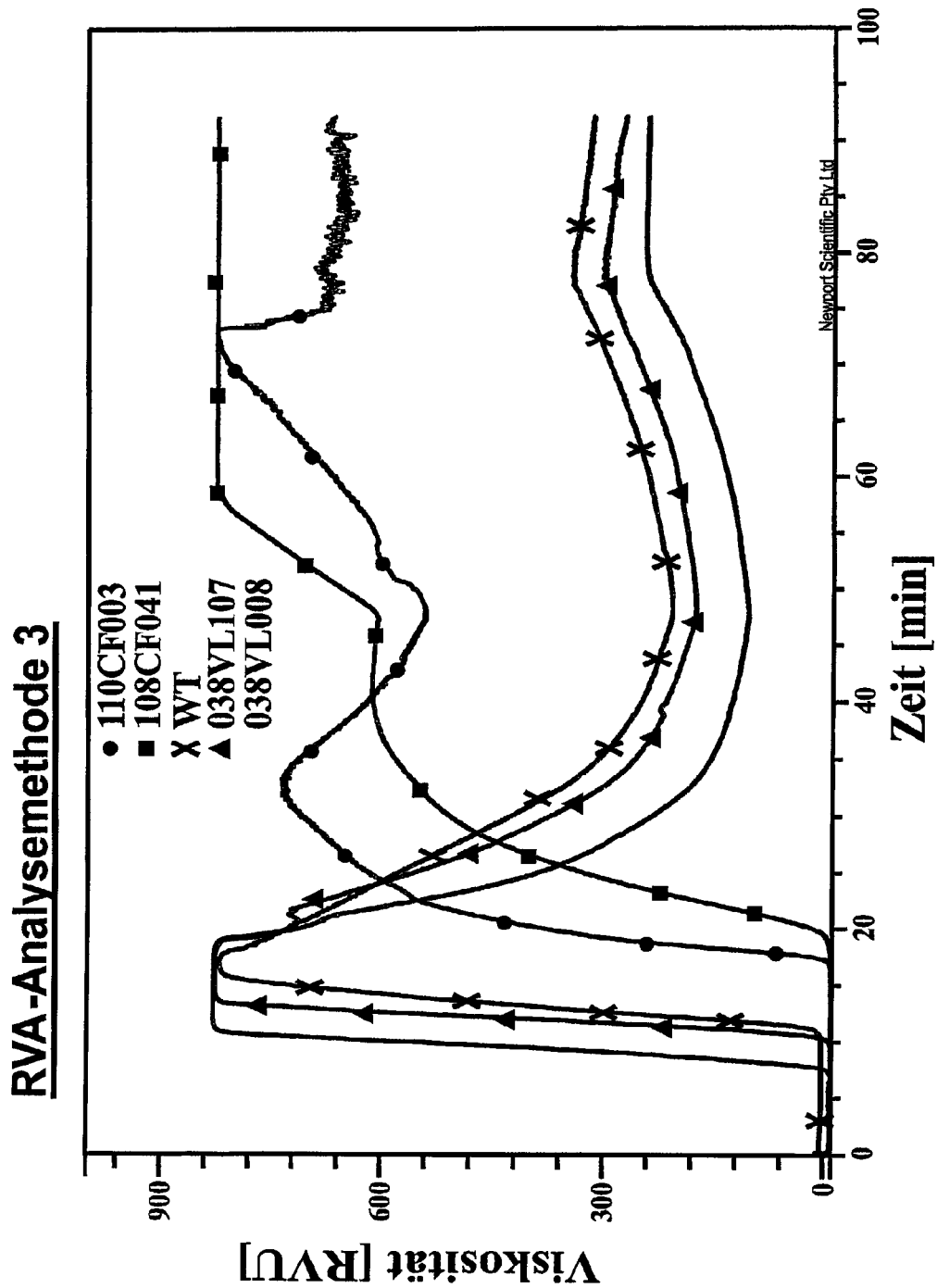
FIG. 3:
A graphic representation of the viscosity characteristics of starch from potato plants. The analysis was carried out using a Rapid Visco Analyser (Newport Scientific Pty Ltd., Investmet Support Group, Warriewod NSW 2102, Australia). The conditions under which the analysis was carried out are described under RVA analytical method 3 in the chapter "General Methods". The test starch was isolated from tubers of wild-type plants (WT), plants with a reduced activity of an SSIII protein and of a BEI protein (038VL008 and 038VL107) or from plants with a reduced activity of an SSIII protein and a BEI protein and a BEII protein (110CF003 and 108CF041). The starch was isolated by the method described under "Examples", "Starch extraction process for potatoes".
Figure 4:
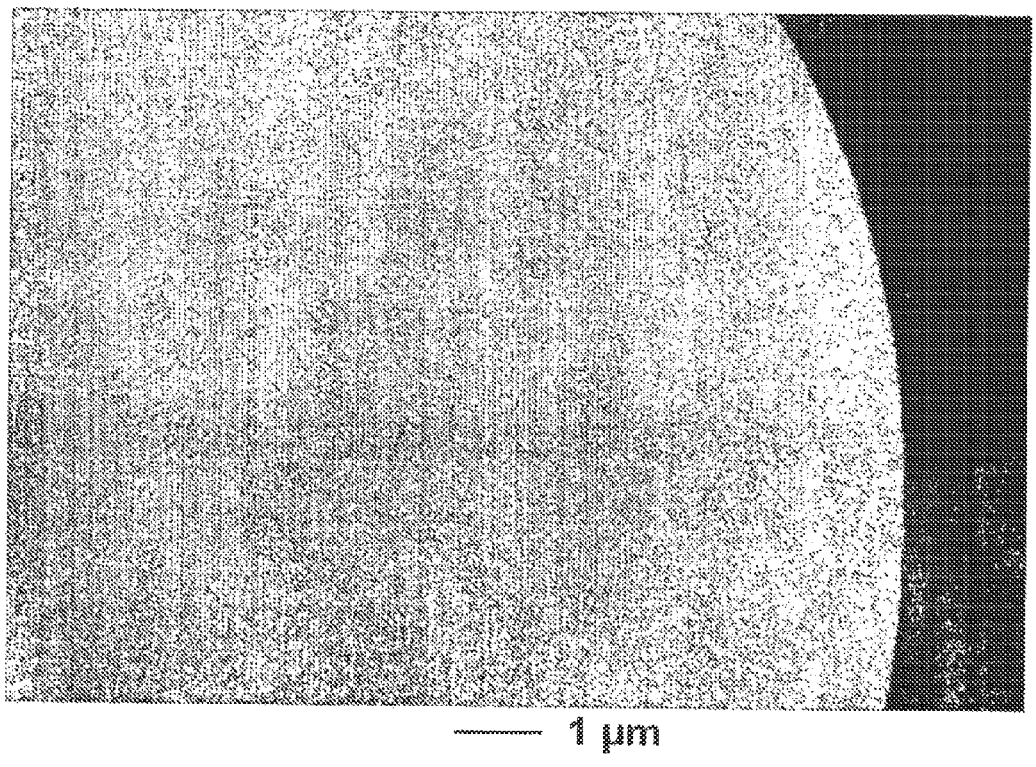
FIG. 4:
Scanning-electron micrograph of a potato starch granule isolated from wild-type plants.
Figure 5:
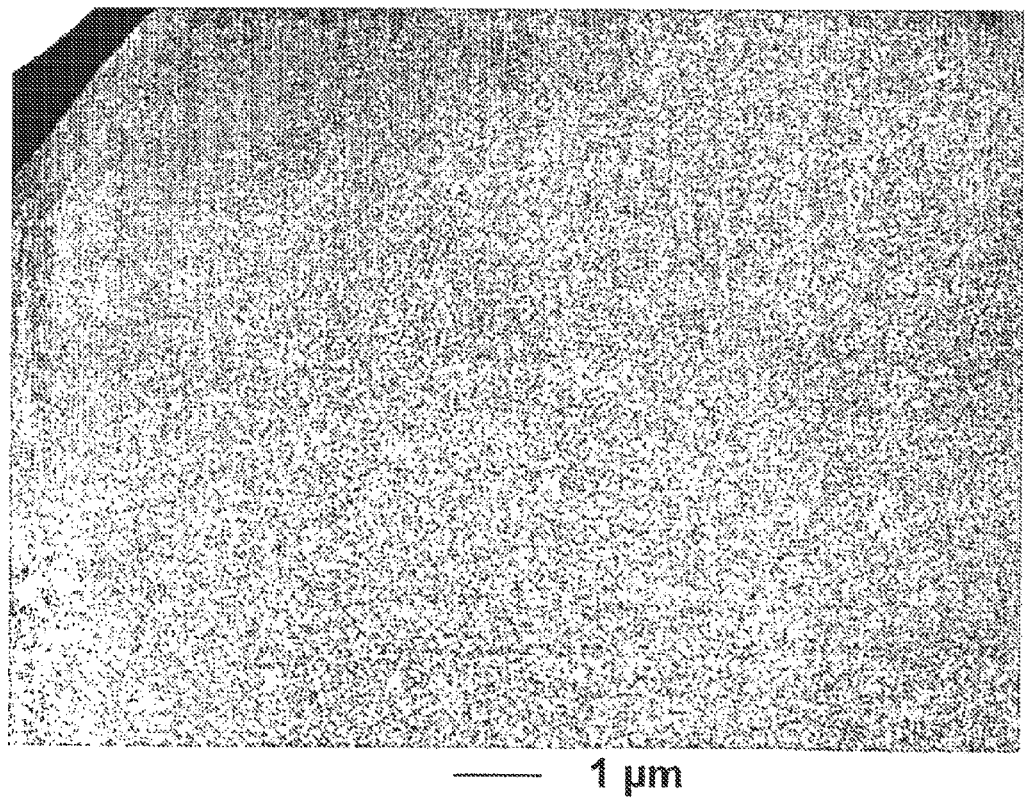
FIG. 5:
Scanning-electron micrograph of a potato starch granule isolated from plants with a reduced activity of an SSIII protein and of a BEI protein and of a BEII protein (110CF003).

RVA Analytical Method 3 (See Also FIG. 3)

TABLE 7

Parameters of the RVA analysis of starch isolated from wild-type plants (cv. Desiree), plants with a reduced activity of an SSIII and a BEI protein (038VL008, 038VL107), and of plants with a reduced activity of an SSIII and of a BEI and of a BEII protein (108CF041, 110CF003) in RVUs. The RVA analysis was carried out as described in Analytical method 3.

| | RVA Max (RVU) | RVA Min (RVU) | RVA Fin (RVU) | RVA Set (RVU) | RVA T (RVU) | Gel strength |
|---|---|---|---|---|---|---|
| Desiree | 819.67 | 207.67 | 314.25 | 106.58 | 16.88 | 56.5 |
| 038VL008 | n.d. | 104.17 | 240.33 | 136.17 | 12.99 | 56.8 |
| 108CF041 | 612.33 | 604.25 | 823.5 | 219.25 | 39.83 | 356.1 |
| 038VL107 | n.d. | 175.42 | 271.5 | 96.08 | 17.27 | 32.8 |
| 110CF003 | 736.08 | 539.42 | n.d. | n.d. | 33.18 | 375.1 |

Summary of the Phosphate and Amylose Analyses:

TABLE 8

Phosphate and amylose contents of starch isolated from wild-type plants (cv. Desiree), plants with a reduced activity of an SSIII and a BEI protein (038VL008, 038VL107) and of plants with a reduced activity of an SSIII and of a BEI and of a BEII protein (108CF041, 110CF003). The phosphate contents in the C6 position of the glucose monomers and the total phosphate content of the starch are indicated in percent based on starch from wild-type plants; amylose contents are indicated in percent amylose based on the total amount of the starch, or in percent based on the amylose content of starch from wild-type plants.

| No. | Genotype | Phosphate in C6 (%) | Total phosphate in (%) | Amylose (%) | Amylose (% WT) |
|---|---|---|---|---|---|
| 1 | cv. Desiree | 100 | 100 | 22 | 100 |
| 2 | 038VL008 | 346.4 | 255.2 | 19.4 | 85.8 |
| 3 | 108CF041 | 557.3 | 427.6 | 36.8 | 162.8 |
| 4 | 038VL107 | 225.5 | 182.8 | 19.7 | 87.2 |
| 5 | 110CF003 | 446.4 | 348.3 | 34.6 | 153.1 |

The analysis of the side-chain distribution of the amylopectin was carried out as described above. The table which follows is a summary of the contributions of the individual peak areas:

TABLE 9

The table shows a summary of the contributions of the individual peak areas of the HPAEC chromatogram to the total peak area of wild-type plants (cv. Desiree), of 038VL008 and 038Vl107 plants (potato plants with reduced activity of a BEI protein and of an SSII protein) and of selected lines of the transformations 108CF and 110CF (potato plants with a reduced activity of an SSII protein and of a BEI protein and of a BEII protein). The number of glucose monomers in the individual side chains is shown as dp.

| Glucose units | cv. Desiree | 038VL008 | 108CF041 | 038VL107 | 110CF003 |
|---|---|---|---|---|---|
| dp 6 | 1.52 | 4.16 | 1.88 | 2.39 | 0.86 |
| dp 7 | 1.4 | 1.4 | 0.63 | 1.42 | 0.59 |
| dp 8 | 1.23 | 0.77 | 0.33 | 0.99 | 0.38 |
| dp 9 | 2.05 | 1.42 | 0.74 | 1.79 | 0.75 |
| dp 10 | 3.55 | 2.8 | 1.74 | 3.33 | 1.77 |
| dp 11 | 5.16 | 4.41 | 2.92 | 4.96 | 3.46 |
| dp 12 | 6.25 | 5.77 | 4.47 | 6.22 | 5.17 |
| dp 13 | 6.71 | 6.7 | 5.63 | 6.87 | 6.35 |
| dp 14 | 6.75 | 7.06 | 6.35 | 6.99 | 7.38 |
| dp 15 | 6.48 | 6.76 | 6.62 | 6.65 | 7.63 |
| dp 16 | 6.07 | 5.99 | 6.34 | 6.11 | 7.13 |
| dp 17 | 5.6 | 5.21 | 5.81 | 5.49 | 6.3 |
| dp 18 | 5.28 | 4.78 | 5.87 | 5.11 | 5.98 |
| dp 19 | 4.99 | 4.74 | 6.17 | 4.94 | 5.91 |
| dp 20 | 4.76 | 4.65 | 6.07 | 4.78 | 5.64 |
| dp 21 | 4.5 | 4.46 | 5.65 | 4.5 | 5.26 |
| dp 22 | 4.16 | 4.12 | 5.07 | 4.2 | 4.7 |
| dp 23 | 3.77 | 3.68 | 4.59 | 3.78 | 4.19 |
| dp 24 | 3.44 | 3.36 | 4.24 | 3.42 | 3.75 |
| dp 25 | 3.08 | 3.09 | 3.86 | 3.07 | 3.49 |
| dp 26 | 2.73 | 2.8 | 3.36 | 2.77 | 3.03 |
| dp 27 | 2.39 | 2.58 | 2.95 | 2.37 | 2.65 |
| dp 28 | 2.07 | 2.26 | 2.39 | 2.01 | 2.1 |
| dp 29 | 1.67 | 1.87 | 1.87 | 1.71 | 1.69 |
| dp 30 | 1.38 | 1.58 | 1.54 | 1.35 | 1.3 |
| dp 31 | 1.07 | 1.28 | 1.02 | 1.04 | 0.87 |
| dp 32 | 0.79 | 0.96 | 0.7 | 0.75 | 0.6 |
| dp 33 | 0.57 | 0.69 | 0.6 | 0.51 | 0.51 |
| dp 34 | 0.36 | 0.43 | 0.39 | 0.32 | 0.34 |
| dp 35 | 0.22 | 0.22 | 0.19 | 0.17 | 0.2 |
| Total | 100 | 100 | 99.99 | 100.01 | 99.98 |

The peak chain length, whose value is the mean of the two chain lengths (given in DP) which contribute most to the total area under the peaks of the HPAEC chromatogram, is—in the case of debranched amylopectin—of wild-type plants at DP=13, in the case of 038VL plants likewise at DP=13 and in the case of the 108CF and 110CF plants, on average, at 15.

If the peak chain length of the transgenic plants is compared with the peak chain length of amylopectin of wild-type plants, the following values result for the peak chain length ratio (PCL ratio):

PCL ratio for 038VL=13/13=1

PCL ratio for 108/110CF=15/13=1.15

In addition, the starch granule morphology was analysed using a scanning electron microscope (SEM).

The surface of the starch granules of 108/110CF plants appears coated or raised with pore formation.

Moreover, the granule size determination was carried out using a "Lumosed"-type photosedimentometer from Retsch GmbH, Germany.

The mean granule size of untreated starch samples was determined (Table 3).

TABLE 10

Mean granule size values of starch isolated from wild-type plants (cv. Desiree), plants with a reduced activity of an SSIII and of a BEI protein (038VL008, 038VL107), and of plants with a reduced activity of an SSIII and of a BEI and of a BEII protein (108CF041, 110CF003).
Mean granule size [μm]

| Sample | Mean granule size |
|---|---|
| cv. Desiree | 29.7 |
| 038VL008 | 21.5 |
| 108CF041 | 20.8 |
| 038VL107 | 22.9 |
| 110CF003 | 20.7 |

Example 3

Analysis of the Amylopectin Side Chain Distribution by Means of Gel Permeation Chromatography To separate amylose and amylopectin, 100 mg of starch are dissolved in 6 ml of 90% strength (v/v) DMSO with constant stirring. After addition of 3 volumes of ethanol, the precipitate is separated off by centrifugation for 10 minutes at 1 800 g at room temperature. The pellet is subsequently washed with 30 ml of ethanol, dried and dissolved in 10 ml of 1% strength (w/v) NaCl solution at 60° C. After cooling the solution to 30° C., approximately 50 mg of thymol are added slowly, and this solution is incubated for 2 to 3 days at 30° C. The solution is subsequently centrifuged for 30 minutes at 2 000 g at room temperature. The supernatant is treated with three volumes of ethanol, and the amylopectin which precipitates is separated off by centrifugation for 5 minutes at 2 000 g at room temperature. The pellet (amylopectin) is washed with 10 ml of 70% strength (v/v) ethanol, centrifuged for 10 minutes at 2 000 g at room temperature and then dried using acetone.

10 mg of amylopectin are subsequently stirred for 10 minutes at 70° C. in 250 μl of 90% strength (v/v) DMSO. 375 μl of water at a temperature of 80° C. are added to the solution until dissolution is complete.

200 μl of this solution are treated with 300 μl of a 16.6 mM sodium acetate solution pH 3.5 and 2 μl of isoamylase (0.24 μ/μl, Megazyme, Sydney, Australia) and the mixture is incubated for 15 hours at 37° C.

A 1:4 dilution of this aqueous isoamylase reaction mixture with DMSO, comprising 90 mM sodium nitrate, is subsequently filtered through a 0.2 μm filter, and 24 μl of the filtrate is analysed chromatographically. Separation was carried out with two columns connected in series, first a Gram PSS3000 (Polymer Standards Service, with suitable precolumn), followed by a Gram PSS100. Detection was by means of refraction index detector (RI 71, Shodex). The column was equilibrated with DMSO comprising 90 mM sodium nitrate. It was eluted with DMSO comprising 90 mM sodium nitrate at a flow rate of 0.7 ml/min over a period of 1 hour.

To correlate the elution volume with the molecular mass, the column used was calibrated with dextran standards. The dextrans used, their molecular mass and the elution volumes are shown in FIG. 9. Using the resulting calibration graph, the elution diagram was shown as a molecular weight distribution (FIG. 10).

The chromatograms obtained were further evaluated using the program Wingpc Version 6 from Polymer Standards Service GmbH, Mainz, Germany.

The total area under the line of the GPC chromatogram was divided into individual segments, each of which represent groups of side chains of different lengths. The chosen segments contained glucan chains with the following degree of polymerization (DP=number of glucose monomers within one side chain): DP<11, DP12-18, DP19-24, DP25-30, DP31-36, DP37-42, DP43-48, DP49-55, DP56-61 and DP62-123. To determine the molecular weight of the individual side chains, a molecular weight of 162 was assumed for glucose. The total area under the line in the GPC chromatogram was then set as 100%, and the percentage of the areas of the individual segments was calculated based on the percentage of the total area. Results obtained from this analysis are shown in Table 11.

TABLE 11

Side chain profiles DP 12 to 18, DP 19 to 24, DP 25 to 30, DP 31 to 36, DP 37 to 42, DP 43-48, DP 49 to 55, DP 56 to 61 and DP 62 to 123 for amylopectin isolated from wild-type plants (cv. Desiree) and from plants with a reduced activity of an SSIII and of a BEI and of a BEII protein (108CF041). The percentages indicate the modification of the individual side chain profiles based on amylopectin isolated from wild-type plants.

| | Wild type | 08CF041c |
|---|---|---|
| DP ≧ 11 | 100% | 40% |
| DP12-18 | 100% | 50% |
| DP19-24 | 100% | 69% |
| DP25-30 | 100% | 91% |
| DP31-36 | 100% | 111% |
| DP37-42 | 100% | 116% |
| DP43-48 | 100% | 110% |
| DP49-55 | 100% | 107% |
| DP56-61 | 100% | 109% |
| DP62-123 | 100% | 157% |

The invention claimed is:

1. A method for producing a starch comprising extracting starch from a genetically modified dicotyledonous plant cell, wherein said genetically modified plant cell comprises
   (1) a first foreign nucleic acid molecule, wherein said first foreign nucleic acid molecule is
      (a) a DNA molecule encoding at least one antisense RNA that reduces the expression of at least one endogenous gene encoding a SSIII protein, said DNA molecule comprising at least 95% identity with SEQ ID NO: 1;
      (b) a DNA molecule which, via a co-suppression effect, reduces the expression of at least one endogenous gene encoding a SSIII protein, said DNA molecule comprising at least 95% identity with SEQ ID NO: 1; or
      (c) a DNA molecule that simultaneously encodes at least one antisense RNA and at least one sense RNA, where said antisense RNA and said sense RNA form a double-stranded RNA molecule that reduces the expression of at least one endogenous gene encoding a SSIII protein, said DNA molecule comprising at least 95% identity with SEQ ID NO: 1;
   (2) a second foreign nucleic acid molecule, wherein said second foreign nucleic acid molecule is
      (a) a DNA molecule encoding at least one antisense RNA that reduces the expression of at least one endogenous gene encoding a BEI protein, said DNA molecule comprising at least 95% identity with SEQ ID NO: 4;
      (b) a DNA molecule which, via a co-suppression effect, reduces the expression of at least one endogenous gene encoding a BEI protein, said DNA molecule comprising at least 95% identity with SEQ ID NO: 4; or
      (c) a DNA molecule that simultaneously encodes at least one antisense RNA and at least one sense RNA, where said antisense RNA and said sense RNA form a double-stranded RNA molecule that reduces the expression of at least one endogenous gene encoding a BEI protein, said DNA molecule comprising at least 95% identity with SEQ ID NO: 4; and
   (3) a third foreign nucleic acid molecule, wherein said third foreign nucleic acid molecule is
      (a) a DNA molecule encoding at least one antisense RNA that reduces the expression of at least one endogenous gene encoding a BEII protein, said DNA molecule comprising at least 95% identity with SEQ ID NO: 6;
      (b) a DNA molecule which, via a co-suppression effect, reduces the expression of at least one endogenous gene encoding a BEII protein, said DNA molecule comprising at least 95% identity with SEQ ID NO: 6; or
      (c) a DNA molecule that simultaneously encodes at least one antisense RNA and at least one sense RNA, where said antisense RNA and said sense RNA form a double-stranded RNA molecule that reduces the expression of at least one endogenous gene encoding a BEII protein, said DNA molecule comprising at least 95% identity with SEQ ID NO: 6 and
   further wherein said genetically modified plant cell synthesizes a modified starch, which after gelatinization of a 6% suspension in water forms a gel with a gel strength that is increased by at least 300% in comparison with the gel strength of starch extracted from corresponding plant cells, of wild-type plants, which have not been genetically modified.

2. A method for producing a starch, comprising extracting starch from a genetically modified plant comprising a genetically modified dicotyledonous plant cell, wherein said genetically modified plant cell comprises
   (1) a first foreign nucleic acid molecule, wherein said first foreign nucleic acid molecule is
      (a) a DNA molecule encoding at least one antisense RNA that reduces the expression of at least one endogenous gene encoding a SSIII protein, said DNA molecule comprising at least 95% identity with SEQ ID NO: 1;
      (b) a DNA molecule which, via a co-suppression effect, reduces the expression of at least one endogenous gene encoding a SSIII protein, said DNA molecule comprising at least 95% identity with SEQ ID NO: 1; or
      (c) a DNA molecule that simultaneously encodes at least one antisense RNA and at least one sense RNA, where said antisense RNA and said sense RNA form a double-stranded RNA molecule that reduces the expression of at least one endogenous gene encoding a SSIII protein, said DNA molecule comprising at least 95% identity with SEQ ID NO: 1;

(2) a second foreign nucleic acid molecule, wherein said second foreign nucleic acid molecule is
  (a) a DNA molecule encoding at least one antisense RNA that reduces the expression of at least one endogenous gene encoding a BEI protein, said DNA molecule comprising at least 95% identity with SEQ ID NO: 4;
  (b) a DNA molecule which, via a co-suppression effect, reduces the expression of at least one endogenous gene encoding a BEI protein, said DNA molecule comprising at least 95% identity with SEQ ID NO: 4; or
  (c) a DNA molecule that simultaneously encodes at least one antisense RNA and at least one sense RNA, where said antisense RNA and said sense RNA form a double-stranded RNA molecule that reduces the expression of at least one endogenous gene encoding a BEI protein, said DNA molecule comprising at least 95% identity with SEQ ID NO: 4; and
(3) a third foreign nucleic acid molecule, wherein said third foreign nucleic acid molecule is
  (a) a DNA molecule encoding at least one antisense RNA that reduces the expression of at least one endogenous gene encoding a BEII protein, said DNA molecule comprising at least 95% identity with SEQ ID NO: 6;
  (b) a DNA molecule which, via a co-suppression effect, reduces the expression of at least one endogenous gene encoding a BEII protein, said DNA molecule comprising at least 95% identity with SEQ ID NO: 6; or
  (c) a DNA molecule that simultaneously encodes at least one antisense RNA and at least one sense RNA, where said antisense RNA and said sense RNA form a double-stranded RNA molecule that reduces the expression of at least one endogenous gene encoding a BEII protein, said DNA molecule comprising at least 95% identity with SEQ ID NO: 6, and further wherein said genetically modified plant cell synthesizes a modified starch, which after gelatinization of a 6% suspension in water forms a gel with a gel strength that is increased by at least 300% in comparison with the gel strength of starch extracted from corresponding plant cells, of wild-type plants, which have not been genetically modified.

3. The method of claim 1, wherein said plant cell is a potato plant cell.

4. The method of claim 1, wherein
said first foreign nucleic acid molecule is a DNA molecule encoding at least one antisense RNA that reduces the expression of at least one endogenous gene encoding a SSIII protein, said DNA molecule comprising at least 95% identity with SEQ ID NO: 1;
said second foreign nucleic acid molecule is a DNA molecule encoding at least one antisense RNA that reduces the expression of at least one endogenous gene encoding a BEI protein, said DNA molecule comprising at least 95% identity with SEQ ID NO: 4; and
said third foreign nucleic acid molecule is a DNA molecule encoding at least one antisense RNA that reduces the expression of at least one endogenous gene encoding a BEII protein, said DNA molecule comprising at least 95% identity with SEQ ID NO: 6.

5. The method of claim 1, wherein
(1) said first foreign nucleic acid molecule is
  (a) a DNA molecule encoding at least one antisense RNA that reduces the expression of at least one endogenous gene encoding a SSIII protein, said DNA molecule comprising SEQ ID NO: 1;
  (b) a DNA molecule which, via a co-suppression effect, reduces the expression of at least one endogenous gene encoding a SSIII protein, said DNA molecule comprising SEQ ID NO: 1; or
  (c) a DNA molecule that simultaneously encodes at least one antisense RNA and at least one sense RNA, where said antisense RNA and said sense RNA form a double-stranded RNA molecule that reduces the expression of at least one endogenous gene encoding a SSIII protein, said DNA molecule comprising SEQ ID NO: 1;
(2) a second foreign nucleic acid molecule, wherein said second foreign nucleic acid molecule is
  (a) a DNA molecule encoding at least one antisense RNA that reduces the expression of at least one endogenous gene encoding a BEI protein, said DNA molecule comprising SEQ ID NO: 4;
  (b) a DNA molecule which, via a co-suppression effect, reduces the expression of at least one endogenous gene encoding a BEI protein, said DNA molecule comprising SEQ ID NO: 4; or
  (c) a DNA molecule that simultaneously encodes at least one antisense RNA and at least one sense RNA, where said antisense RNA and said sense RNA form a double-stranded RNA molecule that reduces the expression of at least one endogenous gene encoding a BEI protein, said DNA molecule comprising SEQ ID NO: 4; and
(3) a third foreign nucleic acid molecule, wherein said third foreign nucleic acid molecule is
  (a) a DNA molecule encoding at least one antisense RNA that reduces the expression of at least one endogenous gene encoding a BEII protein, said DNA molecule comprising SEQ ID NO: 6;
  (b) a DNA molecule which, via a co-suppression effect, reduces the expression of at least one endogenous gene encoding a BEII protein, said DNA molecule comprising SEQ ID NO: 6; or
  (c) a DNA molecule that simultaneously encodes at least one antisense RNA and at least one sense RNA, where said antisense RNA and said sense RNA form a double-stranded RNA molecule that reduces the expression of at least one endogenous gene encoding a BEII protein, said DNA molecule comprising SEQ ID NO: 6.

6. The method of claim 5, wherein
said first foreign nucleic acid molecule is a DNA molecule encoding at least one antisense RNA that reduces the expression of at least one endogenous gene encoding a SSIII protein, said DNA molecule comprising SEQ ID NO: 1;
said second foreign nucleic acid molecule is a DNA molecule encoding at least one antisense RNA that reduces the expression of at least one endogenous gene encoding a BEI protein, said DNA molecule comprising SEQ ID NO: 4; and
said third foreign nucleic acid molecule is a DNA molecule encoding at least one antisense RNA that reduces the expression of at least one endogenous gene encoding a BEII protein, said DNA molecule comprising SEQ ID NO: 6.

7. The method of claim 2, wherein said plant cell is a potato plant cell.

8. The method of claim 2, wherein
said first foreign nucleic acid molecule is a DNA molecule encoding at least one antisense RNA that reduces the expression of at least one endogenous gene encoding a SSIII protein, said DNA molecule comprising at least 95% identity with SEQ ID NO: 1;
said second foreign nucleic acid molecule is a DNA molecule encoding at least one antisense RNA that reduces the expression of at least one endogenous gene encoding a BEI protein, said DNA molecule comprising at least 95% identity with SEQ ID NO: 4; and
said third foreign nucleic acid molecule is a DNA molecule encoding at least one antisense RNA that reduces the expression of at least one endogenous gene encoding a BEII protein, said DNA molecule comprising at least 95% identity with SEQ ID NO: 6.

9. The method of claim 2, wherein
(1) said first foreign nucleic acid molecule is
   (a) a DNA molecule encoding at least one antisense RNA that reduces the expression of at least one endogenous gene encoding a SSIII protein, said DNA molecule comprising SEQ ID NO: 1;
   (b) a DNA molecule which, via a co-suppression effect, reduces the expression of at least one endogenous gene encoding a SSIII protein, said DNA molecule comprising SEQ ID NO: 1; or
   (c) a DNA molecule that simultaneously encodes at least one antisense RNA and at least one sense RNA, where said antisense RNA and said sense RNA form a double-stranded RNA molecule that reduces the expression of at least one endogenous gene encoding a SSIII protein, said DNA molecule comprising SEQ ID NO: 1;
(2) a second foreign nucleic acid molecule, wherein said second foreign nucleic acid molecule is
   (a) a DNA molecule encoding at least one antisense RNA that reduces the expression of at least one endogenous gene encoding a BEI protein, said DNA molecule comprising SEQ ID NO: 4;
   (b) a DNA molecule which, via a co-suppression effect, reduces the expression of at least one endogenous gene encoding a BEI protein, said DNA molecule comprising SEQ ID NO: 4; or
   (c) a DNA molecule that simultaneously encodes at least one antisense RNA and at least one sense RNA, where said antisense RNA and said sense RNA form a double-stranded RNA molecule that reduces the expression of at least one endogenous gene encoding a BEI protein, said DNA molecule comprising SEQ ID NO: 4; and
(3) a third foreign nucleic acid molecule, wherein said third foreign nucleic acid molecule is
   (a) a DNA molecule encoding at least one antisense RNA that reduces the expression of at least one endogenous gene encoding a BEII protein, said DNA molecule comprising SEQ ID NO: 6;
   (b) a DNA molecule which, via a co-suppression effect, reduces the expression of at least one endogenous gene encoding a BEII protein, said DNA molecule comprising SEQ ID NO: 6; or
   (c) a DNA molecule that simultaneously encodes at least one antisense RNA and at least one sense RNA, where said antisense RNA and said sense RNA form a double-stranded RNA molecule that reduces the expression of at least one endogenous gene encoding a BEII protein, said DNA molecule comprising SEQ ID NO: 6.

10. The method of claim 9, wherein
said first foreign nucleic acid molecule is a DNA molecule encoding at least one antisense RNA that reduces the expression of at least one endogenous gene encoding a SSIII protein, said DNA molecule comprising SEQ ID NO: 1;
said second foreign nucleic acid molecule is a DNA molecule encoding at least one antisense RNA that reduces the expression of at least one endogenous gene encoding a BEI protein, said DNA molecule comprising SEQ ID NO: 4; and
said third foreign nucleic acid molecule is a DNA molecule encoding at least one antisense RNA that reduces the expression of at least one endogenous gene encoding a BEII protein, said DNA molecule comprising SEQ ID NO: 6.

11. A method for producing a starch comprising extracting starch from a genetically modified dicotyledonous plant cell, wherein said genetically modified plant cell comprises
(1) a first foreign nucleic acid molecule, wherein said first foreign nucleic acid molecule is
   (a) a DNA molecule encoding at least one antisense RNA that reduces the expression of at least one endogenous gene encoding a SSIII protein, said DNA molecule comprising at least 100 nucleotides of SEQ ID NO: 1;
   (b) a DNA molecule which, via a co-suppression effect, reduces the expression of at least one endogenous gene encoding a SSIII protein, said DNA molecule comprising at least 100 nucleotides of SEQ ID NO: 1; or
   (c) a DNA molecule that simultaneously encodes at least one antisense RNA and at least one sense RNA, where said antisense RNA and said sense RNA form a double-stranded RNA molecule that reduces the expression of at least one endogenous gene encoding a SSIII protein, said DNA molecule comprising at least 100 nucleotides of SEQ ID NO: 1;
(2) a second foreign nucleic acid molecule, wherein said second foreign nucleic acid molecule is
   (a) a DNA molecule encoding at least one antisense RNA that reduces the expression of at least one endogenous gene encoding a BEI protein, said DNA molecule comprising at least 100 nucleotides of SEQ ID NO: 4;
   (b) a DNA molecule which, via a co-suppression effect, reduces the expression of at least one endogenous gene encoding a BEI protein, said DNA molecule comprising at least 100 nucleotides of SEQ ID NO: 4; or
   (c) a DNA molecule that simultaneously encodes at least one antisense RNA and at least one sense RNA, where said antisense RNA and said sense RNA form a double-stranded RNA molecule that reduces the expression of at least one endogenous gene encoding a BEI protein, said DNA molecule comprising at least 100 nucleotides of SEQ ID NO: 4; and
(3) a third foreign nucleic acid molecule, wherein said third foreign nucleic acid molecule is
   (a) a DNA molecule encoding at least one antisense RNA that reduces the expression of at least one endogenous gene encoding a BEII protein, said DNA molecule comprising at least 100 nucleotides of SEQ ID NO: 6;
   (b) a DNA molecule which, via a co-suppression effect, reduces the expression of at least one endogenous gene encoding a BEII protein, said DNA molecule comprising at least 100 nucleotides of SEQ ID NO: 6; or (c) a DNA molecule that simultaneously encodes at least one antisense RNA and at least one sense RNA, where said antisense RNA and said sense RNA form a double-stranded RNA molecule that reduces the expression of at least one endogenous gene encoding a BEII protein, said DNA molecule comprising at least 100 nucleotides of SEQ ID NO: 6, and further wherein said genetically modified plant cell synthesizes a modified starch, which after gelatinization of a 6% suspension in water forms a gel with a gel strength that is increased by at least 300% in comparison with the gel strength of starch extracted from corresponding plant cells, of wild-type plants, which have not been genetically modified.

12. The method of claim 11, wherein said first foreign nucleic acid molecule is a DNA molecule encoding at least one antisense RNA that reduces the expression of at least one endogenous gene encoding a SSIII protein, said DNA molecule comprising at least 100 nucleotides of SEQ ID NO: 1;

said second foreign nucleic acid molecule is a DNA molecule encoding at least one antisense RNA that reduces the expression of at least one endogenous gene encoding a BEI protein, said DNA molecule comprising at least 100 nucleotides of SEQ ID NO: 4; and said third foreign nucleic acid molecule is a DNA molecule encoding at least one antisense RNA that reduces the expression of at least one endogenous gene encoding a BEII protein, said DNA molecule comprising at least 100 nucleotides of SEQ ID NO: 6.

13. The method of claim 11, wherein (1) said first foreign nucleic acid molecule is
    (a) a DNA molecule encoding at least one antisense RNA that reduces the expression of at least one endogenous gene encoding a SSIII protein, said DNA molecule comprising at least 500 nucleotides of SEQ ID NO: 1;
    (b) a DNA molecule which, via a co-suppression effect, reduces the expression of at least one endogenous gene encoding a SSIII protein, said DNA molecule comprising at least 500 nucleotides of SEQ ID NO: 1; or
    (c) a DNA molecule that simultaneously encodes at least one antisense RNA and at least one sense RNA, where said antisense RNA and said sense RNA form a double-stranded RNA molecule that reduces the expression of at least one endogenous gene encoding a SSIII protein, said DNA molecule comprising at least 500 nucleotides of SEQ ID NO: 1.

(2) a second foreign nucleic acid molecule, wherein said second foreign nucleic acid molecule is
    (a) a DNA molecule encoding at least one antisense RNA that reduces the expression of at least one endogenous gene encoding a BEI protein, said DNA molecule comprising at least 500 nucleotides of SEQ ID NO: 4;
    (b) a DNA molecule which, via a co-suppression effect, reduces the expression of at least one endogenous gene encoding a BEI protein, said DNA molecule comprising at least 500 nucleotides of SEQ ID NO: 4; or
    (c) a DNA molecule that simultaneously encodes at least one antisense RNA and at least one sense RNA, where said antisense RNA and said sense RNA form a double-stranded RNA molecule that reduces the expression of at least one endogenous gene encoding a BEI protein, said DNA molecule comprising at least 500 nucleotides of SEQ ID NO: 4; and (3) a third foreign nucleic acid molecule, wherein said third foreign nucleic acid molecule is
    (a) a DNA molecule encoding at least one antisense RNA that reduces the expression of at least one endogenous gene encoding a BEII protein, said DNA molecule comprising at least 500 nucleotides of SEQ ID NO: 6;
    (b) a DNA molecule which, via a co-suppression effect, reduces the expression of at least one endogenous gene encoding a BEII protein, said DNA molecule comprising at least 500 nucleotides of SEQ ID NO: 6; or
    (c) a DNA molecule that simultaneously encodes at least one antisense RNA and at least one sense RNA, where said antisense RNA and said sense RNA form a double-stranded RNA molecule that reduces the expression of at least one endogenous gene encoding a BEII protein, said DNA molecule comprising at least 500 nucleotides of SEQ ID NO: 6.

14. The method of claim 13, wherein said first foreign nucleic acid molecule is a DNA molecule encoding at least one antisense RNA that reduces the expression of at least one endogenous gene encoding a SSIII protein, said DNA molecule comprising at least 500 nucleotides of SEQ ID NO: 1;

said second foreign nucleic acid molecule is a DNA molecule encoding at least one antisense RNA that reduces the expression of at least one endogenous gene encoding a BEI protein, said DNA molecule comprising at least 500 nucleotides of SEQ ID NO: 4; and said third foreign nucleic acid molecule is a DNA molecule encoding at least one antisense RNA that reduces the expression of at least one endogenous gene encoding a BEII protein, said DNA molecule comprising at least 500 nucleotides of SEQ ID NO: 6.

15. The method of claim 11, wherein said plant cell is a potato plant cell.

16. A method for producing a starch comprising extracting starch from a genetically modified plant comprising a genetically modified dicotyledonous plant cell, wherein said genetically modified plant cell comprises (1) a first foreign nucleic acid molecule, wherein said first foreign nucleic acid molecule is
    (a) a DNA molecule encoding at least one antisense RNA that reduces the expression of at least one endogenous gene encoding a SSIII protein, said DNA molecule comprising at least 100 nucleotides of SEQ ID NO: 1;
    (b) a DNA molecule which, via a co-suppression effect, reduces the expression of at least one endogenous gene encoding a SSIII protein, said DNA molecule comprising at least 100 nucleotides of SEQ ID NO: 1; or
    (c) a DNA molecule that simultaneously encodes at least one antisense RNA and at least one sense RNA, where said antisense RNA and said sense RNA form a double-stranded RNA molecule that reduces the expression of at least one endogenous gene encoding a SSIII protein, said DNA molecule comprising at least 100 nucleotides of SEQ ID NO: 1;

(2) a second foreign nucleic acid molecule, wherein said second foreign nucleic acid molecule is
    (a) a DNA molecule encoding at least one antisense RNA that reduces the expression of at least one endogenous gene encoding a BEI protein, said DNA molecule comprising at least 100 nucleotides of SEQ ID NO: 4;
- (b) a DNA molecule which, via a co-suppression effect, reduces the expression of at least one endogenous gene encoding a BEI protein, said DNA molecule comprising at least 100 nucleotides of SEQ ID NO: 4; or
- (c) a DNA molecule that simultaneously encodes at least one antisense RNA and at least one sense RNA, where said antisense RNA and said sense RNA form a double-stranded RNA molecule that reduces the expression of at least one endogenous gene encoding a BEI protein, said DNA molecule comprising at least 100 nucleotides of SEQ ID NO: 4; and (3) a third foreign nucleic acid molecule, wherein said third foreign nucleic acid molecule is
  - (a) a DNA molecule encoding at least one antisense RNA that reduces the expression of at least one endogenous gene encoding a BEII protein, said DNA molecule comprising at least 100 nucleotides of SEQ ID NO: 6;
  - (b) a DNA molecule which, via a co-suppression effect, reduces the expression of at least one endogenous gene encoding a BEII protein, said DNA molecule comprising at least 100 nucleotides of SEQ ID NO: 6; or
  - (c) a DNA molecule that simultaneously encodes at least one antisense RNA and at least one sense RNA, where said antisense RNA and said sense RNA form a double-stranded RNA molecule that reduces the expression of at least one endogenous gene encoding a BEII protein, said DNA molecule comprising at least 100 nucleotides of SEQ ID NO: 6, and further wherein said genetically modified plant cell synthesizes a modified starch, which after gelatinization of a 6% suspension in water forms a gel with a gel strength that is increased by at least 300% in comparison with the gel strength of starch extracted from corresponding plant cells, of wild-type plants, which have not been genetically modified.

17. The method of claim 16, wherein
said first foreign nucleic acid molecule is a DNA molecule encoding at least one antisense RNA that reduces the expression of at least one endogenous gene encoding a SSIII protein, said DNA molecule comprising at least 100 nucleotides of SEQ ID NO: 1;
said second foreign nucleic acid molecule is a DNA molecule encoding at least one antisense RNA that reduces the expression of at least one endogenous gene encoding a BEI protein, said DNA molecule comprising at least 100 nucleotides of SEQ ID NO: 4; and
said third foreign nucleic acid molecule is a DNA molecule encoding at least one antisense RNA that reduces the expression of at least one endogenous gene encoding a BEII protein, said DNA molecule comprising at least 100 nucleotides of SEQ ID NO: 6.

18. The method of claim 16, wherein
(1) said first foreign nucleic acid molecule is
  - (a) a DNA molecule encoding at least one antisense RNA that reduces the expression of at least one endogenous gene encoding a SSIII protein, said DNA molecule comprising at least 500 nucleotides of SEQ ID NO: 1;
  - (b) a DNA molecule which, via a co-suppression effect, reduces the expression of at least one endogenous gene encoding a SSIII protein, said DNA molecule comprising at least 500 nucleotides of SEQ ID NO: 1; or
  - (c) a DNA molecule that simultaneously encodes at least one antisense RNA and at least one sense RNA, where said antisense RNA and said sense RNA form a double-stranded RNA molecule that reduces the expression of at least one endogenous gene encoding a SSIII protein, said DNA molecule comprising at least 500 nucleotides of SEQ ID NO: 1,
(2) a second foreign nucleic acid molecule, wherein said second foreign nucleic acid molecule is
  - (a) a DNA molecule encoding at least one antisense RNA that reduces the expression of at least one endogenous gene encoding a BEI protein, said DNA molecule comprising at least 500 nucleotides of SEQ ID NO: 4;
  - (b) a DNA molecule which, via a co-suppression effect, reduces the expression of at least one endogenous gene encoding a BEI protein, said DNA molecule comprising at least 500 nucleotides of SEQ ID NO: 4; or
  - (c) a DNA molecule that simultaneously encodes at least one antisense RNA and at least one sense RNA, where said antisense RNA and said sense RNA form a double-stranded RNA molecule that reduces the expression of at least one endogenous gene encoding a BEI protein, said DNA molecule comprising at least 500 nucleotides of SEQ ID NO: 4; and
(3) a third foreign nucleic acid molecule, wherein said third foreign nucleic acid molecule is
  - (a) a DNA molecule encoding at least one antisense RNA that reduces the expression of at least one endogenous gene encoding a BEII protein, said DNA molecule comprising at least 500 nucleotides of SEQ ID NO: 6;
  - (b) a DNA molecule which, via a co-suppression effect, reduces the expression of at least one endogenous gene encoding a BEII protein, said DNA molecule comprising at least 500 nucleotides of SEQ ID NO: 6; or
  - (c) a DNA molecule that simultaneously encodes at least one antisense RNA and at least one sense RNA, where said antisense RNA and said sense RNA form a double-stranded RNA molecule that reduces the expression of at least one endogenous gene encoding a BEII protein, said DNA molecule comprising at least 500 nucleotides of SEQ ID NO: 6.

19. The method of claim 18, wherein
said first foreign nucleic acid molecule is a DNA molecule encoding at least one antisense RNA that reduces the expression of at least one endogenous gene encoding a SSIII protein, said DNA molecule comprising at least 500 nucleotides of SEQ ID NO: 1;
said second foreign nucleic acid molecule is a DNA molecule encoding at least one antisense RNA that reduces the expression of at least one endogenous gene encoding a BEI protein, said DNA molecule comprising at least 500 nucleotides of SEQ ID NO: 4; and
said third foreign nucleic acid molecule is a DNA molecule encoding at least one antisense RNA that reduces the expression of at least one endogenous gene encoding a BEII protein, said DNA molecule comprising at least 500 nucleotides of SEQ ID NO: 6.

20. The method of claim 16, wherein said plant cell is a potato plant cell.

* * * * *

UNITED STATES PATENT AND TRADEMARK OFFICE
CERTIFICATE OF CORRECTION

PATENT NO. : 8,017,832 B2  
APPLICATION NO. : 12/714167  
DATED : September 13, 2011  
INVENTOR(S) : Michaela Hoehne Page 1 of 1

It is certified that error appears in the above-identified patent and that said Letters Patent is hereby corrected as shown below:

In Column 71, lines 12-18, the text should be indented the same as lines Column 71, lines 4-11, as this is part of (c) which begins in Column 71, line 4.

In Column 73, line 15 at "(3)," the text should be indented the same as (1) at Column 72, line 45 and (2), at Column 72, line 64, as this is all part of Claim 16 which started in Column 72, line 41.

Signed and Sealed this
First Day of May, 2012

David J. Kappos
*Director of the United States Patent and Trademark Office*